(12) United States Patent
Pillow et al.

(10) Patent No.: US 11,648,315 B2
(45) Date of Patent: May 16, 2023

(54) SILVESTROL ANTIBODY-DRUG CONJUGATES AND METHODS OF USE

(71) Applicant: Genentech, Inc., South San Francisco, CA (US)

(72) Inventors: Thomas Pillow, San Francisco, CA (US); Andrew G. Polson, San Francisco, CA (US); Bing Zheng, Mountain View, CA (US)

(73) Assignee: Genentech, Inc., South San Francisco, CA (US)

(*) Notice: Subject to any disclaimer, the term of this patent is extended or adjusted under 35 U.S.C. 154(b) by 377 days.

(21) Appl. No.: 16/827,083

(22) Filed: Mar. 23, 2020

(65) Prior Publication Data

US 2020/0222545 A1 Jul. 16, 2020

Related U.S. Application Data

(62) Division of application No. 15/613,477, filed on Jun. 5, 2017, now Pat. No. 10,639,378.

(60) Provisional application No. 62/346,024, filed on Jun. 6, 2016.

(51) Int. Cl.

| | | |
|---|---|---|
| *A61K 31/357* | (2006.01) | |
| *A61K 45/06* | (2006.01) | |
| *C07D 407/12* | (2006.01) | |
| *C07K 19/00* | (2006.01) | |
| *G01N 33/567* | (2006.01) | |
| *A61K 47/54* | (2017.01) | |
| *A61K 47/68* | (2017.01) | |
| *A61K 39/00* | (2006.01) | |

(52) U.S. Cl.
CPC .......... *A61K 47/541* (2017.08); *A61K 31/357* (2013.01); *A61K 45/06* (2013.01); *A61K 47/6803* (2017.08); *A61K 47/6849* (2017.08); *A61K 47/6855* (2017.08); *C07D 407/12* (2013.01); *C07K 19/00* (2013.01); *G01N 33/567* (2013.01); *A61K 2039/572* (2013.01); *A61K 2039/627* (2013.01)

(58) Field of Classification Search
CPC combination set(s) only.
See application file for complete search history.

(56) References Cited

U.S. PATENT DOCUMENTS

| | | |
|---|---|---|
| 5,208,020 A | 5/1993 | Chari et al. |
| 6,214,345 B1 | 4/2001 | Firestone et al. |
| 6,710,075 B2 | 3/2004 | Meurer-Grimes et al. |
| 7,223,837 B2 | 5/2007 | De Groot et al. |
| 7,498,298 B2 | 3/2009 | Doronina et al. |
| 7,521,541 B2 | 4/2009 | Eigenbrot et al. |
| 7,723,485 B2 | 5/2010 | Junutula et al. |
| 7,816,544 B2 | 10/2010 | Jones et al. |
| 8,137,509 B2 | 3/2012 | Porco et al. |
| 8,404,088 B2 | 3/2013 | Porco et al. |
| 10,639,378 B2 | 5/2020 | Pillow et al. |
| 2014/0255432 A1 | 9/2014 | Baiocchi et al. |
| 2018/0140724 A1* | 5/2018 | Deng ................. A61K 47/6855 |

FOREIGN PATENT DOCUMENTS

| | | |
|---|---|---|
| WO | 2004041812 A1 | 5/2004 |
| WO | 2006007634 A1 | 1/2006 |
| WO | 2007008603 A1 | 1/2007 |
| WO | 2009052249 A1 | 4/2009 |
| WO | 2013016658 A1 | 1/2013 |
| WO | 2013149159 A1 | 10/2013 |
| WO | 2013165940 A1 | 11/2013 |
| WO | 2013177055 A2 | 11/2013 |
| WO | 2015095124 A1 | 6/2015 |
| WO | 2015095223 A2 | 6/2015 |
| WO | 2015095227 A2 | 6/2015 |
| WO | 2016090050 A1 | 6/2016 |

OTHER PUBLICATIONS

Alinari, L , et al., "Dual Targeting of the Cyclin/Rb/E2F and Mitochondrial Pathways in Mantle Cell Lymphoma with the Translation Inhibitor Silvestrol", Clin Cancer res 18(17), 4600-4611 (2012).
CA Registry , "Absolute stereochemistry", RN 1402931-53-6, 1 page, entered Nov. 4, 2012.
Carl, P , et al., "A novel connector linkage applicable in prodrug design", J Med Chem 24(5), 479-480 (1981).
Carter, P , et al., "Antibody-Drug Conjugates for Cancer Therapy", The Cancer Journal 14(3), 154-169 (2008).
Cencic, R , et al., "Antitumor Activity and Mechanism of Action of the Cyclopenta[b]benzofuran, Silvestrol", PLoS One 4(4), e5223, 14 pages (2009).
Chari, R , et al., "Immunoconjugates Containing Novel Maytansinoids: Promising Anticancer Drugs", Cancer Res 52, 127-131 (1992).
Chari, R , et al., "Targeted Cancer Therapy: Conferring Specificity to Cytotoxic Drugs", Accounts of Chemical Research 41(1), 98-107 (2008).
Dornan, D , et al., "Therapeutic potential of an anti-CD79b antibody-drug conjugate, anti-CD79b-vc-MMAE, for the treatment of non-Hodgkin lymphoma", Blood 114, 2721-2729 (2009).
Doronina, S , et al., "Development of potent monoclonal antibody auristatin conjugates for cancer therapy", Nat Biotechnol 21, 778-784 (2003).
Doronina, S , et al., "Novel Peptide Linkers for Highly Potent Antibody-Auristatin Conjugate", Bioconjugate Chem 19, 1960-1963(2008).
Dubowchik, G , et al., "Cathepsin B-Labile Dipeptide Linkers for Lysosomal Release of Doxorubicin from Internalizing Immunoconjugates: Model Studies of Enzymatic Drug Release and Antigen-Specific in Vitro Anticancer Activity", Bioconjugate Chem 13, 855-869 (2002).

(Continued)

*Primary Examiner* — Jared Barsky
(74) *Attorney, Agent, or Firm* — Viksnins Harris Padys Malen LLP

(57) ABSTRACT

The invention relates generally to a silvestrol molecule activated with a leaving group. The invention further relates generally to an antibody-drug conjugate comprising an antibody conjugated by a linker to one or more silvestrol drug moieties and methods of treatment.

24 Claims, 6 Drawing Sheets

(56) References Cited

OTHER PUBLICATIONS

Dubowchik, G., et al., "Cathepsin B-Sensitive Dipeptide Prodrugs. 1. A Model Study of Structural Requirements for Efficient Release of Doxorubicin", Bioorganic & Medicinal Chemistry Letters 8, 3341-3346 (1998).

Dubowchik, G., et al., "Doxorubicin Immunoconjugates Containing Bivalent, Lysosomally-Cleavable Dipeptide Linkages", Bioorganic & Medicinal Chemistry Letters 12, 1529-1532 (2002).

Flygare, J., et al., "Antibody-Drug Conjugates for the Treatment of Cancer", Chem Biol Drug Des 81, 113-121 (2013).

Hwang, B., et al., "Silvestrol and Episilvestrol, Potential Anticancer Rocaglate Derivatives from Aglaia silvestris", J Org Chem 69, 3350-3358 (2004).

Junutula, J., et al., "Rapid identification of reactive cysteine residues for site-specific labeling of antibody-Fabs", Journal of Immunological Methods 332, 41-52 (2008).

Junutula, J., et al., "Site-specific conjugation of a cytotoxic drug to an antibody improves the therapeutic index", Nature Biotechnology 26(8), 925-932 (2008).

Liu, T., et al., "Synthetic Silvestrol Analogues as Potent and Selective Protein Synthesis Inhibitors", J Med Chem 55, 8859-8878 (2012).

Lucas, D., et al., "The novel plant-derived agent silvestrol has B-cell selective activity in chronic lymphocytic leukemia and acute lymphoblastic leukemia in vitro and in vivo", Blood 113(19), 4656-4666 (2009).

Nolting, B., "Linker Technologies for Antibody-Drug Conjugates", Laurent Ducry (ed.), Antibody-Drug Conjugates, Methods in Molecular Biology, vol. 1045, 71-100 (2013).

Pan, L., et al., "Rocaglamide, silvestrol and structurally related bioactive compounds from *Aglaia* species", Nat Prod Rep 31, 924-939 (2014).

Patent Cooperation Treaty, International Search Authority, Search Report and Written Opinion for PCT/US2017/035925, 15 pages, dated Sep. 12, 2017.

\* cited by examiner

SILVESTROL ANTIBODY-DRUG CONJUGATES AND METHODS OF USE

CROSS REFERENCE TO RELATED APPLICATIONS

This divisional application claims priority to U.S. application Ser. No. 15/613,477, filed 5 Jun. 2017, which claims the benefit under 35 USC § 119(e) of U.S. Provisional Application Ser. No. 62/346,024 filed on 6 Jun. 2016, each of which are incorporated by reference in their entirety.

FIELD OF THE INVENTION

The field of the invention relates generally to an antibody-drug conjugate comprising an antibody directly conjugated to one or more silvestrol molecules.

BACKGROUND OF THE INVENTION

Silvestrol and silvestrol derivatives refer to a family of antibacterial and antitumor agents (Lucas, D. M. et al (2009) Blood, 113, 4656-4666; Alinari, L. et al (2012) Clin. Cancer Res., 18, 4600-4611; Cencic, R., et al. (2009) PLoS One, 4, e5223; Hwang, B. Y. et al (2004) J. Org. Chem., 69:3350-3358; U.S. Pat. No. 6,710,075). Silvestrol and analogs are potent and selective protein synthesis inhibitors and have been studied for their anti-hyperproliferative properties (Liu, T. et al (2012) Journal of Medicinal Chemistry, 55(20):8859-8878; WO 2015/085221; WO 2013/016658; WO 2004/041812; U.S. Pat. Nos. 8,137,509; 8,404,088; WO 2006/007634; U.S. Pat. No. 7,816,544).

Silvestrol, (CAS:697235-38-4) is named as methyl (1R, 2R,3S,3aR,8bS)-6-(((2S,3R,6R)-6-((R)-1,2-dihydroxyethyl)-3-methoxy-1,4-dioxan-2-yl)oxy)-1,8b-dihydroxy-8-methoxy-3a-(4-methoxyphenyl)-3-phenyl-2,3,3a,8b-tetrahydro-1H-cyclopenta[b]benzofuran-2-carboxylate, and has the structure:

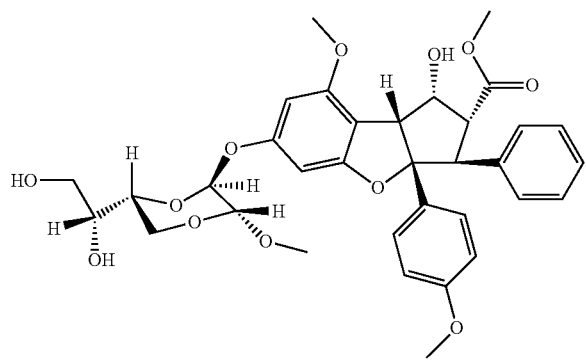

Antibody-drug conjugates, also known as ADC or immunoconjugates, are targeted chemotherapeutic molecules, combining the properties of both antibodies and cytotoxic drugs by targeting potent cytotoxic drugs to the antigen-expressing tumor cells, thereby enhancing their anti-tumor activity. Successful antibody-drug conjugate development for a given target antigen depends on optimization of antibody selection, linker stability, cytotoxic drug potency and mode of linker-drug conjugation to the antibody. More particularly, selective antibody-drug conjugates are characterized by at least one or more of the following: (i) an antibody-drug conjugate formation method wherein the antibody retains sufficient specificity to target antigens and wherein the drug efficacy is maintained; (ii) antibody-drug conjugate stability sufficient to limit drug release in the blood and concomitant damage to non-targeted cells; (iii) sufficient cell membrane transport efficiency (endocytosis) to achieve a therapeutic intracellular antibody-drug conjugate concentration; (iv) sufficient intracellular drug release from the antibody-drug conjugate sufficient to achieve a therapeutic drug concentration; and (v) drug cytotoxicity in nanomolar or sub-nanomolar amounts.

Antibody-drug conjugates allow for the targeted delivery of a drug moiety to a tumor, and, in some embodiments intracellular accumulation therein, where systemic administration of unconjugated drugs may result in unacceptable levels of toxicity to normal cells (Polakis P. (2005) Current Opinion in Pharmacology 5:382-387).

Antibody-drug conjugates are targeted chemotherapeutic molecules which combine properties of both antibodies and cytotoxic drugs by targeting potent cytotoxic drugs to antigen-expressing tumor cells (Teicher, B. A. (2009) Current Cancer Drug Targets 9:982-1004), thereby enhancing the therapeutic index by maximizing efficacy and minimizing off-target toxicity (Carter, P. J. and Senter P. D. (2008) The Cancer Jour. 14(3):154-169; Chari, R. V. (2008) Acc. Chem. Res. 41:98-107.

Antibodies have been developed that provide for site-specific conjugation of a drug to the antibody through cysteine substitutions at sites where the engineered cysteines are available for conjugation but do not perturb immunoglobulin folding and assembly or alter antigen binding and effector functions (Junutula, et al., 2008b Nature Biotech., 26(8):925-932; Dornan et al. (2009) Blood 114(13):2721-2729; U.S. Pat. Nos. 7,521,541; 7,723,485; WO2009/052249). These THIOMAB™ antibodies can then be conjugated to cytotoxic drugs through the engineered cysteine thiol groups to obtain THIOMAB™ drug conjugates (TDC) with uniform stoichiometry (e.g., up to 2 drugs per antibody in an antibody that has a single engineered cysteine site). Studies with multiple antibodies against different antigens have shown that TDCs are as efficacious as conventional antibody-drug conjugate in xenograft models and are tolerated at higher doses in relevant preclinical models. THIOMAB™ antibodies have been engineered for drug attachment at different locations of the antibody (e.g., specific amino acid positions (i.e., sites) within the light chain-Fab, heavy chain-Fab and heavy chain-Fc). The in vitro and in vivo stability, efficacy and PK properties of THIOMAB™ antibodies provide a unique advantage over conventional antibody-drug conjugates due to their homogeneity and site-specific conjugation to cytotoxic drugs.

There are still other limitations or challenges to the design, preparation and use of antibody-drug conjugates. For example, some linkers may be labile in the blood stream, thereby releasing unacceptable amounts of the drug prior to internalization in a target cell (Khot, A. et al (2015) Bioanalysis 7(13):1633-1648). Other linkers may provide stability in the bloodstream, but intracellular release effectiveness may be negatively impacted. Linkers that provide for desired intracellular release typically have poor stability in the bloodstream. Alternatively stated, bloodstream stability and intracellular release are typically inversely related. Second, in standard conjugation processes, the amount of drug moiety loaded on the antibody carrier protein (the drug loading), the amount of aggregate that is formed in the conjugation reaction, and the yield of final purified conjugate that can be obtained are interrelated. For example, aggregate formation is generally positively correlated to the number of equivalents of drug moiety and derivatives thereof conjugated to the carrier-antibody. Under high drug loading, formed aggregates must be removed for therapeutic applications. As a result, drug loading-mediated aggregate formation decreases antibody-drug conjugate yield and can render process scale-up difficult. Accordingly, there is a continuing need for improved efficacious antibody-drug conjugates that provide for optimized safety and efficacy.

SUMMARY

The present disclosure is generally directed to antibody-drug conjugates comprising an antibody linked by conjugation to one or more silvestrol derivatives. The present disclosure is further directed to silvestrol derivative intermediate compositions comprising a leaving group. Such intermediate compositions are suitable substrates for formation of antibody-drug conjugates wherein an antibody may be covalently bound to silvestrol derivative, through a linker or linking moiety. The present disclosure is further directed to use of such an antibody-silvestrol conjugate in the treatment of an illness, in particular cancer. As used herein, unless otherwise specified, silvestrol refers to the silvestrol derivative compounds encompassed by the present disclosure.

The invention includes an antibody-drug conjugate compound comprising an antibody covalently attached through a linker to a silvestrol drug moiety, selected from Formulas Ia and Ib:

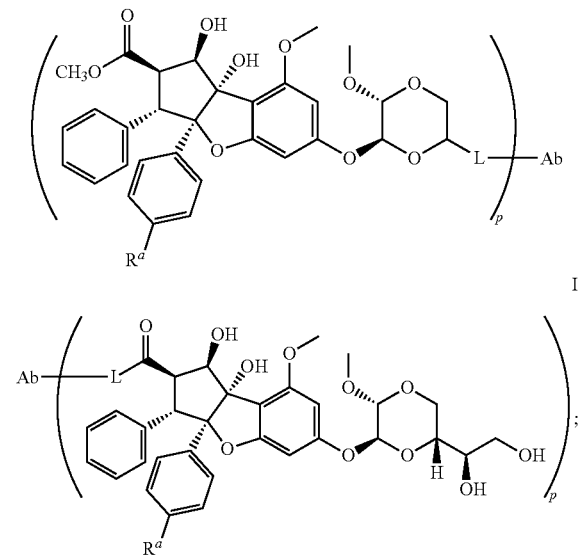

or a pharmaceutically acceptable salt thereof,
wherein
$R^a$ is a group selected from $CH_3O$, CN, $NO_2$, and Cl;
L is a linker;
p is an integer from 1 to 8; and
Ab is an antibody which binds to one or more tumor-associated antigens or cell-surface receptors.

The invention includes a pharmaceutical composition comprising the antibody-drug conjugate compound selected from Formulas Ia and Ib, and a pharmaceutically acceptable diluent, carrier or excipient.

The invention includes the use of the antibody-drug conjugate compound selected from Formulas Ia and Ib in the manufacture of a medicament for the treatment of cancer in a mammal.

The invention includes a method of treating cancer comprising administering to a patient the pharmaceutical composition comprising the antibody-drug conjugate compound selected from Formulas Ia and Ib.

The invention includes the antibody-drug conjugate compound selected from Formulas Ia and Ib for use in a method for treating cancer.

The invention includes an article of manufacture comprising the pharmaceutical composition comprising the antibody-drug conjugate compound selected from Formulas Ia and Ib, a container, and a package insert or label indicating that the pharmaceutical composition can be used to treat cancer.

The invention includes a silvestrol-linker intermediate compound of Formula II:

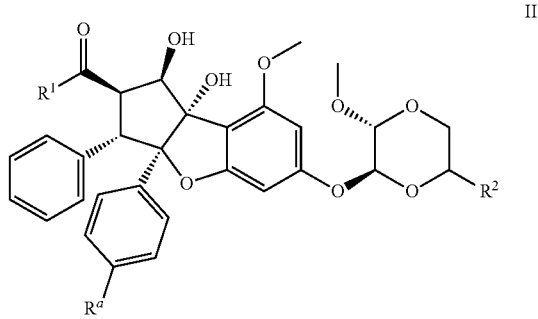

wherein
$R^a$ is a group selected from $CH_3O$, CN, $NO_2$, and Cl;
$R^1$ is selected from $—OCH_3$ and L-X; and
$R^2$ is selected from $—CH(OH)CH_2OH$, and L-X
L is a linker; and
X comprises a reactive functional group selected from maleimide, thiol, amino, bromide, bromoacetamido, iodoacetamido, p-toluenesulfonate, iodide, hydroxyl, carboxyl, pyridyl disulfide, and N-hydroxysuccinimide.

The invention includes a method of making an antibody-drug conjugate compound selected from Formulas Ia and Ib, the method comprising reacting an antibody with a silvestrol-linker intermediate compound of Formula II.

BRIEF DESCRIPTION OF THE DRAWINGS

1) Vehicle (HisAc 20 mM, Sucr 240 mM, TW-20 0.02%, pH 5.5), 100 uL, IV once
2) Thio anti-CD22 LC-K149C-MC-vc-PAB-Silvestrol-amine, ADC-104, 1 mg/kg IV once
3) Thio anti-CD22 LC-K149C-MC-vc-PAB-Silvestrol-amine, ADC-104, 3 mg/kg IV once
4) Thio anti-CD22 LC-K149C-MC-vc-PAB-Silvestrol-amine, ADC-104, 6 mg/kg IV once,
5) Thio anti-CD22 LC-K149C-MC-vc-PAB-Silvestrol-amine, ADC-104, 10 mg/kg IV once
6) Thio anti-Her2 7C2 LC-K149C-MC-vc-PAB-Silvestrol-amine, ADC-103, 3 mg/kg IV once

1) Vehicle (HisAc 20 mM, Sucr 240 mM, TW-20 0.02%, pH 5.5), 100 uL, IV once
2) Silvestrol, 0.09 mg/kg, IV once
3) Silvestrol, 1 mg/kg, IP qdX5 for 2 weeks
4) Thio anti-Her2 7C2 LC-K149C-MC-vc-PAB-Silvestrol-amine, ADC-103, 1 mg/kg IV once
5) Thio anti-Her2 7C2 LC-K149C-MC-vc-PAB-Silvestrol-amine, ADC-103, 3 mg/kg IV once
6) Thio anti-Her2 7C2 LC-K149C-MC-vc-PAB-Silvestrol-amine, ADC-103, 6 mg/kg IV once
7) Thio anti-Her2 7C2 LC-K149C-MC-vc-PAB-Silvestrol-amine, ADC-103, 10 mg/kg IV once
8) Thio anti-CD22 LC-K149C-MC-vc-PAB-Silvestrol-amine, ADC-104, 3 mg/kg IV once

1) Vehicle (Histidine Buffer #8), 100 μL, IV once
2) Thio CD22 LC-K149C-MC-vc-PAB-Silvestrol-amine, ADC-104, 10 mg/kg IV once
3) Thio Her2(7C2) LC-K149C-MC-vc-PAB-Silvestrol-amine, ADC-103, 10 mg/kg IV once
4) Thio CD22 HC-A140C-MC-vc-PAB-amino-Silvestrol, ADC-105, 1 mg/kg IV once
5) Thio CD22 HC-A140C-MC-vc-PAB-amino-Silvestrol, ADC-105, 3 mg/kg IV once
6) Thio CD22 HC-A140C-MC-vc-PAB-amino-Silvestrol, ADC-105, 6 mg/kg IV once
7) Thio CD22 HC-A140C-MC-vc-PAB-amino-Silvestrol, ADC-105, 10 mg/kg IV once
8 Thio Her2(7C2) HC-A140C-MC-vc-PAB-amino-Silvestrol, ADC-106, 3 mg/kg IV once
9) Thio Her2(7C2) HC-A140C-MC-vc-PAB-amino-Silvestrol, ADC-106, 10 mg/kg IV once

Figure 1A:
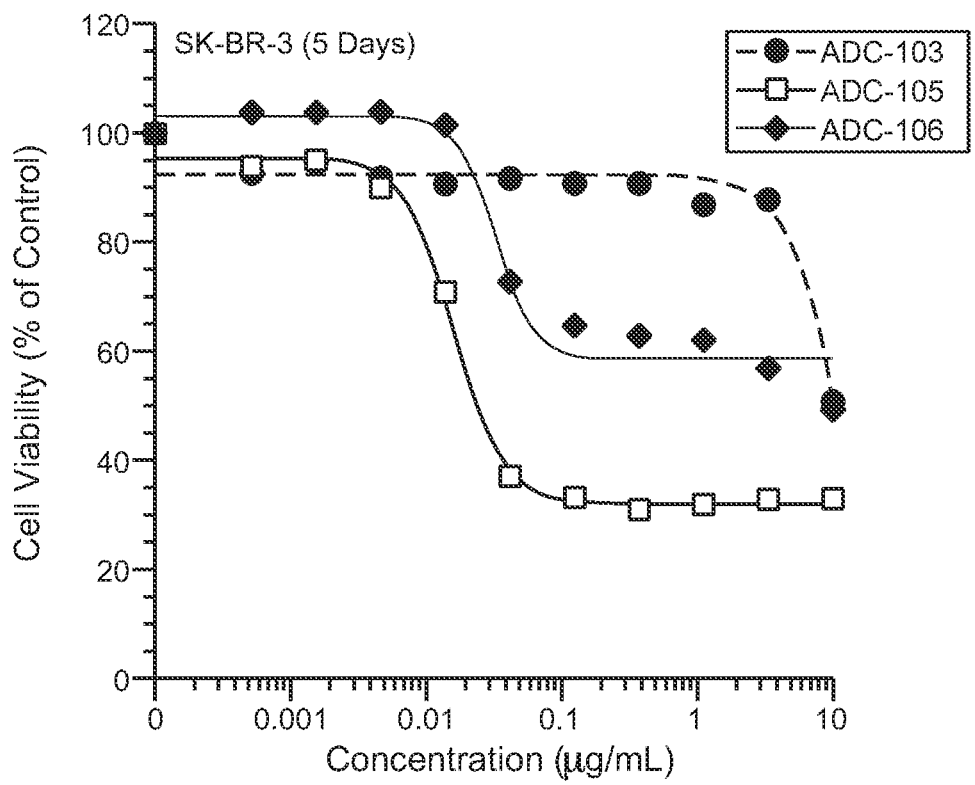
FIG. 1A shows a plot of in vitro cell viability of SK-BR-3 cells treated with Thio anti-Her2 7C2 LC-K149C-MC-vc-PAB-Silvestrol-amine, ADC-103, Thio Hu Anti-CD22 10F4v3 HC:A140C amino silvestrol analog, ADC-105, non-target control, and Thio Hu Anti-Her2 7C2 HC:A140C amino silvestrol analog, ADC-106

1) Vehicle (Histidine Buffer #8), 100 uL, IV once
2) Thio Hu anti-CD22 10F4v3 LC K149C-MC-sq-cit-PAB-Silvestrol-amine, ADC-110, 3 mg/kg IV once
3) Thio Hu anti-CD22 10F4v3 LC K149C-MC-sq-cit-PAB-Silvestrol-amine, ADC-110, 6 mg/kg IV once
4) Thio Hu anti-CD22 10F4v3 LC K149C-MC-sq-cit-PAB-Silvestrol-amine, ADC-110, 10 mg/kg IV once
5) Thio Hu anti-LY6E 9B12v12 LC K149C-MC-sq-cit-PAB-Silvestrol-amine, ADC-109, 10 mg/kg IV once
6) Thio Hu anti-CD22 10F4v3 LC K149C-MC-sq-cit-PAB-amino-Silvestrol, ADC-108, 0.3 mg/kg IV once
7) Thio Hu anti-CD22 10F4v3 LC K149C-MC-sq-cit-PAB-amino-Silvestrol, ADC-108, 1 mg/kg IV once
8) Thio Hu anti-CD22 10F4v3 LC K149C-MC-sq-cit-PAB-amino-Silvestrol, ADC-108, 3 mg/kg IV once
9) Thio Hu anti-CD22 10F4v3 LC K149C-MC-sq-cit-PAB-amino-Silvestrol, ADC-108, 6 mg/kg IV once
10) Thio Hu anti-LY6E 9B12v12 LC K149C-MC-sq-cit-PAB-amino-Silvestrol, ADC-107, 6 mg/kg IV once

DETAILED DESCRIPTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

Definitions

Unless defined otherwise, technical and scientific terms used herein have the same meaning as commonly understood by one of ordinary skill in the art to which this invention belongs, and are consistent with: Singleton et al. (1994) Dictionary of Microbiology and Molecular Biology, 2nd Ed., J. Wiley & Sons, New York, N.Y.; and Janeway, C., Travers, P., Walport, M., Shlomchik (2001) Immunobiology, 5th Ed., Garland Publishing, N.Y.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

The term "antibody" herein is used in the broadest sense and specifically covers monoclonal antibodies, polyclonal antibodies, dimers, multimers, multispecific antibodies (e.g., bispecific antibodies), and antibody fragments, so long as they exhibit the desired biological activity (Miller et al. (2003) Jour. of Immunology 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) Immuno Biology, 5th Ed., Garland Publishing, N.Y.). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

"Antibody fragments" comprise a portion of a full length antibody, generally the antigen binding or variable region thereof. Examples of antibody fragments include Fab, Fab', F(ab')2, and Fv fragments; diabodies; linear antibodies; minibodies (Olafsen et al. (2004) Protein Eng. Design & Sel. 17(4):315-323), fragments produced by a Fab expression library, anti-idiotypic (anti-Id) antibodies, CDR (complementary determining region), and epitope-binding fragments of any described herein which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al. (1975) Nature 256:495, or may be made by recombinant DNA methods (see for example: U.S. Pat. Nos. 4,816,567; 5,807,715). The monoclonal antibodies may also be isolated from phage antibody libraries using the techniques described in Clackson et al. (1991) Nature, 352:624-628; Marks et al. (1991) J. Mol. Biol., 222:581-597; for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al. (1984) Proc. Natl. Acad. Sci. USA, 81:6851-6855). Chimeric antibodies of interest herein include "primatized" antibodies comprising variable domain antigen-binding sequences derived from a non-human primate (e.g., Old World Monkey, Ape, etc.) and human constant region sequences.

An "intact antibody" herein is one comprising a VL and VH domains, as well as a light chain constant domain (CL) and heavy chain constant domains, CHL CH2 and CH3. The constant domains may be native sequence constant domains (e.g., human native sequence constant domains) or amino acid sequence variant thereof. The intact antibody may have one or more "effector functions" which refer to those biological activities attributable to the Fc constant region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; and down regulation of cell surface receptors such as B cell receptor and BCR.

Depending on the amino acid sequence of the constant domain of their heavy chains, intact antibodies can be assigned to different "classes." There are five major classes of intact immunoglobulin antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called $\alpha$, $\delta$, $\epsilon$, $\gamma$, and $\mu$, respectively. The subunit structures and three-dimensional configurations of different classes of immunoglobulins are well known. Ig forms include hinge-modifications or hingeless forms (Roux et al. (1998) J. Immunol. 161:4083-4090; Lund et al. (2000) Eur. J. Biochem. 267: 7246-7256; US 2005/0048572; US 2004/0229310).

A "cysteine engineered antibody" or "cysteine engineered antibody variant" is an antibody in which one or more residues of an antibody are substituted with cysteine residues. In accordance with the present disclosure, the thiol group(s) of the cysteine engineered antibodies can be conjugated to silvestrol to form a THIOMAB™ antibody (i.e., a THIOMAB™ drug conjugate (TDC), wherein in accordance with the present disclosure the drug is a silvestrol derivative). In particular embodiments, the substituted residues occur at accessible sites of the antibody. By substituting those residues with cysteine, reactive thiol groups are thereby positioned at accessible sites of the antibody and may be used to conjugate the antibody to the drug moiety to create an immunoconjugate, as described further herein. For example, a THIOMAB™ antibody may be an antibody with a single mutation of a non-cysteine native residue to a cysteine in the light chain (e.g., G64C, K149C or R142C according to Kabat numbering) or in the heavy chain (e.g., D101C or V184C or T205C according to Kabat numbering). In specific examples, a THIOMAB™ antibody has a single cysteine mutation in either the heavy or light chain such that each full-length antibody (i.e., an antibody with two heavy chains and two light chains) has two engineered cysteine residues. Cysteine engineered antibodies and preparatory methods are disclosed by US 2012/0121615 A1 (incorporated by reference herein in its entirety).

The terms "cancer" and "cancerous" refer to or describe the physiological condition in mammals that is typically characterized by unregulated cell growth/proliferation. Examples of cancer include, but are not limited to, carcinoma, lymphoma (e.g., Hodgkin's and non-Hodgkin's lymphoma), blastoma, sarcoma, and leukemia. More particular examples of such cancers include acute myeloid leukemia (AML), myelodysplastic syndrome (MDS), chronic myelogenous leukemia (CML), chronic myelomonocytic leukemia, acute promyelocytic leukemia (APL), chronic myeloproliferative disorder, thrombocytic leukemia, precursor B-cell acute lymphoblastic leukemia (pre-B-ALL), precursor T-cell acute lymphoblastic leukemia (preT-ALL), multiple myeloma (MM), mast cell disease, mast cell leukemia, mast cell sarcoma, myeloid sarcomas, lymphoid leukemia, and undifferentiated leukemia. In some embodiments, the cancer is myeloid leukemia. In some embodiments, the cancer is acute myeloid leukemia (AML).

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "epitope" refers to the particular site on an antigen molecule to which an antibody binds. In some embodiments, the particular site on an antigen molecule to which an antibody binds is determined by hydroxyl radical footprinting.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. Kuby Immunology, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest,* 5th Ed. Public Health Service, National Institutes of Health, Bethesda, Md. (1991).) With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

An "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated antibody" is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, $CH_2$, and $CH_3$). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

The term "leaving group," as used herein, refers to a sulfhydryl moiety that leaves in the course of a chemical reaction involving the groups as described herein.

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkylene" as used herein refers to a saturated linear or branched-chain divalent hydrocarbon radical of one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene (—$CH_2$—), ethylene (—$CH_2CH_2$—), propylene (—$CH_2CH_2CH_2$—), and the like.

The term "alkenyl" refers to linear or branched-chain monovalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$), and the like.

The term "alkenylene" refers to linear or branched-chain divalent hydrocarbon radical of two to eight carbon atoms ($C_2$-$C_8$) with at least one site of unsaturation, i.e., a carbon-carbon, $sp^2$ double bond, wherein the alkenylene radical may be optionally substituted independently with one or more substituents described herein, and includes radicals having "cis" and "trans" orientations, or alternatively, "E" and "Z" orientations. Examples include, but are not limited to, ethylenylene or vinylene (—CH=CH—), allyl (—$CH_2$CH=CH—), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —$CH_2$C≡CH), and the like.

The term "alkynylene" refers to a linear or branched divalent hydrocarbon radical of two to eight carbon atoms ($C_2$-$C_8$) with at least one site of unsaturation, i.e., a carbon-carbon, sp triple bond, wherein the alkynylene radical may be optionally substituted independently with one or more substituents described herein. Examples include, but are not limited to, ethynylene propynylene (propargylene, —$CH_2$C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo [2.2.2]octane and bicyclo[3.2.2]nonane. Spiro carbocyclyl moieties are also included within the scope of this definition.

Examples of spiro carbocyclyl moieties include [2.2]pentanyl, [2.3]hexanyl, and [2.4]heptanyl. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Carbocyclyl groups are optionally substituted independently with one or more substituents described herein.

The term "aryl" as used herein alone or as part of another group denotes optionally substituted homocyclic aromatic groups, preferably monocyclic or bicyclic groups containing from 5 to 20 carbons, from 5 to 10 carbons, or from 5 to 6 carbons in the ring portion, including, but not limited to, phenyl, biphenyl, naphthyl, substituted phenyl, substituted biphenyl or substituted naphthyl. The aryl moieties may optionally comprise one or more hetero atoms selected from O, S and N. Such heteroaromatics may comprise 1 or 2 nitrogen atoms, 1 or 2 sulfur atoms, 1 or 2 oxygen atoms, and combinations thereof, in the ring, wherein the each hetero atom is bonded to the remainder of the molecule through a carbon. Non limiting exemplary groups include pyridine, pyrazine, pyrimidine, pyrazole, pyrrole, imidazole, thiophene, thiopyrrilium, parathiazine, indole, purine, benzimidazole, quinolone, and phenothiazine. Non-limiting exemplary substituents include one or more of the following groups: alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxy, keto, ketal, phospho, nitro, and thio.

The "substituted" moieties described herein are moieties such as alkyl and aryl which are substituted with at least one atom other than carbon, including moieties in which a carbon chain atom is substituted with a hetero atom such as nitrogen, oxygen, silicon, phosphorous, boron, sulfur, or a halogen atom. These substituents include, but are not limited to, halogen, heterocyclo, alkoxy, alkenoxy, alkynoxy, aryloxy, hydroxy, keto, acyl, acyloxy, nitro, tertiary amino, amido, nitro, cyano, thio, sulfinate, sulfonamide, ketals, acetals, esters and ethers.

The terms "halogen" as used herein alone or as part of another group refer to chlorine, bromine, fluorine, and iodine.

Antibodies

In any of the embodiments of the disclosure, an antibody is humanized. In one embodiment, an antibody comprises HVRs as in any of the embodiments of the disclosure, and further comprises a human acceptor framework, e.g. a human immunoglobulin framework or a human consensus framework. In certain embodiments, the human acceptor framework is the human VL kappa I consensus (VLKI) framework and/or the VH framework VH1. In certain embodiments, the human acceptor framework is the human VL kappa I consensus (VLKI) framework and/or the VH framework VH1 comprising any one of the following mutations.

In another aspect, the antibody comprises a VH as in any of the embodiments provided herein, and a VL as in any of the embodiments provided herein.

In a further aspect of the invention, an antibody according to any of the embodiments herein is a monoclonal antibody, including a human antibody. In one embodiment, an antibody is an antibody fragment, e.g., a Fv, Fab, Fab', scFv, diabody, or F(ab')2 fragment. In another embodiment, the antibody is a substantially full length antibody, e.g., an IgG1 antibody, IgG2a antibody or other antibody class or isotype as defined herein.

In a further aspect, an antibody according to any of the embodiments herein may incorporate any of the features, singly or in combination, as described herein.

1. Antibody Affinity

In certain embodiments, an antibody provided herein has a dissociation constant (Kd) of $\leq 1$ µM, $\leq 100$ nM, $\leq 50$ nM, $\leq 10$ nM, $\leq 5$ nM, $\leq 1$ nM, $\leq 0.1$ nM, $\leq 0.01$ nM, or $\leq 0.001$ nM, and optionally is $\geq 10^{-13}$ M. (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000, BIACORE®-T200 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) and/or HBS-P (0.01 M Hepes pH7.4, 0.15M NaCl, 0.005% Surfactant P20) before injection at a flow rate of 5 µl/minute and/or 30 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$ (Chen et al. (1999) *J. Mol. Biol.* 293:865-881). If the on-rate exceeds $10^6 \text{ M}^{-1} \text{ s}^{-1}$ by the surface plasmon resonance assay describe herein, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')2, Fv, and scFv fragments, and other fragments described herein. For a review of certain antibody fragments, see Hudson et al. Nat. Med. 9:129-134 (2003). For a review of scFv fragments, see, e.g., Pluckthün, in The Pharmacology of Monoclonal Antibodies, vol. 113, Rosenburg and Moore eds., (Springer-Verlag, New York), pp. 269-315 (1994); see also WO 1993/16185; and U.S. Pat. No. 5,571,894 and US 5587,58. For discussion of Fab and F(ab')2 fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337; 7,527,791; 6,982,321; 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENO-MOUSE™ technology; U.S. Pat. No. 5,770,429 describing HuMAB® technology; U.S. Pat. No. 7,041,870 describing K-M MOUSE® technology; and US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.,* 133: 3001 (1984); Brodeur et al., *Monoclonal Antibody Production Techniques and Applications,* pp. 51-63 (Marcel Dekker, Inc., New York, 1987); and Boerner et al., *J. Immunol.,* 147: 86 (1991).) Human antibodies generated via human B-cell hybridoma technology are also described in Li et al., *Proc. Natl. Acad. Sci. USA,* 103:3557-3562 (2006). Additional methods include those described, for example, in U.S. Pat. No. 7,189,826 (describing production of monoclonal human IgM antibodies from hybridoma cell lines) and Ni, *Xiandai Mianyixue,* 26(4):265-268 (2006) (describing human-human hybridomas). Human hybridoma technology (Trioma technology) is also described in Vollmers and Brandlein, *Histology and Histopathology,* 20(3):927-937 (2005) and Vollmers and Brandlein, *Methods and Findings in Experimental and Clinical Pharmacology,* 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described herein.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178: 1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. The term "multispecific antibody" is used in the broadest sense and specifically covers an antibody comprising an antigen-binding domain that has polyepitopic specificity (i.e., is capable of specifically binding to two, or more, different epitopes on one biological molecule or is capable of specifically binding to epitopes on two, or more, different biological molecules). In some embodiments, multispecific antibodies are monoclonal antibodies that have binding specificities for at least two different sites. In some embodiments, an antigen-binding domain of a multispecific antibody (such as a bispecific antibody) comprises two VH/VL units, wherein a first VH/VL unit specifically binds to a first epitope and a second VH/VL unit specifically binds to a second epitope, wherein each VH/VL unit comprises a heavy chain variable domain (VH) and a light chain variable domain (VL). Such multispecific antibodies include, but are not limited to, full length antibodies, antibodies having two or more VL and VH domains, antibody fragments such as Fab, Fv, dsFv, scFv, diabodies, bispecific diabodies and triabodies, antibody fragments that have been linked covalently or non-covalently. A VH/VL unit that further comprises at least a portion of a heavy chain variable region and/or at least a portion of a light chain variable region may also be referred to as an "arm" or "hemimer" or "half antibody." In some embodiments, a hemimer comprises a sufficient portion of a heavy chain variable region to allow intramolecular disulfide bonds to be formed with a second hemimer. In some embodiments, a hemimer comprises a knob mutation or a hole mutation, for example, to allow heterodimerization with a second hemimer or half antibody that comprises a complementary hole mutation or knob mutation. Knob mutations and hole mutations are discussed further herein.

In certain embodiments, a multispecific antibody provided herein may be a bispecific antibody. The term "bispecific antibody" is used in the broadest sense and covers a multispecific antibody comprising an antigen-binding domain that is capable of specifically binding to two different epitopes on one biological molecule or is capable of specifically binding to epitopes on two different biological molecules. A bispecific antibody may also be referred to herein as having "dual specificity" or as being "dual specific." Bispecific antibodies can be prepared as full length antibodies or antibody fragments. The term "biparatopic antibody" as used herein, refers to a bispecific antibody where a first antigen-binding domain and a second antigen-binding domain bind to two different epitopes on the same antigen molecule or it may bind to epitopes on two different antigen molecules.

In some embodiments, the first antigen-binding domain and the second antigen-binding domain of the biparatopic antibody may bind the two epitopes within one and the same antigen molecule (intramolecular binding). For example, the first antigen-binding domain and the second antigen-binding domain of the biparatopic antibody may bind to two different epitopes on the same antibody molecule. In certain embodiments, the two different epitopes that a biparatopic antibody binds are epitopes that are not normally bound at the same time by one monospecific antibody, such as e.g. a conventional antibody or one immunoglobulin single variable domain.

In some embodiments, the first antigen-binding domain and the second antigen-binding domain of the biparatopic antibody may bind epitopes located within two distinct antigen molecules.

Techniques for making multispecific antibodies include, but are not limited to, recombinant co-expression of two immunoglobulin heavy chain-light chain pairs having different specificities (see Milstein and Cuello, *Nature* 305: 537

(1983)), WO 93/08829, and Traunecker et al., *EMBO J.* 10: 3655 (1991)), and "knob-in-hole" engineering (see, e.g., U.S. Pat. No. 5,731,168), WO2009/089004, US2009/ 0182127, US2011/0287009, Marvin and Zhu, Acta Pharmacol. Sin. (2005) 26(6):649-658, and Kontermann (2005) Acta Pharmacol. Sin., 26:1-9). The term "knob-into-hole" or "KnH" technology as used herein refers to the technology directing the pairing of two polypeptides together in vitro or in vivo by introducing a protuberance (knob) into one polypeptide and a cavity (hole) into the other polypeptide at an interface in which they interact. For example, KnHs have been introduced in the Fc:Fc binding interfaces, CL:CH1 interfaces or VH/VL interfaces of antibodies (see, e.g., US 2011/0287009, US2007/0178552, WO 96/027011, WO 98/050431, and Zhu et al., 1997, Protein Science 6:781-788). In some embodiments, KnHs drive the pairing of two different heavy chains together during the manufacture of multispecific antibodies. For example, multispecific antibodies having KnH in their Fc regions can further comprise single variable domains linked to each Fc region, or further comprise different heavy chain variable domains that pair with similar or different light chain variable domains. KnH technology can be also be used to pair two different receptor extracellular domains together or any other polypeptide sequences that comprises different target recognition sequences (e.g., including affibodies, peptibodies and other Fc fusions).

The term "knob mutation" as used herein refers to a mutation that introduces a protuberance (knob) into a polypeptide at an interface in which the polypeptide interacts with another polypeptide. In some embodiments, the other polypeptide has a hole mutation.

A "protuberance" refers to at least one amino acid side chain which projects from the interface of a first polypeptide and is therefore positionable in a compensatory cavity in the adjacent interface (i.e. the interface of a second polypeptide) so as to stabilize the heteromultimer, and thereby favor heteromultimer formation over homomultimer formation, for example. The protuberance may exist in the original interface or may be introduced synthetically (e.g. by altering nucleic acid encoding the interface). In some embodiments, nucleic acid encoding the interface of the first polypeptide is altered to encode the protuberance. To achieve this, the nucleic acid encoding at least one "original" amino acid residue in the interface of the first polypeptide is replaced with nucleic acid encoding at least one "import" amino acid residue which has a larger side chain volume than the original amino acid residue. It will be appreciated that there can be more than one original and corresponding import residue. The side chain volumes of the various amino residues are shown, for example, in Table 1 of US2011/ 0287009. A mutation to introduce a "protuberance" may be referred to as a "knob mutation."

In some embodiments, import residues for the formation of a protuberance are naturally occurring amino acid residues selected from arginine (R), phenylalanine (F), tyrosine (Y) and tryptophan (W). In some embodiments, an import residue is tryptophan or tyrosine. In some embodiment, the original residue for the formation of the protuberance has a small side chain volume, such as alanine, asparagine, aspartic acid, glycine, serine, threonine or valine.

A "cavity" refers to at least one amino acid side chain which is recessed from the interface of a second polypeptide and therefore accommodates a corresponding protuberance on the adjacent interface of a first polypeptide. The cavity may exist in the original interface or may be introduced synthetically (e.g. by altering nucleic acid encoding the interface). In some embodiments, nucleic acid encoding the interface of the second polypeptide is altered to encode the cavity. To achieve this, the nucleic acid encoding at least one "original" amino acid residue in the interface of the second polypeptide is replaced with DNA encoding at least one "import" amino acid residue which has a smaller side chain volume than the original amino acid residue. It will be appreciated that there can be more than one original and corresponding import residue. In some embodiments, import residues for the formation of a cavity are naturally occurring amino acid residues selected from alanine (A), serine (S), threonine (T) and valine (V). In some embodiments, an import residue is serine, alanine or threonine. In some embodiments, the original residue for the formation of the cavity has a large side chain volume, such as tyrosine, arginine, phenylalanine or tryptophan. A mutation to introduce a "cavity" may be referred to as a "hole mutation."

The protuberance is "positionable" in the cavity which means that the spatial location of the protuberance and cavity on the interface of a first polypeptide and second polypeptide respectively and the sizes of the protuberance and cavity are such that the protuberance can be located in the cavity without significantly perturbing the normal association of the first and second polypeptides at the interface. Since protuberances such as Tyr, Phe and Trp do not typically extend perpendicularly from the axis of the interface and have preferred conformations, the alignment of a protuberance with a corresponding cavity may, in some instances, rely on modeling the protuberance/cavity pair based upon a three-dimensional structure such as that obtained by X-ray crystallography or nuclear magnetic resonance (NMR). This can be achieved using widely accepted techniques in the art.

In some embodiments, a knob mutation in an IgG1 constant region is T366W. In some embodiments, a hole mutation in an IgG1 constant region comprises one or more mutations selected from T366S, L368A and Y407V. In some embodiments, a hole mutation in an IgG1 constant region comprises T366S, L368A and Y407V.

In some embodiments, a knob mutation in an IgG4 constant region is T366W. In some embodiments, a hole mutation in an IgG4 constant region comprises one or more mutations selected from T366S, L368A, and Y407V. In some embodiments, a hole mutation in an IgG4 constant region comprises T366S, L368A, and Y407V.

Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science,* 229: 81 (1985)); using leucine zippers to produce bi-specific antibodies (see, e.g., Kostelny et al., *J. Immunol.,* 148(5):1547-1553 (1992)); using "diabody" technology for making bispecific antibody fragments (Hollinger et al., *Proc. Natl. Acad. Sci. USA,* 90:6444-6448 (1993)); and using single-chain Fv (sFv) dimers (Gruber et al., *J. Immunol.,* 152:5368 (1994)); and preparing trispecific antibodies as described, e.g., in Tutt et al. *J. Immunol.* 147: 60 (1991).

Engineered antibodies with three or more functional antigen binding sites, including "Octopus antibodies" or "dual-variable domain immunoglobulins" (DVDs) are also included herein (US 2006/0025576A1, and Wu et al. (2007) *Nature Biotechnology*).

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); U.S. Pat. No. 5,821,337 (see Bruggemann, M. et al., J. Exp. Med. 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103:2738-2743 (2004)). FcRn binding and in vivo clearance/half life determinations can also be performed using methods known in the art (Petkova, S. B. et al., Int'l. Immunol. 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

In certain embodiments Pro329 of a wild-type human Fc region is substituted with glycine or arginine or an amino acid residue large enough to destroy the proline sandwich within the Fc/Fcγ receptor interface, that is formed between the proline329 of the Fc and tryptophan residues Trp 87 and Trp 110 of FcgRIII (Sondermann et al.: Nature 406, 267-273 (20 Jul. 2000)). In a further embodiment, at least one further amino acid substitution in the Fc variant is S228P, E233P, L234A, L235A, L235E, N297A, N297D, or P331S and still in another embodiment said at least one further amino acid substitution is L234A and L235A of the human IgG1 Fc region or S228P and L235E of the human IgG4 Fc region (U.S. Pat. No. 8,969,526 which is incorporated by reference in its entirety).

In certain embodiments, a polypeptide comprises the Fc variant of a wild-type human IgG Fc region wherein the polypeptide has Pro329 of the human IgG Fc region substituted with glycine and wherein the Fc variant comprises at least two further amino acid substitutions at L234A and L235A of the human IgG1 Fc region or S228P and L235E of the human IgG4 Fc region, and wherein the residues are numbered according to the EU index of Kabat (U.S. Pat. No. 8,969,526 which is incorporated by reference in its entirety). In certain embodiments, the polypeptide comprising the P329G, L234A and L235A substitutions exhibit a reduced affinity to the human FcγRIIIA and FcγRIIA, for down-modulation of ADCC to at least 20% of the ADCC induced by the polypeptide comprising the wild type human IgG Fc region, and/or for down-modulation of ADCP (U.S. Pat. No. 8,969,526 which is incorporated by reference in its entirety).

In a specific embodiment the polypeptide comprising an Fc variant of a wild type human Fc polypeptide comprises a triple mutation: an amino acid substitution at position Pro329, a L234A and a L235A mutation (P329/LALA) (U.S. Pat. No. 8,969,526 which is incorporated by reference in its entirety). In specific embodiments, the polypeptide comprises the following amino acid substitutions: P329G, L234A, and L235A.

Certain antibody variants with improved or diminished binding to FcRs are described. (See, e.g., U.S. Pat. No. 6,737,056; WO 2004/056312, and Shields et al., (2001) J. Biol. Chem. 9(2): 6591-6604).

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 1999/51642, and Idusogie et al., J. Immunol. 164: 4178-4184 (2000).

Antibodies with increased half-lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, Nature 322:738-40 (1988); U.S. Pat. Nos. 5,648,260; 5,624,821; and WO 1994/29351 concerning other examples of Fc region variants.

7. Cysteine Engineered Antibody Variants

In certain embodiments, it may be desirable to create cysteine engineered antibodies, e.g., "THIOMAB™ antibody," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to the drug moiety to create an immunoconjugate, as described further herein. In certain embodiments, any one or more of the following residues may be substituted with cysteine: V205 (Kabat numbering) of the light chain; K149 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541; Shen, B. et al (2012) Nat. Biotechnol. 30(2):184-189; Sukumaran et al (2015) Pharm Res 32:1884-1893.

Antibody-drug conjugates (ADC, immunoconjugates) may be formed by conjugating one or more antibody cysteine thiol groups to one or more linker moieties bound to a drug thereby forming an antibody-linker-drug complex. Cysteine thiols are reactive nucleophiles at neutral pH, unlike most amines which are protonated and less nucleophilic near pH 7. Since free thiol (RSH, sulfhydryl) groups are relatively reactive, proteins with cysteine residues often exist in their oxidized form as disulfide-linked oligomers or have internally bridged disulfide groups. Antibody cysteine thiol groups are generally more reactive, i.e. more nucleophilic, towards electrophilic conjugation reagents than antibody amine or hydroxyl groups. Engineering in cysteine thiol groups by the mutation of various amino acid residues of a protein to cysteine amino acids is potentially problematic, particularly in the case of unpaired (free Cys) residues or those which are relatively accessible for reaction or oxidation. In concentrated solutions of the protein, whether in the periplasm of E. coli, culture supernatants, or partially or completely purified protein, unpaired Cys residues on the surface of the protein can pair and oxidize to form intermolecular disulfides, and hence protein dimers or multimers. Disulfide dimer formation renders the new Cys unreactive for conjugation to a drug, ligand, or other label. Furthermore, if the protein oxidatively forms an intramolecular disulfide bond between the newly engineered Cys and an existing Cys residue, both Cys groups are unavailable for active site participation and interactions. Furthermore, the protein may be rendered inactive or non-specific, by misfolding or loss of tertiary structure (Zhang et al. (2002) Anal. Biochem. 311:1-9).

In some aspects, a THIOMAB™ antibody comprises one of the heavy or light chain cysteine substitutions listed in Table 1 below.

TABLE 1

Light chain cysteine mutation sites in a THIOMAB™ antibody

| Chain (HC/LC) | Residue | Screening Mutation Site # | GNE Mutation Site # | Kabat Mutation Site # |
| --- | --- | --- | --- | --- |
| LC | T | 22 | 22 | 22 |
| LC | K | 39 | 39 | 39 |
| LC | Y | 49 | 49 | 49 |
| LC | Y | 55 | 55 | 55 |
| LC | T | 85 | 85 | 85 |
| LC | T | 97 | 97 | 97 |
| LC | I | 106 | 106 | 106 |
| LC | R | 108 | 108 | 108 |
| LC | R | 142 | 142 | 142 |
| LC | K | 149 | 149 | 149 |
| LC | V | 205 | 205 | 205 |
| HC | T | 117 | 114 | 110 |
| HC | A | 143 | 140 | 136 |
| HC | L | 177 | 174 | 170 |
| HC | L | 182 | 179 | 175 |
| HC | T | 190 | 187 | 183 |
| HC | T | 212 | 209 | 205 |
| HC | V | 265 | 262 | 258 |
| HC | G | 374 | 371 | 367 |
| HC | Y | 376 | 373 | 369 |
| HC | E | 385 | 382 | 378 |
| HC | S | 427 | 424 | 420 |
| HC | N | 437 | 434 | 430 |
| HC | Q | 441 | 438 | 434 |

In other aspects, a THIOMAB™ antibody comprises one of the heavy chain cysteine substitutions listed in Table 2.

TABLE 2

Heavy chain cysteine mutation sites in a THIOMAB™ antibody

| Chain (HC/LC) | Residue | Screening Mutation Site # | GNE Mutation Site # | Kabat Mutation Site # |
| --- | --- | --- | --- | --- |
| HC | T | 117 | 114 | 110 |
| HC | A | 143 | 140 | 136 |
| HC | L | 177 | 174 | 170 |
| HC | L | 182 | 179 | 175 |
| HC | T | 190 | 187 | 183 |
| HC | T | 212 | 209 | 205 |
| HC | V | 265 | 262 | 258 |
| HC | G | 374 | 371 | 367 |
| HC | Y | 376 | 373 | 369 |
| HC | E | 385 | 382 | 378 |
| HC | S | 427 | 424 | 420 |
| HC | N | 437 | 434 | 430 |
| HC | Q | 441 | 438 | 434 |

In some other aspects, a THIOMAB™ antibody comprises one of the light chain cysteine substitutions listed in Table 3

TABLE 3

Light chain cysteine mutation sites in a THIOMAB™ antibody

| Chain (HC/LC) | Residue | Screening Mutation Site # | GNE Mutation Site # | Kabat Mutation Site # |
| --- | --- | --- | --- | --- |
| LC | I | 106 | 106 | 106 |
| LC | R | 108 | 108 | 108 |
| LC | R | 142 | 142 | 142 |
| LC | K | 149 | 149 | 149 |

In some other aspects, a THIOMAB™ antibody comprises one of the heavy or light chain cysteine substitutions listed in Table 4.

TABLE 4

Heavy chain cysteine mutation sites in a THIOMAB™ antibody

| Chain (HC/LC) | Residue | Screening Mutation Site # | GNE Mutation Site # | Kabat Mutation Site # |
| --- | --- | --- | --- | --- |
| LC | K | 149 | 149 | 149 |
| HC | A | 143 | 140 | 136 |
| HC | A | 121 | 118 | 114 |

Cysteine engineered antibodies which may be useful in the antibody-drug conjugates of the invention in the treatment of cancer include, but are not limited to, antibodies against cell surface receptors and tumor-associated antigens (TAA). Tumor-associated antigens are known in the art, and can be prepared for use in generating antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Examples of tumor-associated antigens TAA include, but are not limited to, TAA (1)-(53) listed herein. For convenience, information relating to these antigens, all of which are known in the art, is listed herein and includes names, alternative names, Genbank accession numbers and primary reference(s), following nucleic acid and protein sequence identification conventions of the National Center for Biotechnology Information (NCBI). Nucleic acid and protein sequences corresponding to TAA (1)-(53) are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

Figure 4:
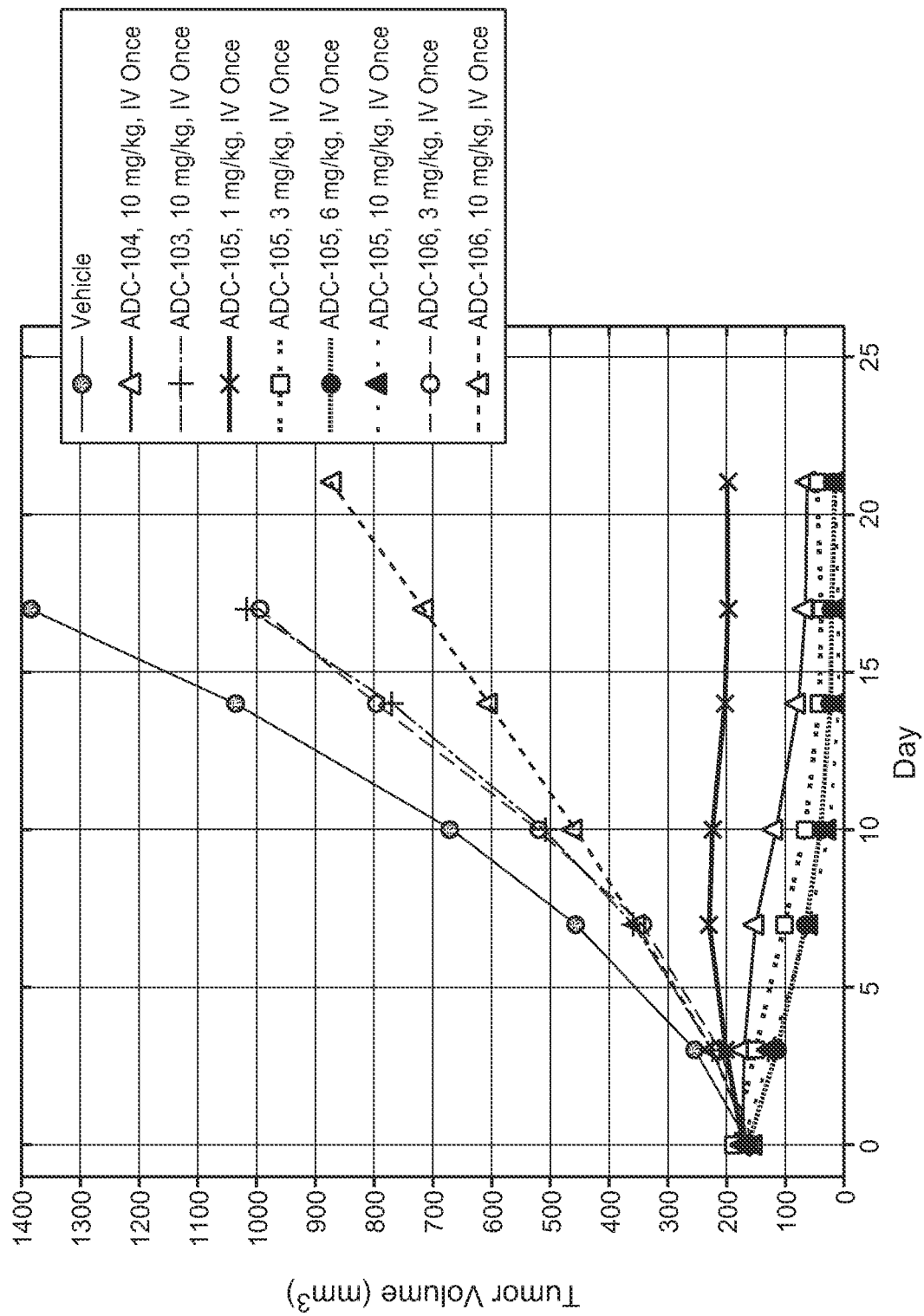
FIG. 4 shows the efficacy of antibody-drug conjugates in a plot of the in vivo fitted tumor volume change over time in Bjab-luc human xenograft model in CB-17 Fox Chase SCID mice.

Tumor-Associated Antigens (1) BMPR1B (bone morphogenetic protein receptor-type IB, Genbank accession no. NM_001203) ten Dijke, P., et al. Science 264 (5155):101-104 (1994), Oncogene 14 (11): 1377-1382 (1997)); WO2004063362 (Claim 2); WO2003042661 (Claim 12); US2003134790-A1 (Page 38-39); WO2002102235 (Claim 13; Page 296); WO2003055443 (Page 91-92); WO200299122 (Example 2; Page 528-530); WO2003029421 (Claim 6); WO2003024392 (Claim 2; FIG. 112); WO200298358 (Claim 1; Page 183); WO200254940 (Page 100-101); WO200259377(Page 349-350); WO200230268 (Claim 27; Page 376); WO200148204 (Example; FIG. 4) NP_001194 bone morphogenetic protein receptor, type IB/pid=NP_001194.1—Cross-references: MIM:603248; NP_001194.1; AY065994.

Figure 3:
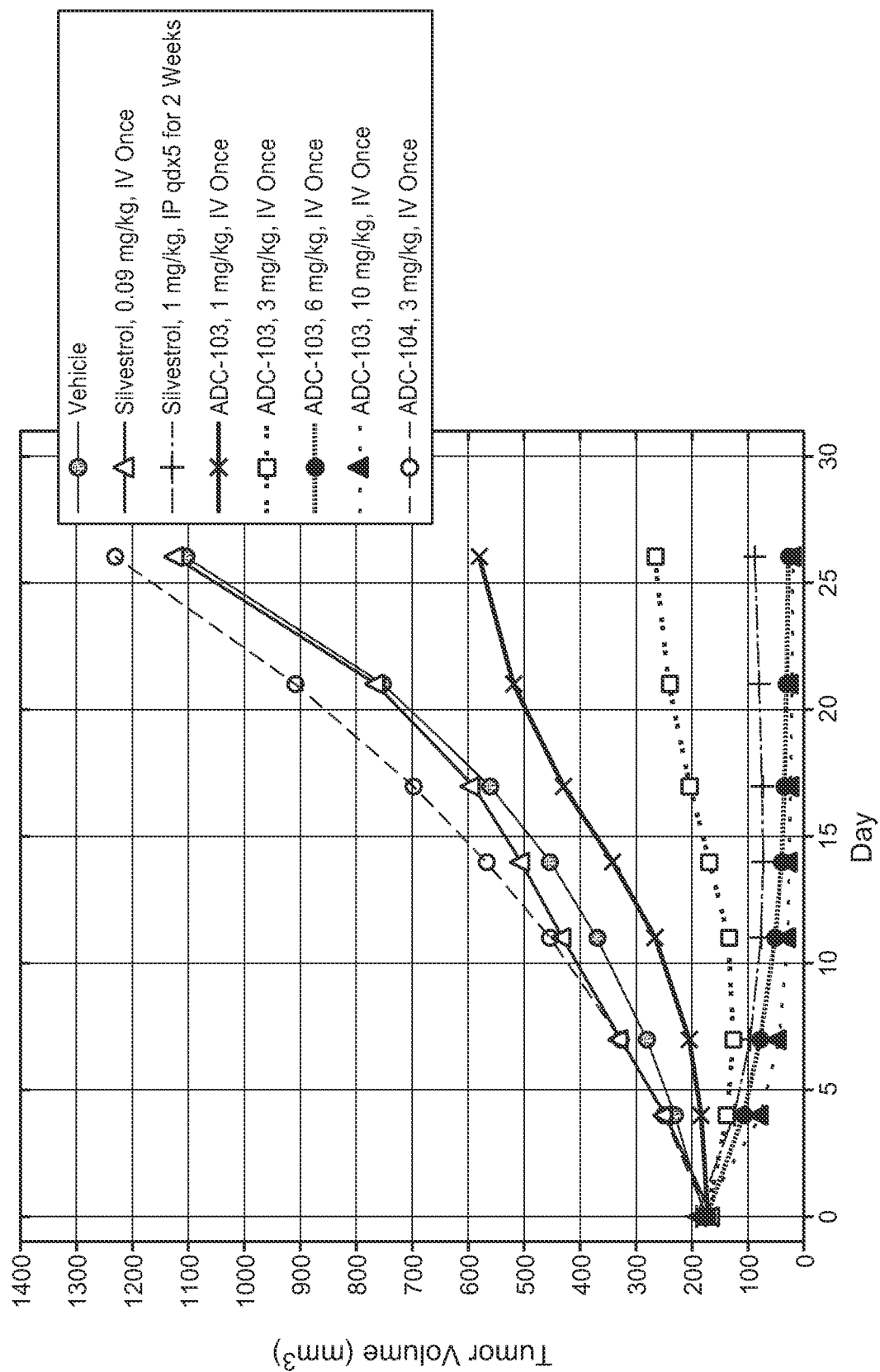
FIG. 3 shows the efficacy of antibody-drug conjugates in a plot of the in vivo fitted tumor volume change over time in in KPL4 human mammary xenograft model in scid beige mice.

(2) E16 (LAT1, SLC7A5, Genbank accession no. NM_003486) Biochem. Biophys. Res. Commun. 255 (2), 283-288 (1999), Nature 395 (6699):288-291 (1998), Gaugitsch, H. W., et al. (1992) J. Biol. Chem. 267 (16):11267-11273); WO2004048938 (Example 2); WO2004032842 (Example IV); WO2003042661 (Claim 12); WO2003016475 (Claim 1); WO200278524 (Example 2); WO200299074 (Claim 19; Page 127-129); WO200286443 (Claim 27; Pages 222, 393); WO2003003906 (Claim 10; Page 293); WO200264798 (Claim 33; Page 93-95); WO200014228 (Claim 5; Page 133-136); US2003224454 (FIG. 3); WO2003025138 (Claim 12; Page 150); NP_003477 solute carrier family 7 (cationic amino acid transporter, y+ system), member 5/pid=NP_003477.3—Homo sapiens Cross-references: MIM:600182; NP_003477.3; NM_015923; NM_003486_1.

Figure 2:
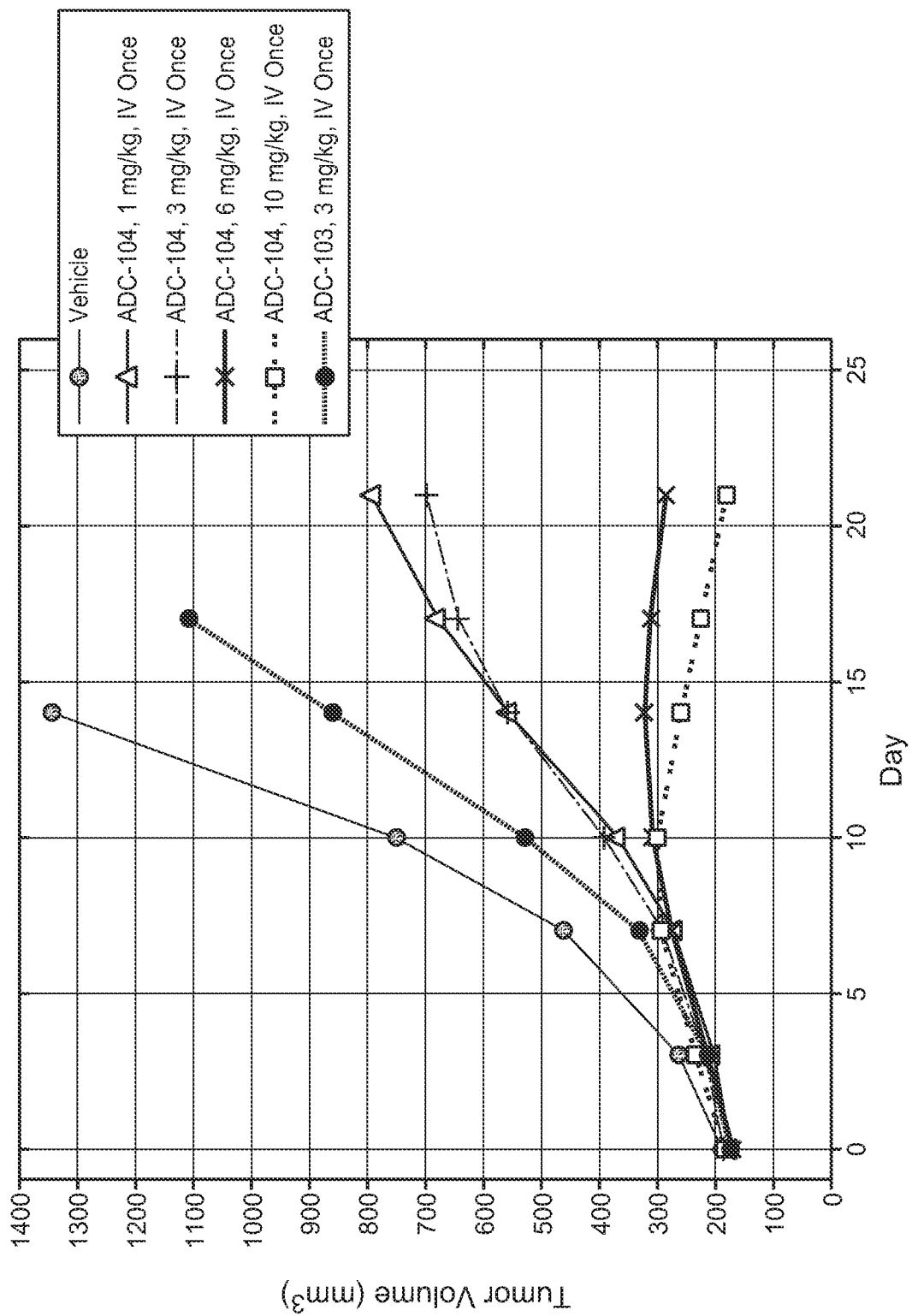
FIG. 2 shows the efficacy of antibody-drug conjugates in a plot of the in vivo fitted tumor volume change over time in Bjab-luc human xenograft model in CB-17 Fox Chase SCID mice.

(3) STEAP1 (six transmembrane epithelial antigen of prostate, Genbank accession no. NM_012449) Cancer Res. 61 (15), 5857-5860 (2001), Hubert, R. S., et al. (1999) Proc. Natl. Acad. Sci. U.S.A. 96 (25):14523-14528); WO2004065577 (Claim 6); WO2004027049 (FIG. 1L); EP1394274 (Example 11); WO2004016225 (Claim 2); WO2003042661 (Claim 12); US2003157089 (Example 5); US2003185830 (Example 5); US2003064397 (FIG. 2); WO200289747 (Example 5; Page 618-619); WO2003022995 (Example 9; FIG. 13A, Example 53; Page 173, Example 2; FIG. 2A); NP_036581 six transmembrane epithelial antigen of the prostate Cross-references: MIM: 604415; NP_036581.1; NM_012449_1.

(4) 0772P (CA125, MUC16, Genbank accession no. AF361486) J. Biol. Chem. 276 (29):27371-27375 (2001)); WO2004045553 (Claim 14); WO200292836 (Claim 6; FIG. 12); WO200283866 (Claim 15; Page 116-121); US2003124140 (Example 16); US 798959. Cross-references: GI:34501467; AAK74120.3; AF361486_1.

(5) MPF (MPF, MSLN, SMR, megakaryocyte potentiating factor, mesothelin, Genbank accession no. NM_005823) Yamaguchi, N., et al. Biol. Chem. 269 (2), 805-808 (1994), Proc. Natl. Acad. Sci. U.S.A. 96 (20):11531-11536 (1999), Proc. Natl. Acad. Sci. U.S.A. 93 (1):136-140 (1996), J. Biol. Chem. 270 (37):21984-21990 (1995)); WO2003101283 (Claim 14); (WO2002102235 (Claim 13; Page 287-288); WO2002101075 (Claim 4; Page 308-309); WO200271928 (Page 320-321); WO9410312 (Page 52-57); Cross-references: MIM:601051; NP_005814.2; NM_005823_1.

(6) Napi3b (NAPI-3B, NPTIIb, SLC34A2, solute carrier family 34 (sodium phosphate), member 2, type II sodium-dependent phosphate transporter 3b, Genbank accession no. NM_006424) J. Biol. Chem. 277 (22):19665-19672 (2002), Genomics 62 (2):281-284 (1999), Feild, J. A., et al. (1999) Biochem. Biophys. Res. Commun. 258 (3):578-582); WO2004022778 (Claim 2); EP1394274 (Example 11); WO2002102235 (Claim 13; Page 326); EP875569 (Claim 1; Page 17-19); WO200157188 (Claim 20; Page 329); WO2004032842 (Example IV); WO200175177 (Claim 24; Page 139-140); Cross-references: MIM:604217; NP_006415.1; NM_006424_1.

(7) Sema 5b (FLJ10372, KIAA1445, Mm.42015, SEMASB, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878) Nagase T., et al. (2000) DNA Res. 7 (2):143-150); WO2004000997 (Claim 1); WO2003003984 (Claim 1); WO200206339 (Claim 1; Page 50); WO200188133 (Claim 1; Page 41-43, 48-58); WO2003054152 (Claim 20); WO2003101400 (Claim 11); Accession: Q9P283; EMBL; AB040878; BAA95969.1. Genew; HGNC:10737.

(8) PSCA hlg (2700050C12Rik, C530008O16Rik, RIKEN cDNA 2700050C12, RIKEN cDNA 2700050C12 gene, Genbank accession no. AY358628); Ross et al. (2002) Cancer Res. 62:2546-2553; US2003129192 (Claim 2); US2004044180 (Claim 12); US2004044179 (Claim 11); US2003096961 (Claim 11); US2003232056 (Example 5); WO2003105758 (Claim 12); US2003206918 (Example 5); EP1347046 (Claim 1); WO2003025148 (Claim 20); Cross-references: GI:37182378; AAQ88991.1; AY358628_1.

(9) ETBR (Endothelin type B receptor, Genbank accession no. AY275463); Nakamuta M., et al. Biochem. Biophys. Res. Commun. 177, 34-39, 1991; Ogawa Y., et al. Biochem. Biophys. Res. Commun. 178, 248-255, 1991; Arai H., et al. Jpn. Circ. J. 56, 1303-1307, 1992; Arai H., et al. J. Biol. Chem. 268, 3463-3470, 1993; Sakamoto A., Yanagisawa M., et al. Biochem. Biophys. Res. Commun. 178, 656-663, 1991; Elshourbagy N. A., et al. J. Biol. Chem. 268, 3873-3879, 1993; Haendler B., et al. J. Cardiovasc. Pharmacol. 20, s1-S4, 1992; Tsutsumi M., et al. Gene 228, 43-49, 1999; Strausberg R. L., et al. Proc. Natl. Acad. Sci. U.S.A. 99, 16899-16903, 2002; Bourgeois C., et al. J. Clin. Endocrinol. Metab. 82, 3116-3123, 1997; Okamoto Y., et al. Biol. Chem. 272, 21589-21596, 1997; Verheij J. B., et al. Am. J. Med. Genet. 108, 223-225, 2002; Hofstra R. M. W., et al. Eur. J. Hum. Genet. 5, 180-185, 1997; Puffenberger E. G., et al. Cell 79, 1257-1266, 1994; Attie T., et al., Hum. Mol. Genet. 4, 2407-2409, 1995; Auricchio A., et al. Hum. Mol. Genet. 5:351-354, 1996; Amiel J., et al. Hum. Mol. Genet. 5, 355-357, 1996; Hofstra R. M. W., et al. Nat. Genet. 12, 445-447, 1996; Svensson P. J., et al. Hum. Genet. 103, 145-148, 1998; Fuchs S., et al. Mol. Med. 7, 115-124, 2001; Pingault V., et al. (2002) Hum. Genet. 111, 198-206; WO2004045516 (Claim 1); WO2004048938 (Example 2); WO2004040000 (Claim 151); WO2003087768 (Claim 1); WO2003016475 (Claim 1); WO2003016475 (Claim 1); WO200261087 (FIG. 1); WO2003016494 (FIG. 6); WO2003025138 (Claim 12; Page 144); WO200198351 (Claim 1; Page 124-125); EP522868 (Claim 8; FIG. 2); WO200177172 (Claim 1; Page 297-299); US2003109676; U.S. Pat. No. 6,518,404 (FIG. 3); U.S. Pat. No. 5,773,223 (Claim 1a; Col 31-34); WO2004001004.

(10) MSG783 (RNF124, hypothetical protein FLJ20315, Genbank accession no. NM_017763); WO2003104275 (Claim 1); WO2004046342 (Example 2); WO2003042661 (Claim 12); WO2003083074 (Claim 14; Page 61); WO2003018621 (Claim 1); WO2003024392 (Claim 2; FIG. 93); WO200166689 (Example 6); Cross-references: LocusID:54894; NP_060233.2; NM_017763_1.

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138) Lab. Invest. 82 (11):1573-1582 (2002)); WO2003087306; US2003064397 (Claim 1; FIG. 1); WO200272596 (Claim 13; Page 54-55); WO200172962 (Claim 1; FIG. 4B); WO2003104270 (Claim 11); WO2003104270 (Claim 16); US2004005598 (Claim 22); WO2003042661 (Claim 12); US2003060612 (Claim 12; FIG. 10); WO200226822 (Claim 23; FIG. 2); WO200216429 (Claim 12; FIG. 10); Cross-references: GI:22655488; AAN04080.1; AF455138_1.

(12) TrpM4 (BR22450, FLJ20041, TRPM4, TRPM4B, transient receptor potential cation channel, subfamily M, member 4, Genbank accession no. NM_017636) Xu, X. Z., et al. Proc. Natl. Acad. Sci. U.S.A. 98 (19):10692-10697 (2001), Cell 109 (3):397-407 (2002), J. Biol. Chem. 278 (33):30813-30820 (2003)); US2003143557 (Claim 4); WO200040614 (Claim 14; Page 100-103); WO200210382 (Claim 1; FIG. 9A); WO2003042661 (Claim 12); WO200230268 (Claim 27; Page 391); US2003219806 (Claim 4); WO200162794 (Claim 14; FIG. 1A-D); Cross-references: MIM:606936; NP_060106.2; NM_017636_1.

(13) CRIPTO (CR, CR1, CRGF, CRIPTO, TDGF1, teratocarcinoma-derived growth factor, Genbank accession no. NP_003203 or NM_003212) Ciccodicola, A., et al. EMBO J. 8 (7):1987-1991 (1989), Am. J. Hum. Genet. 49 (3):555-565 (1991)); US2003224411 (Claim 1); WO2003083041 (Example 1); WO2003034984 (Claim 12); WO200288170 (Claim 2; Page 52-53); WO2003024392 (Claim 2; FIG. 58); WO200216413 (Claim 1; Page 94-95, 105); WO200222808 (Claim 2; FIG. 1); U.S. Pat. No. 5,854,399 (Example 2; Col 17-18); U.S. Pat. No. 5,792,616 (FIG. 2); Cross-references: MIM:187395; NP_003203.1; NM_003212_1.

(14) CD21 (CR2 (Complement receptor 2) or C3DR (C3d/Epstein Barr virus receptor) or Hs.73792 Genbank accession no. M26004) Fujisaku et al. (1989) J. Biol. Chem. 264 (4):2118-2125); Weis J. J., et al. J. Exp. Med. 167, 1047-1066, 1988; Moore M., et al. Proc. Natl. Acad. Sci. U.S.A. 84, 9194-9198, 1987; Barel M., et al. Mol. Immunol. 35, 1025-1031, 1998; Weis J. J., et al. Proc. Natl. Acad. Sci. U.S.A. 83, 5639-5643, 1986; Sinha S. K., et al. (1993) J. Immunol. 150, 5311-5320; WO2004045520 (Example 4); US2004005538 (Example 1); WO2003062401 (Claim 9); WO2004045520 (Example 4); WO9102536 (FIG. 9.1-9.9); WO2004020595 (Claim 1); Accession: P20023; Q13866; Q14212; EMBL; M26004; AAA35786.1.

(15) CD79b (CD79B, CD79β, IGb (immunoglobulin-associated beta), B29, Genbank accession no. NM_000626 or 11038674) Proc. Natl. Acad. Sci. U.S.A. (2003) 100 (7):4126-4131, Blood (2002) 100 (9):3068-3076, Muller et al. (1992) Eur. J. Immunol. 22 (6):1621-1625); WO2004016225 (Claim 2, FIG. 140); WO2003087768, US2004101874 (Claim 1, page 102); WO2003062401 (Claim 9); WO200278524 (Example 2); US2002150573 (Claim 5, page 15); U.S. Pat. No. 5,644,033; WO2003048202 (Claim 1, pages 306 and 309); WO 99/558658, U.S. Pat. No. 6,534,482 (Claim 13, FIG. 17A/B); WO200055351 (Claim 11, pages 1145-1146); Cross-references: MIM:147245; NP_000617.1; NM_000626_1.

(16) FcRH2 (IFGP4, IRTA4, SPAP1A (SH2 domain containing phosphatase anchor protein 1a), SPAP1B, SPAP1C, Genbank accession no. NM_030764, AY358130) Genome Res. 13 (10):2265-2270 (2003), Immunogenetics 54 (2):87-95 (2002), Blood 99 (8):2662-2669 (2002), Proc. Natl. Acad. Sci. U.S.A. 98 (17):9772-9777 (2001), Xu, M. J., et al. (2001) Biochem. Biophys. Res. Commun. 280 (3):768-775; WO2004016225 (Claim 2); WO2003077836; WO200138490 (Claim 5; FIG. 18D-1-18D-2); WO2003097803 (Claim 12); WO2003089624 (Claim 25); Cross-references: MIM:606509; NP_110391.2; NM_030764_1.

Figure 1B:
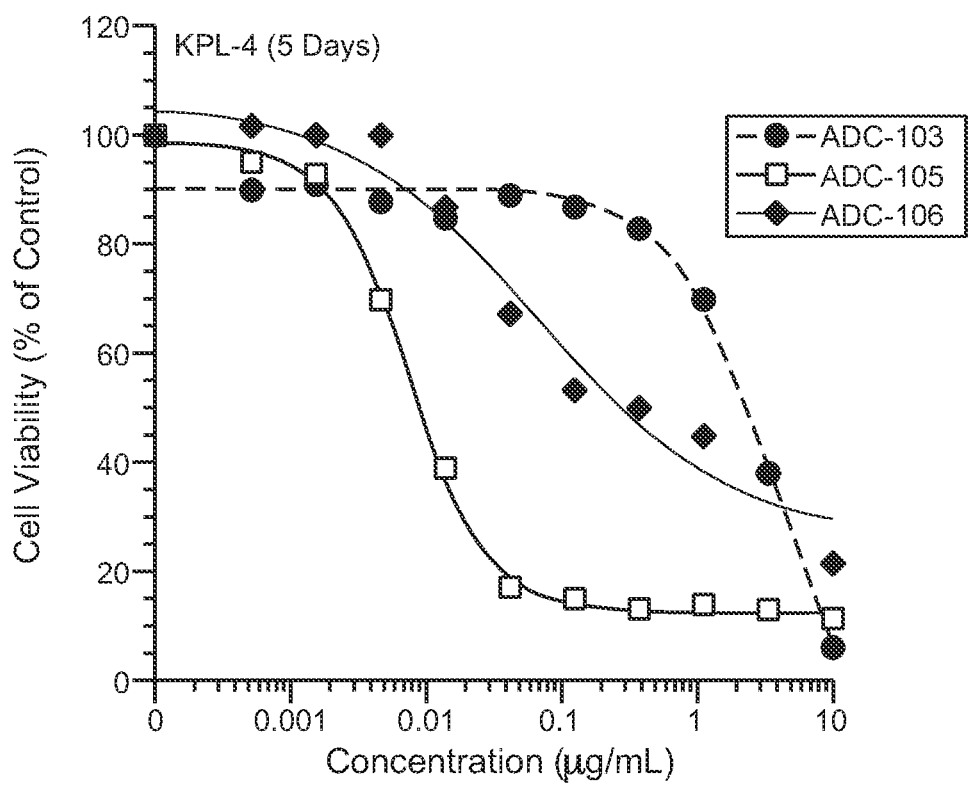
FIG. 1B shows a plot of in vitro cell viability of KPL-4 cells treated with Thio anti-Her2 7C2 LC-K149C-MC-vc-PAB-Silvestrol-amine, ADC-103, Thio Hu Anti-CD22 10F4v3 HC:A140C amino silvestrol analog, ADC-105, non-target control, and Thio Hu Anti-Her2 7C2 HC:A140C amino silvestrol analog, ADC-106.
Figure 1C:
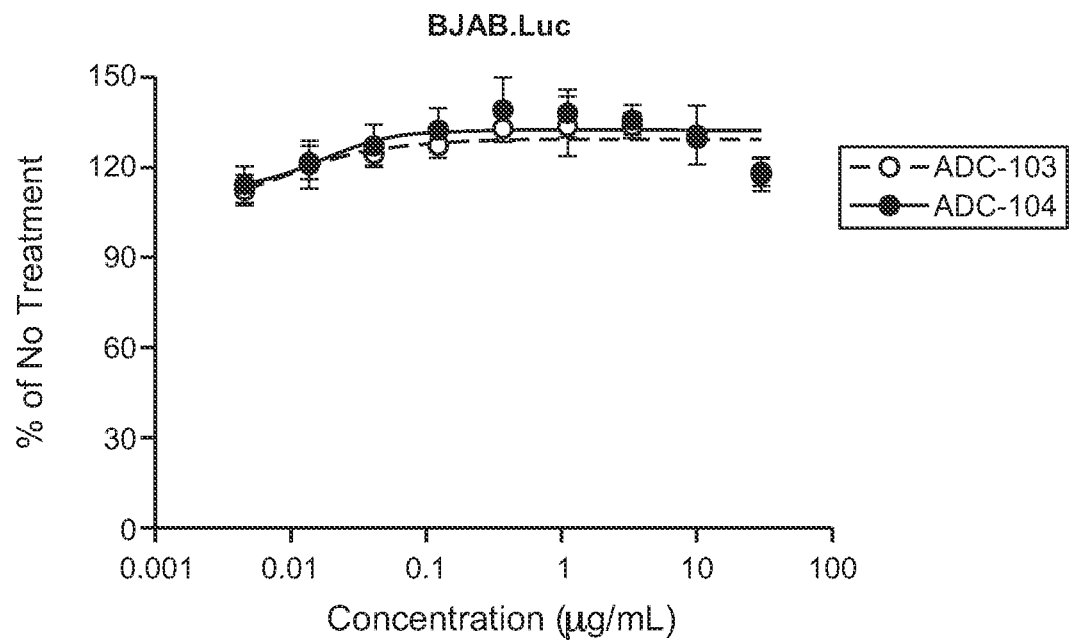
FIG. 1C shows a plot of in vitro cell viability of Bjab-luc cells treated with Thio anti-Her2 7C2 LC-K149C-MC-vc-PAB-Silvestrol-amine, ADC-103, and Thio anti-CD22 LC-K149C-MC-vc-PAB-Silvestrol-amine, 6 mg/kg IV once, ADC-104.
Figure 1D:
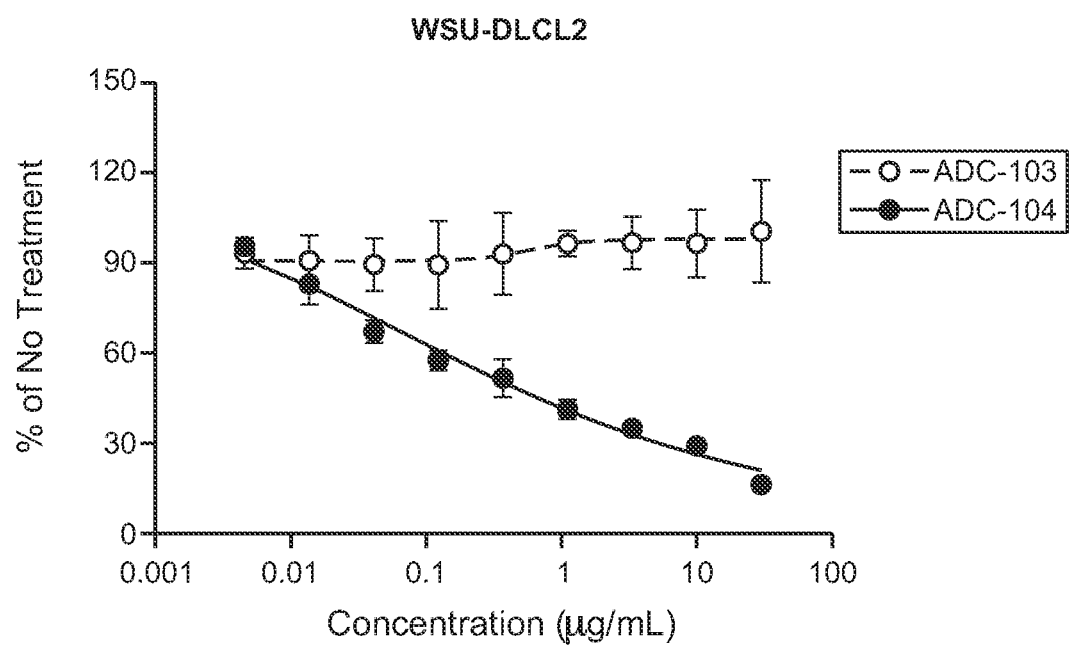
FIG. 1D shows a plot of in vitro cell viability of WSU-DLCL2 cells treated with Thio anti-Her2 7C2 LC-K149C-MC-vc-PAB-Silvestrol-amine, ADC-103, and Thio anti-CD22 LC-K149C-MC-vc-PAB-Silvestrol-amine, ADC-104, 6 mg/kg IV once.

(17) HER2 (ErbB2, Genbank accession no. M11730) Coussens L., et al. Science (1985) 230(4730):1132-1139); Yamamoto T., et al. Nature 319, 230-234, 1986; Semba K., et al. Proc. Natl. Acad. Sci. U.S.A. 82, 6497-6501, 1985; Swiercz J. M., et al. J. Cell Biol. 165, 869-880, 2004; Kuhns J. J., et al. J. Biol. Chem. 274, 36422-36427, 1999; Cho H.-S., et al. Nature 421, 756-760, 2003; Ehsani A., et al. (1993) Genomics 15, 426-429; WO2004048938 (Example 2); WO2004027049 (FIG. 1I); WO2004009622; WO2003081210; WO2003089904 (Claim 9); WO2003016475 (Claim 1); US2003118592; WO2003008537 (Claim 1); WO2003055439 (Claim 29; FIG. 1A-B); WO2003025228 (Claim 37; FIG. 5C); WO200222636 (Example 13; Page 95-107); WO200212341 (Claim 68; FIG. 7); WO200213847 (Page 71-74); WO200214503 (Page 114-117); WO200153463 (Claim 2; Page 41-46); WO200141787 (Page 15); WO200044899 (Claim 52; FIG. 7); WO200020579 (Claim 3; FIG. 2); U.S. Pat. No. 5,869,445 (Claim 3; Col 31-38); WO9630514 (Claim 2; Page 56-61); EP1439393 (Claim 7); WO2004043361 (Claim 7); WO2004022709; WO200100244 (Example 3; FIG. 4); Accession: P04626; EMBL; M11767; AAA35808.1. EMBL; M11761; AAA35808.1.

(18) NCA (CEACAM6, Genbank accession no. M18728); Barnett T., et al. Genomics 3, 59-66, 1988; Tawaragi Y., et al. Biochem. Biophys. Res. Commun. 150, 89-96, 1988; Strausberg R. L., et al. Proc. Natl. Acad. Sci. U.S.A. 99:16899-16903, 2002; WO2004063709; EP1439393 (Claim 7); WO2004044178 (Example 4); WO2004031238; WO2003042661 (Claim 12); WO200278524 (Example 2); WO200286443 (Claim 27; Page 427); WO200260317 (Claim 2); Accession: P40199; Q14920; EMBL; M29541; AAA59915.1. EMBL; M18728.

(19) MDP (DPEP1, Genbank accession no. BC017023) Proc. Natl. Acad. Sci. U.S.A. 99 (26):16899-16903 (2002)); WO2003016475 (Claim 1); WO200264798 (Claim 33; Page 85-87); JP05003790 (FIG. 6-8); WO9946284 (FIG. 9); Cross-references: MIM:179780; AAH17023.1; BC017023_1.

(20) IL20Rα (IL20Ra, ZCYTOR7, Genbank accession no. AF184971); Clark H. F., et al. Genome Res. 13, 2265-2270, 2003; Mungall A. J., et al. Nature 425, 805-811, 2003; Blumberg H., et al. Cell 104, 9-19, 2001; Dumoutier L., et al. J. Immunol. 167, 3545-3549, 2001; Parrish-Novak J., et al. J. Biol. Chem. 277, 47517-47523, 2002; Pletnev S., et al. (2003) Biochemistry 42:12617-12624; Sheikh F., et al. (2004) J. Immunol. 172, 2006-2010; EP1394274 (Example 11); US2004005320 (Example 5); WO2003029262 (Page 74-75); WO2003002717 (Claim 2; Page 63); WO200222153 (Page 45-47); US2002042366 (Page 20-21); WO200146261 (Page 57-59); WO200146232 (Page 63-65); WO9837193 (Claim 1; Page 55-59); Accession: Q9UHF4; Q6UWA9; Q96SH8; EMBL; AF184971; AAF01320.1.

(21) Brevican (BCAN, BEHAB, Genbank accession no. AF229053) Gary S. C., et al. Gene 256, 139-147, 2000; Clark H. F., et al. Genome Res. 13, 2265-2270, 2003; Strausberg R. L., et al. Proc. Natl. Acad. Sci. U.S.A. 99, 16899-16903, 2002; US2003186372 (Claim 11); US2003186373 (Claim 11); US2003119131 (Claim 1; FIG. 52); US2003119122 (Claim 1; FIG. 52); US2003119126 (Claim 1); US2003119121 (Claim 1; FIG. 52); US2003119129 (Claim 1); US2003119130 (Claim 1); US2003119128 (Claim 1; FIG. 52); US2003119125 (Claim 1); WO2003016475 (Claim 1); WO200202634 (Claim 1).

(22) EphB2R (DRT, ERK, Hek5, EPHT3, Tyro5, Genbank accession no. NM_004442) Chan, J. and Watt, V. M., Oncogene 6 (6), 1057-1061 (1991) Oncogene 10 (5):897-905 (1995), Annu. Rev. Neurosci. 21:309-345 (1998), Int. Rev. Cytol. 196:177-244 (2000)); WO2003042661 (Claim 12); WO200053216 (Claim 1; Page 41); WO2004065576 (Claim 1); WO2004020583 (Claim 9); WO2003004529 (Page 128-132); WO200053216 (Claim 1; Page 42); Cross-references: MIM:600997; NP_004433.2; NM_004442_1.

(23) ASLG659 (B7h, Genbank accession no. AX092328) US20040101899 (Claim 2); WO2003104399 (Claim 11); WO2004000221 (FIG. 3); US2003165504 (Claim 1); US2003124140 (Example 2); US2003065143 (FIG. 60); WO2002102235 (Claim 13; Page 299); US2003091580 (Example 2); WO200210187 (Claim 6; FIG. 10); WO200194641 (Claim 12; FIG. 7b); WO200202624 (Claim 13; FIG. 1A-1B); US2002034749 (Claim 54; Page 45-46); WO200206317 (Example 2; Page 320-321, Claim 34; Page 321-322); WO200271928 (Page 468-469); WO200202587 (Example 1; FIG. 1); WO200140269 (Example 3; Pages 190-192); WO200036107 (Example 2; Page 205-207); WO2004053079 (Claim 12); WO2003004989 (Claim 1); WO200271928 (Page 233-234, 452-453); WO 0116318.

(24) PSCA (Prostate stem cell antigen precursor, Genbank accession no. AJ297436) Reiter R. E., et al. Proc. Natl. Acad. Sci. U.S.A. 95, 1735-1740, 1998; Gu Z., et al. Oncogene 19, 1288-1296, 2000; Biochem. Biophys. Res. Commun. (2000) 275(3):783-788; WO2004022709; EP1394274 (Example 11); US2004018553 (Claim 17); WO2003008537 (Claim 1); WO200281646 (Claim 1; Page 164); WO 2003003906 (Claim 10; Page 288); WO 200140309 (Example 1; FIG. 17); US 2001055751 (Example 1; FIG. 1b); WO 200032752 (Claim 18; FIG. 1); WO 1998/51805 (Claim 17; Page 97); WO 1998/51824 (Claim 10; Page 94); WO 1998/40403 (Claim 2; FIG. 1B); Accession: O43653; EMBL; AF043498; AAC39607.1.

(25) GEDA (Genbank accession No. AY260763); AAP14954 lipoma HMGIC fusion-partner-like protein/pid=AAP14954.1—*Homo sapiens* Species: *Homo sapiens* (human) WO2003054152 (Claim 20); WO2003000842 (Claim 1); WO2003023013 (Example 3, Claim 20); US2003194704 (Claim 45); Cross-references: GI:30102449; AAP14954.1; AY260763_1.

(26) BAFF-R (B cell-activating factor receptor, BLyS receptor 3, BR3, Genbank accession No. AF116456); BAFF receptor/pid=NP_443177.1—*Homo sapiens* Thompson, J. S., et al. Science 293 (5537), 2108-2111 (2001); WO2004058309; WO2004011611; WO2003045422 (Example; Page 32-33); WO2003014294 (Claim 35; FIG. 6B); WO2003035846 (Claim 70; Page 615-616); WO200294852 (Col 136-137); WO200238766 (Claim 3; Page 133); WO200224909 (Example 3; FIG. 3); Cross-references: MIM:606269; NP_443177.1; NM_052945 1; AF132600.

(27) CD22 (B-cell receptor CD22-B isoform, BL-CAM, Lyb-8, Lyb8, SIGLEC-2, FLJ22814, Genbank accession No. AK026467); Wilson et al. (1991) J. Exp. Med. 173:137-146; WO2003072036 (Claim 1; FIG. 1); Cross-references: MIM: 107266; NP_001762.1; NM_001771_1.

(28) CD79a (CD79A, CD79α, immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q13.2, Genbank accession No. NP_001774.10) WO2003088808, US20030228319; WO2003062401 (Claim 9); US2002150573 (Claim 4, pages 13-14); WO9958658 (Claim 13, FIG. 16); WO9207574 (FIG. 1); U.S. Pat. No. 5,644,033; Ha et al. (1992) J. Immunol. 148(5):1526-1531; Mueller et al. (1992) Eur. J. Biochem. 22:1621-1625; Hashimoto et al. (1994) Immunogenetics 40(4):287-295; Preud'homme et al. (1992) Clin. Exp. Immunol. 90(1):141-146; Yu et al. (1992) J. Immunol. 148(2) 633-637; Sakaguchi et al. (1988) EMBO J. 7(11): 3457-3464.

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pI: 8.54 MW: 41959 TM: 7 [P] Gene Chromosome: 11q23.3, Genbank accession No. NP_001707.1) WO 2004040000; WO2004/015426; US2003105292 (Example 2); U.S. Pat. No. 6,555,339 (Example 2); WO 2002/61087 (FIG. 1); WO200157188 (Claim 20, page 269); WO200172830 (pages 12-13); WO 2000/22129 (Example 1, pages 152-153, Example 2, pages 254-256); WO 199928468 (Claim 1, page 38); U.S. Pat. No. 5,440,021 (Example 2, col 49-52); WO9428931 (pages 56-58); WO 1992/17497 (Claim 7, FIG. 5); Dobner et al. (1992) Eur. J. Immunol. 22:2795-2799; Barella et al. (1995) Biochem. J. 309:773-779.

(30) HLA-DOB (Beta subunit of MHC class II molecule (Ia antigen) that binds peptides and presents them to CD4+ T lymphocytes); 273 aa, pI: 6.56 MW: 30820 TM: 1 [P] Gene Chromosome: 6p21.3, Genbank accession No.

NP_002111.1) Tonnelle et al. (1985) EMBO J. 4(11):2839-2847; Jonsson et al. (1989) Immunogenetics 29(6):411-413; Beck et al. (1992) J. Mol. Biol. 228:433-441; Strausberg et al. (2002) Proc. Natl. Acad. Sci USA 99:16899-16903; Servenius et al. (1987) J. Biol. Chem. 262:8759-8766; Beck et al. (1996) J. Mol. Biol. 255:1-13; Naruse et al. (2002) Tissue Antigens 59:512-519; WO9958658 (Claim 13, FIG. 15); U.S. Pat. No. 6,153,408 (Col 35-38); U.S. Pat. No. 5,976,551 (col 168-170); U.S. Pat. No. 6,011,146 (col 145-146); Kasahara et al. (1989) Immunogenetics 30(1):66-68; Larhammar et al. (1985) J. Biol. Chem. 260(26):14111-14119.

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa), pI: 7.63, MW: 47206 TM: 1 [P] Gene Chromosome: 17p13.3, Genbank accession No. NP_002552.2) Le et al. (1997) FEBS Lett. 418(1-2):195-199; WO2004047749; WO2003072035 (Claim 10); Touchman et al. (2000) Genome Res. 10:165-173; WO200222660 (Claim 20); WO2003093444 (Claim 1); WO2003087768 (Claim 1); WO2003029277 (page 82).

(32) CD72 (B-cell differentiation antigen CD72, Lyb-2), pI: 8.66, MW: 40225 TM: 1 [P] Gene Chromosome: 9p13.3, Genbank accession No. NP_001773.1) WO2004042346 (Claim 65); WO 2003/026493 (pages 51-52, 57-58); WO 2000/75655 (pages 105-106); Von Hoegen et al. (1990) J. Immunol. 144(12):4870-4877; Strausberg et al. (2002) Proc. Natl. Acad. Sci USA 99:16899-16903.

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis); 661 aa, pI: 6.20, MW: 74147 TM: 1 [P] Gene Chromosome: 5q12, Genbank accession No. NP_005573.1) US2002193567; WO9707198 (Claim 11, pages 39-42); Miura et al. (1996) Genomics 38(3):299-304; Miura et al. (1998) Blood 92:2815-2822; WO2003083047; WO9744452 (Claim 8, pages 57-61); WO200012130 (pages 24-26).

(34) FcRH1 (Fc receptor-like protein 1, a putative receptor for the immunoglobulin Fc domain that contains C2 type Ig-like and ITAM domains, may have a role in B-lymphocyte differentiation); 429 aa, pI: 5.28, MW: 46925 TM: 1 [P] Gene Chromosome: 1q21-1q22, Genbank accession No. NP_443170.1) WO2003077836; WO200138490 (Claim 6, FIG. 18E-1-18-E-2); Davis et al. (2001) Proc. Natl. Acad. Sci USA 98(17):9772-9777; WO2003089624 (Claim 8); EP1347046 (Claim 1); WO2003089624 (Claim 7).

(35) IRTA2 (Immunoglobulin superfamily receptor translocation associated 2, a putative immunoreceptor with possible roles in B cell development and lymphomagenesis; deregulation of the gene by translocation occurs in some B cell malignancies); 977 aa, pI: 6.88 MW: 106468 TM: 1 [P] Gene Chromosome: 1q21, Genbank accession No. Human: AF343662, AF343663, AF343664, AF343665, AF369794, AF397453, AK090423, AK090475, AL834187, AY358085; Mouse:AK089756, AY158090, AY506558; NP_112571.1. WO2003024392 (Claim 2, FIG. 97); Nakayama et al. (2000) Biochem. Biophys. Res. Commun. 277(1):124-127; WO2003077836; WO200138490 (Claim 3, FIG. 18B-1-18B-2).

(36) TENB2 (TMEFF2, tomoregulin, TPEF, HPP1, TR, putative transmembrane proteoglycan, related to the EGF/ heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; Genbank accession No. AF179274; AY358907, CAF85723, CQ782436 WO 2004074320; JP 2004113151; WO 2003042661; WO2003009814; EP1295944 (pages 69-70); WO 200230268 (page 329); WO 200190304; US2004249130; US 2004022727; WO 2004063355; US 2004197325; US2003232350; US2004005563; US 2003124579; Horie et al. (2000) Genomics 67:146-152; Uchida et al. (1999) Biochem. Biophys. Res. Commun. 266:593-602; Liang et al. (2000) Cancer Res. 60:4907-12; Glynne-Jones et al. (2001) Int J Cancer. October 15; 94(2):178-84.

(37) PMEL17 (silver homolog: SILV; D12S53E; PMEL17; SI; SIL); ME20; gp100) BC001414; BT007202; M32295; M77348; NM_006928; McGlinchey, R. P. et al. (2009) Proc. Natl. Acad. Sci. U.S.A. 106 (33), 13731-13736; Kummer, M. P. et al. (2009) J. Biol. Chem. 284 (4), 2296-2306.

(38) TMEFF1 (transmembrane protein with EGF-like and two follistatin-like domains 1; Tomoregulin-1); H7365; C9orf2; C9ORF2; U19878; X83961; NM_080655; NM_003692; Harms, P. W. (2003) Genes Dev. 17 (21), 2624-2629; Gery, S. et al. (2003) Oncogene 22 (18):2723-2727.

(39) GDNF-Ra1 (GDNF family receptor alpha 1; GFRA1; GDNFR; GDNFRA; RETL1; TRNR1; RET1L; GDNFR-alpha1; GFR-ALPHA-1); U95847; BC014962; NM_145793 NM_005264; Kim, M. H. et al. (2009) Mol. Cell. Biol. 29 (8), 2264-2277; Treanor, J. J. et al. (1996) Nature 382 (6586):80-83.

(40) Ly6E (lymphocyte antigen 6 complex, locus E; Ly67,RIG-E, SCA-2, TSA-1); NP_002337.1; NM_002346.2; de Nooij-van Dalen, A. G. et al. (2003) Int. J. Cancer 103 (6), 768-774; Zammit, D. J. et al. (2002) Mol. Cell. Biol. 22 (3):946-952.

(41) TMEM46 (shisa homolog 2 (*Xenopus laevis*); SHISA2); NP_001007539.1; NM_001007538.1; Furushima, K. et al. (2007) Dev. Biol. 306 (2), 480-492; Clark, H. F. et al. (2003) Genome Res. 13 (10):2265-2270.

(42) Ly6G6D (lymphocyte antigen 6 complex, locus G6D; Ly6-D, MEGT1); NP_067079.2; NM_021246.2; Mallya, M. et al. (2002) Genomics 80 (1):113-123; Ribas, G. et al. (1999) J. Immunol. 163 (1):278-287.

(43) LGR5 (leucine-rich repeat-containing G protein-coupled receptor 5; GPR49, GPR67); NP_003658.1; NM_003667.2; Salanti, G. et al. (2009) Am. J. Epidemiol. 170 (5):537-545; Yamamoto, Y. et al. (2003) Hepatology 37 (3):528-533.

(44) RET (ret proto-oncogene; MEN2A; HSCR1; MEN2B; MTC1; PTC; CDHF12; Hs.168114; RET51; RET-ELE1); NP_066124.1; NM_020975.4; Tsukamoto, H. et al. (2009) Cancer Sci. 100 (10):1895-1901; Narita, N. et al. (2009) Oncogene 28 (34):3058-3068.

(45) LY6K (lymphocyte antigen 6 complex, locus K; LY6K; HSJ001348; FLJ35226); NP_059997.3; NM_017527.3; Ishikawa, N. et al. (2007) Cancer Res. 67 (24):11601-11611; de Nooij-van Dalen, A. G. et al. (2003) Int. J. Cancer 103 (6):768-774.

(46) GPR19 (G protein-coupled receptor 19; Mm.4787); NP_006134.1; NM_006143.2; Montpetit, A. and Sinnett, D. (1999) Hum. Genet. 105 (1-2):162-164; O'Dowd, B. F. et al. (1996) FEBS Lett. 394 (3):325-329.

(47) GPR54 (KISS1 receptor; KISS1R; GPR54; HOT7T175; AXOR12); NP_115940.2; NM_032551.4; Navenot, J. M. et al. (2009) Mol. Pharmacol. 75 (6):1300-1306; Hata, K. et al. (2009) Anticancer Res. 29 (2):617-623.

(48) ASPHD1 (aspartate beta-hydroxylase domain containing 1; LOC253982); NP_859069.2; NM_181718.3; Gerhard, D. S. et al. (2004) Genome Res. 14 (10B):2121-2127.

(49) Tyrosinase (TYR; OCAIA; OCA1A; tyrosinase; SHEP3); NP_000363.1; NM_000372.4; Bishop, D. T. et al. (2009) Nat. Genet. 41 (8):920-925; Nan, H. et al. (2009) Int. J. Cancer 125 (4):909-917.

(50) TMEM118 (ring finger protein, transmembrane 2; RNFT2; FLJ14627); NP_001103373.1; NM_001109903.1; Clark, H. F. et al. (2003) Genome Res. 13 (10):2265-2270; Scherer, S. E. et al. (2006) Nature 440 (7082):346-351.

(51) GPR172A (G protein-coupled receptor 172A; GPCR41; FLJ11856; D15Ertd747e); NP_078807.1; NM_024531.3; Ericsson, T. A. et al. (2003) Proc. Natl. Acad. Sci. U.S.A. 100 (11):6759-6764; Takeda, S. et al. (2002) FEBS Lett. 520 (1-3):97-101.

(52) CD33, a member of the sialic acid binding, immunoglobulin-like lectin family, is a 67-kDa glycosylated transmembrane protein. CD33is expressed on most myeloid and monocytic leukemia cells in addition to committed myelomonocytic and erythroid progenitor cells. It is not seen on the earliest pluripotent stem cells, mature granulocytes, lymphoid cells, or nonhematopoietic cells (Sabbath et al., (1985) *J. Clin. Invest.* 75:756-56; Andrews et al., (1986) *Blood* 68:1030-5). CD33 contains two tyrosine residues on its cytoplasmic tail, each of which is followed by hydrophobic residues similar to the immunoreceptor tyrosine-based inhibitory motif (ITIM) seen in many inhibitory receptors.

(53) CLL-1 (CLEC12A, MICL, and DCAL2), encodes a member of the C-type lectin/C-type lectin-like domain (CTL/CTLD) superfamily. Members of this family share a common protein fold and have diverse functions, such as cell adhesion, cell-cell signaling, glycoprotein turnover, and roles in inflammation and immune response. The protein encoded by this gene is a negative regulator of granulocyte and monocyte function. Several alternatively spliced transcript variants of this gene have been described, but the full-length nature of some of these variants has not been determined. This gene is closely linked to other CTL/CTLD superfamily members in the natural killer gene complex region on chromosome 12p13 (Drickamer K (1999) Curr. Opin. Struct. Biol. 9 (5):585-90; van Rhenen A, et al., (2007) Blood 110 (7):2659-66; Chen C H, et al. (2006) Blood 107 (4):1459-67; Marshall A S, et al. (2006) Eur. J. Immunol. 36 (8):2159-69; Bakker A B, et al. (2005) Cancer Res. 64 (22):8443-50; Marshall A S, et al. (2004) J. Biol. Chem. 279 (15):14792-802). CLL-1 has been shown to be a type II transmembrane receptor comprising a single C-type lectin-like domain (which is not predicted to bind either calcium or sugar), a stalk region, a transmembrane domain and a short cytoplasmic tail containing an ITIM motif.

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

Antibodies may be produced using recombinant methods and compositions, e.g., as described in U.S. Pat. No. 4,816,567. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell).

For recombinant production of an antibody, nucleic acid encoding an antibody, e.g., as described herein, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology, Vol.* 248 (B. K. C. Lo, ed., Humana Press, Totowa, N.J., 2003), pp. 245-254, describing expression of antibody fragments in *E. coli*) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177; 6,040,498; 6,420,548; 7,125,978; 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TM cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR$^-$ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, N.J.), pp. 255-268 (2003).

Linkers

A "Linker" (L) is a bifunctional or multifunctional moiety that can be used to link one or more silvestrol drug moieties to an antibody (Ab) to form an antibody-drug conjugate (ADC) of Formulas IIa and IIb. In some embodiments, antibody-drug conjugates (ADC) can be prepared using a Linker having reactive functionalities for covalently attaching to the drug and to the antibody. For example, in some embodiments, a cysteine thiol of an antibody (Ab) can form a bond with a reactive functional group of a linker or a drug-linker intermediate to make an ADC.

In one aspect, a linker has a functionality that is capable of reacting with a free cysteine present on an antibody to form a covalent bond. Nonlimiting exemplary such reactive functionalities include maleimide, haloacetamides, α-haloacetyl, pyridyl disulfide, activated esters such as succinimide esters, N-hydroxysuccinimide, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al (2004), *Bioconjugate Chemistry* 15(4):765-773, and the Examples herein.

In some embodiments, a linker has a functionality that is capable of reacting with an electrophilic group present on an antibody. Exemplary such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting exemplary reactive functionalities include, but are not limited to, hydrazide, oxime, amino, hydrazine, thiosemicarbazone, hydrazine carboxylate, and arylhydrazide.

A linker may comprise one or more linker components, including but not limited to, a stretcher unit, a peptidomimetic unit, a peptide unit, and a spacer unit. Exemplary linker components include 6-maleimidocaproyl ("MC"), maleimidopropanoyl ("MP"), valine-citrulline ("val-cit" or "vc"), alanine-phenylalanine ("ala-phe"), phenylalanine-lysine (phe-lys), p-aminobenzyloxycarbonyl (a "PAB"), N-Succinimidyl 4-(2-pyridylthio) pentanoate ("SPP"), and 4-(N-maleimidomethyl) cyclohexane-1 carboxylate ("MCC"). Various linker components are known in the art, some of which are described below.

A linker may be a "cleavable linker," facilitating release of a drug. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., Cancer Research 52:127-131 (1992); U.S. Pat. No. 5,208,020).

Exemplary embodiments of linkers are described in U.S. Pat. No. 7,498,298, which is expressly incorporated herein by reference.

Silvestrol Drug-Linker Intermediate Compounds

Silvestrol (CAS Reg. No. 697235-38-4), named as methyl (1R,2R,3S,3aR,8bS)-6-(((2S,3R,6R)-6-((R)-1,2-dihydroxyethyl)-3-methoxy-1,4-dioxan-2-yl)oxy)-1,8b-dihydroxy-8-methoxy-3a-(4-methoxyphenyl)-3-phenyl-2,3,3a,8b-tetrahydro-1H-cyclopenta[b]benzofuran-2-carboxylate (compound 16, Example 1a), is a rocaglate derivative isolated from *Aglaia foveolata* (Pan, L., et al (2014) Nat. Prod. Rep. 31:924-939) and regulates G2/M checkpoint genes independent of p53 activity (Mi, Q. et al (2006) Anticancer Res. 26(5A):3349-56). Silvestrol and analogs are potent and selective protein synthesis inhibitors and have been studied for their anti-hyperproliferative properties (Liu, T. et al (2012) Journal of Medicinal Chemistry, 55(20):8859-8878; WO 2015/085221; WO 2013016658; WO 2004041812; U.S. Pat. Nos. 8,137,509; 8,404,088; WO 2006007634; U.S. Pat. No. 7,816,544). Silvestrol has the structure:

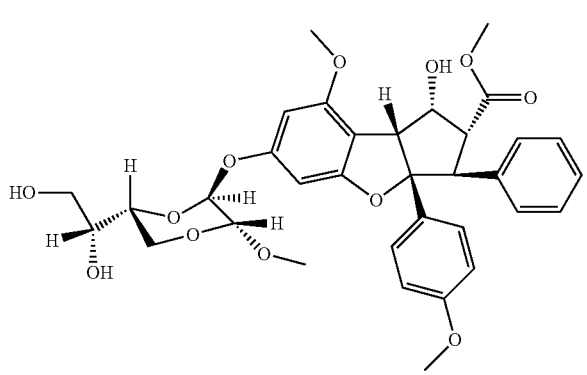

Silvestrol-linker intermediates of Formula II are prepared according to the procedures of the Examples.

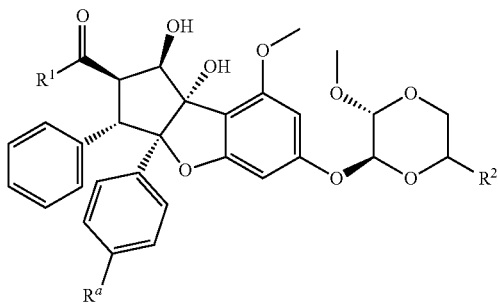

II wherein

R$^a$ is a group selected from CH$_3$O, CN, NO$_2$, and Cl;
R$^1$ is selected from —OCH$_3$ and L-X; and
R$^2$ is selected from —CH(OH)CH$_2$OH, and L-X
L is a linker; and
X comprises a reactive functional group selected from maleimide, thiol, amino, bromide, bromoacetamido, iodoacetamido, p-toluenesulfonate, iodide, hydroxyl, carboxyl, pyridyl disulfide, and N-hydroxysuccinimide.

In an exemplary embodiment, L-X is selected from —CH$_2$CH$_2$—X, —CH$_2$CR$_2$—X, —C(O)NRCH$_2$—X, —CH$_2$O—X, —CH$_2$N(R)—X, —N(R)—X, —N(R)(C$_1$-C$_{12}$ alkylene)-X, —N(R)(C$_2$-C$_8$ alkenylene)-X, —N(R)(C$_2$-C$_8$ alkynylene)-X, and —N(R)(CH$_2$CH$_2$O)$_n$—X;

n is 1 to 6;

R is independently selected from H, C$_1$-C$_{12}$ alkyl, and C$_6$-C$_{20}$ aryl; or two R form a C$_3$-C$_7$ carbocyclic ring; and alkylene, alkenylene, alkynylene, alkyl, and aryl are optionally substituted with one or more groups selected from F, Cl, Br, N(CH$_3$)$_2$, NO$_2$, and OCH$_3$.

In an exemplary embodiment, alkylene is selected from —CH$_2$CH$_2$—, —CH$_2$CH$_2$CH$_2$—, —CH(CH$_3$)CH$_2$—, and —C(CH$_3$)$_2$CH$_2$—.

In an exemplary embodiment, X is selected from:

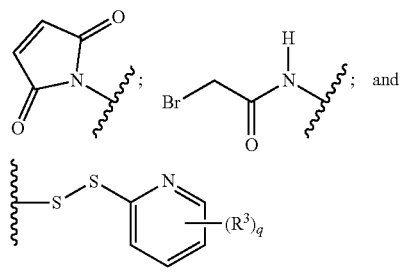

where the wavy lines indicate the attachments to L; and R$^3$ is NO$_2$, Cl, F, CN or Br, and q is 0, 1, or 2.

In an exemplary embodiment, R$^1$ is —OCH$_3$ and R$^2$ is L-X.

In an exemplary embodiment, R$^1$ is L-X and R$^2$ is —CH(OH)CH$_2$OH.

In an exemplary embodiment, L is a protease-cleavable, non-peptide linker having the formula:

-Str-PM-Y— where Str is a stretcher unit covalently attached to X; PM is a peptidomimetic unit, and Y is a spacer unit covalently attached to the silvestrol drug moiety.

Peptidomimetic linkers are described in WO 2015/095227, WO 2015/095124 or WO 2015/095223, which are hereby incorporated by reference in their entirety.

In an exemplary embodiment, Str is (CH$_2$)$_5$.

In an exemplary embodiment, PM has the formula:

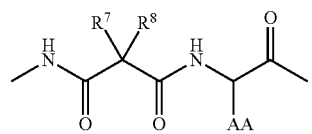

where R$^7$ and R$^8$ together form a C$_3$-C$_7$ cycloalkyl ring, and

AA is an amino acid side chain selected from H, —CH$_3$, —CH$_2$(C$_6$H$_5$), —CH$_2$CH$_2$CH$_2$CH$_2$NH$_2$, —CH$_2$CH$_2$CH$_2$NHC(NH)NH$_2$, —CHCH(CH$_3$)CH$_3$, and —CH$_2$CH$_2$CH$_2$NHC(O)NH$_2$.

In an exemplary embodiment, R$^7$ and R$^8$ together form cyclobutyl.

In an exemplary embodiment, Y comprises para-aminobenzyl or para-aminobenzyloxycarbonyl.

In an exemplary embodiment, L is a peptide linker having the formula:

-Str-Pep-Y— where Str is a stretcher unit covalently attached to the antibody; Pep is a peptide of two to twelve amino acid residues, and Y is a spacer unit covalently attached to the silvestrol drug moiety.

In an exemplary embodiment, Str is (CH$_2$)$_5$.

In some embodiments, Str include the following wherein the wavy line indicates sites of covalent attachment to the antibody, drug, or additional linker components:

MC

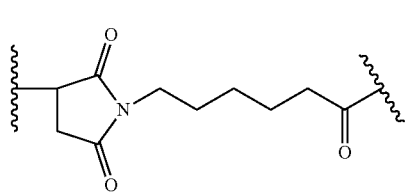

MP

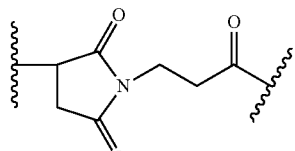

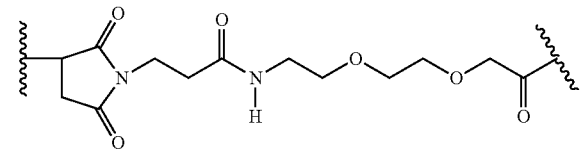

mPEG

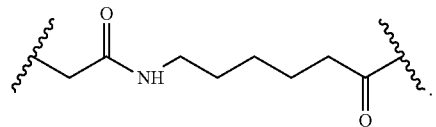

In an exemplary embodiment, Pep comprises two amino acid residues independently selected from glycine, alanine, phenylalanine, lysine, arginine, valine, and citrulline.

In an exemplary embodiment, the silvestrol-linker intermediate compound is selected from the compounds of Table 5.

Silvestrol-linker intermediate compounds (LD) may be purified and isolated according to conventional methods and Examples 1-3. Purification and isolation methods are known in the art and include precipitation, crystallization, filtration, centrifugation, ultrafiltration, and various chromatographic techniques. Chromatography can involve any number of methods including, e.g.: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography. In some such aspects, the completed reaction mixture may be evaporated to dryness followed by re-dissolution in a polar aprotic solvent. The solution may be filtered and then precipitated by combining the solution with a nonpolar antisolvent such as, for instance, hexane or cyclohexane. The precipitate may then be collected by filtration, optionally washed, and then dried.

TABLE 5

Silvestrol-Linker Intermediates

| LD No. | Structure |
|---|---|
| LD-51 | 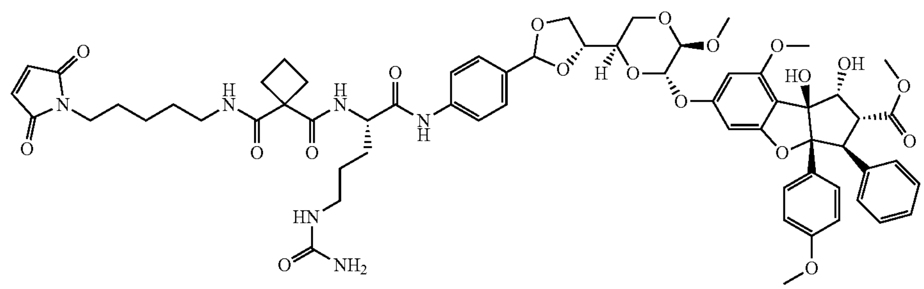 |
| LD-52 | 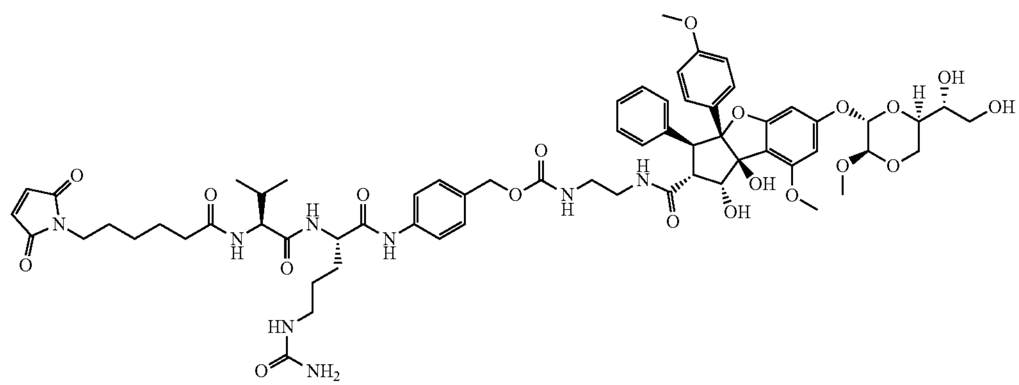 [SMILES: COc1ccc([C@@]23Oc4cc(O[C@@H]5O[C@@H]([C@H](O)CO)CO[C@H]5OC)cc(OC)c4[C@]2(O)[C@H](O)[C@H](C(=O)NCCNC(=O)OCc2ccc(NC(=O)[C@H](CCCNC(N)=O)NC(=O)[C@@H](NC(=O)CCCCCN4C(=O)C=CC4=O)C(C)C)cc2)[C@H]3c2ccccc2)cc1] |
| LD-53 | 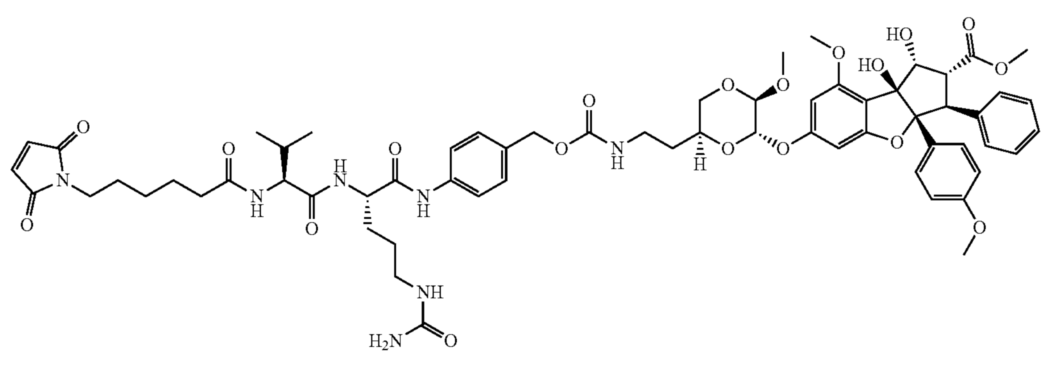 [SMILES: COC(=O)[C@H]1[C@@H](O)[C@@]2(O)c3c(OC)cc(O[C@@H]4O[C@@H](CCNC(=O)OCc5ccc(NC(=O)[C@H](CCCNC(N)=O)NC(=O)[C@@H](NC(=O)CCCCCN6C(=O)C=CC6=O)C(C)C)cc5)CO[C@H]4OC)cc3O[C@@]2(c2ccc(OC)cc2)[C@@H]1c1ccccc1] |

TABLE 5-continued

Silvestrol-Linker Intermediates

| LD No. | Structure |
| --- | --- |
| LD-54 | 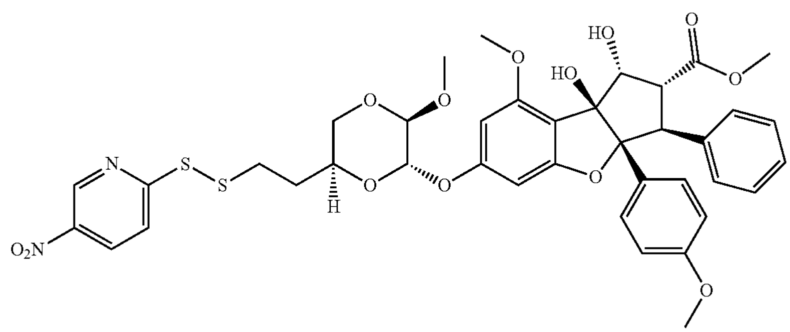 [SMILES: COC(=O)[C@H]1[C@@H](O)[C@@]2(O)c3c(OC)cc(O[C@@H]4O[C@@H](CCSSc5ccc([N+](=O)[O-])cn5)CO[C@H]4OC)cc3O[C@@]2(c2ccc(OC)cc2)[C@@H]1c1ccccc1] |
| LD-55 | 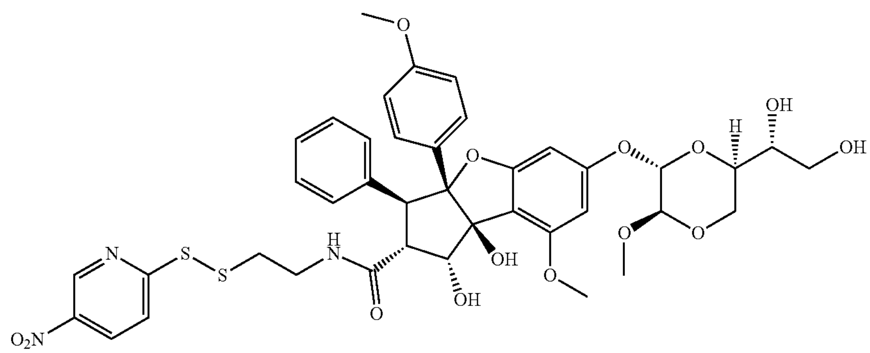 [SMILES: COc1ccc([C@@]23Oc4cc(O[C@@H]5O[C@@H]([C@H](O)CO)CO[C@H]5OC)cc(OC)c4[C@]2(O)[C@H](O)[C@H](C(=O)NCCSSc2ccc([N+](=O)[O-])cn2)[C@H]3c2ccccc2)cc1] |
| LD-56 | 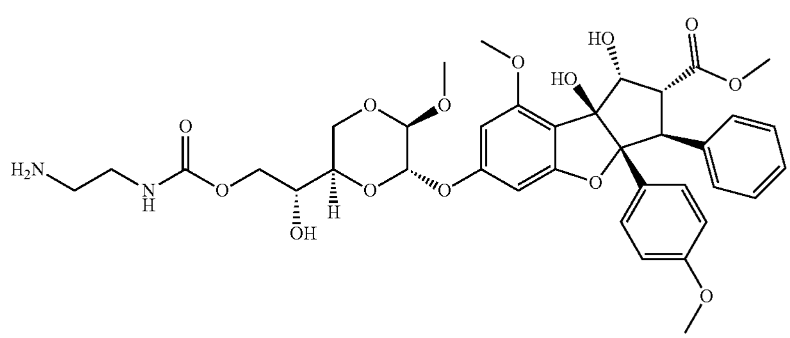 [SMILES: COC(=O)[C@H]1[C@@H](O)[C@@]2(O)c3c(OC)cc(O[C@@H]4O[C@@H]([C@H](O)COC(=O)NCCN)CO[C@H]4OC)cc3O[C@@]2(c2ccc(OC)cc2)[C@@H]1c1ccccc1] |
| LD-57 | 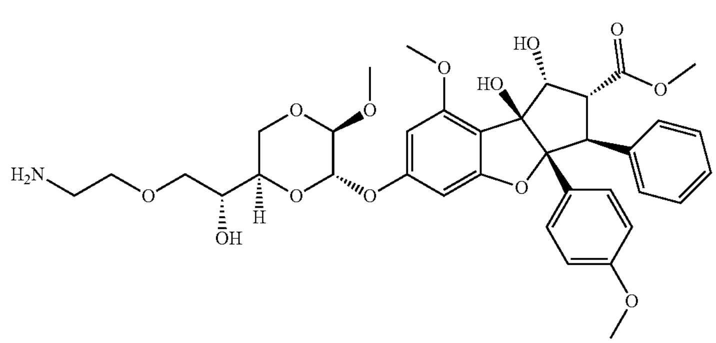 [SMILES: COC(=O)[C@H]1[C@@H](O)[C@@]2(O)c3c(OC)cc(O[C@@H]4O[C@@H]([C@H](O)COCCN)CO[C@H]4OC)cc3O[C@@]2(c2ccc(OC)cc2)[C@@H]1c1ccccc1] |

TABLE 5-continued

Silvestrol-Linker Intermediates

| LD No. | Structure |
|---|---|
| LD-58 | 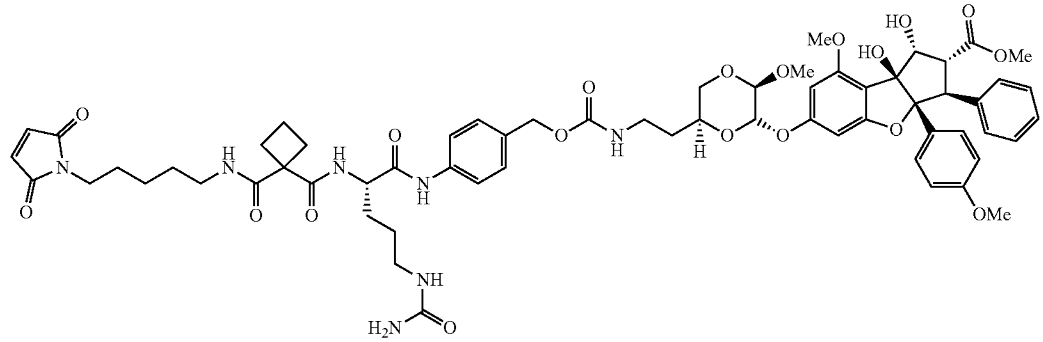 |
| LD-59 | 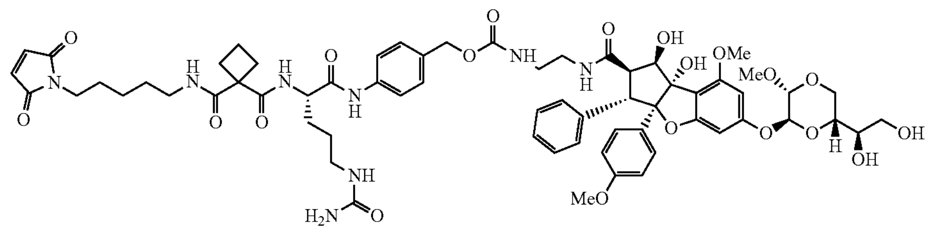 [SMILES: COc1ccc([C@@]23Oc4cc(O[C@@H]5O[C@@H]([C@H](O)CO)CO[C@H]5OC)cc(OC)c4[C@]2(O)[C@H](O)[C@H](C(=O)NCCNC(=O)OCc2ccc(NC(=O)[C@H](CCCNC(N)=O)NC(=O)C4(C(=O)NCCCCCN5C(=O)C=CC5=O)CCC4)cc2)[C@H]3c2ccccc2)cc1] |
| LD-60 | 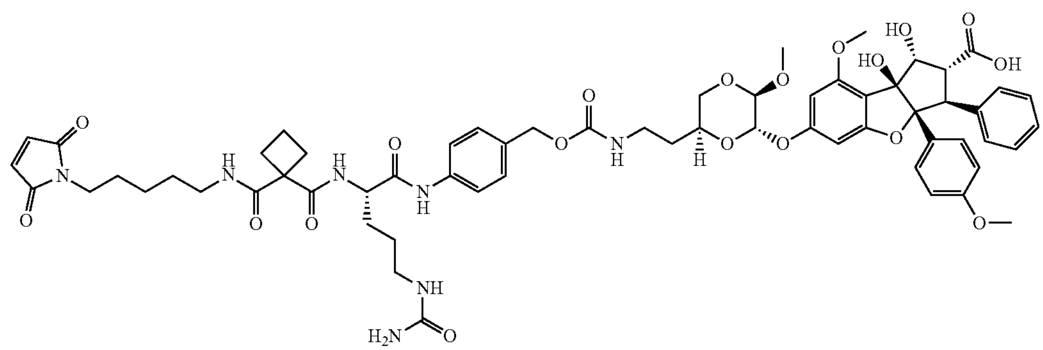 [SMILES: COc1ccc([C@@]23Oc4cc(O[C@@H]5O[C@@H](CCNC(=O)OCc6ccc(NC(=O)[C@H](CCCNC(N)=O)NC(=O)C7(C(=O)NCCCCCN8C(=O)C=CC8=O)CCC7)cc6)CO[C@H]5OC)cc(OC)c4[C@]2(O)[C@H](O)[C@H](C(=O)O)[C@H]3c2ccccc2)cc1] |

Antibody-Drug Conjugates

The invention provides antibody-drug conjugates having an antibody covalently attached through a linker to a silvestrol drug moiety, selected from Formulas Ia and Ib:

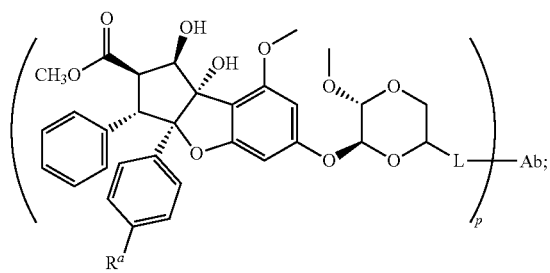
Ia

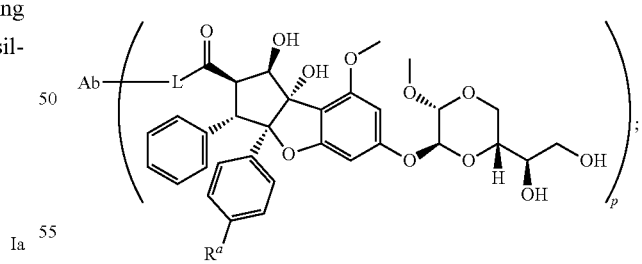
Ib or a pharmaceutically acceptable salt thereof, wherein
$R^a$ is a group selected from $CH_3O$, $CN$, $NO_2$, and $Cl$;
L is a linker;
p is an integer from 1 to 8; and
Ab is an antibody which binds to one or more tumor-associated antigens or cell-surface receptors.

In an exemplary embodiment, the antibody binds to one or more tumor-associated antigens or cell-surface receptors is selected from (1)-(53):

(1) BMPR1B (bone morphogenetic protein receptor-type IB);
(2) E16 (LAT1, SLC7A5);
(3) STEAP1 (six transmembrane epithelial antigen of prostate);
(4) MUC16 (0772P, CA125);
(5) MPF (MPF, MSLN, SMR, megakaryocyte potentiating factor, mesothelin);
(6) Napi2b (NAPI-3B, NPTIIb, SLC34A2, solute carrier family 34 (sodium phosphate), member 2, type II sodium-dependent phosphate transporter 3b);
(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B);
(8) PSCA hlg (2700050C12Rik, C530008016Rik, RIKEN cDNA 2700050C12, RIKEN cDNA 2700050C12 gene);
(9) ETBR (Endothelin type B receptor);
(10) MSG783 (RNF124, hypothetical protein FLJ20315);
(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein);
(12) TrpM4 (BR22450, FLJ20041, TRPM4, TRPM4B, transient receptor potential cation channel, subfamily M, member 4);
(13) CRIPTO (CR, CR1, CRGF, CRIPTO, TDGF1, teratocarcinoma-derived growth factor);
(14) CD21 (CR2 (Complement receptor 2) or C3DR (C3d/Epstein Barr virus receptor) or Hs 73792);
(15) CD79b (CD79B, CD79β, IGb (immunoglobulin-associated beta), B29);
(16) FcRH2 (IFGP4, IRTA4, SPAP1A (SH2 domain containing phosphatase anchor protein 1a), SPAP1B, SPAP1C);
(17) HER2;
(18) NCA;
(19) MDP;
(20) IL20Rα;
(21) Brevican;
(22) EphB2R;
(23) ASLG659;
(24) PSCA;
(25) GEDA;
(26) BAFF-R (B cell-activating factor receptor, BLyS receptor 3, BR3);
(27) CD22 (B-cell receptor CD22-B isoform);
(28) CD79a (CD79A, CD79α, immunoglobulin-associated alpha);
(29) CXCR5 (Burkitt's lymphoma receptor 1);
(30) HLA-DOB (Beta subunit of MHC class II molecule (Ia antigen));
(31) P2X5 (Purinergic receptor P2X ligand-gated ion channel 5);
(32) CD72 (B-cell differentiation antigen CD72, Lyb-2);
(33) LY64 (Lymphocyte antigen 64 (RP105), type I membrane protein of the leucine rich repeat (LRR) family);
(34) FcRH1 (Fc receptor-like protein 1);
(35) FcRH5 (IRTA2, Immunoglobulin superfamily receptor translocation associated 2);
(36) TENB2 (putative transmembrane proteoglycan);
(37) PMEL17 (silver homolog; SILV; D12S53E; PMEL17; SI; SIL);
(38) TMEFF1 (transmembrane protein with EGF-like and two follistatin-like domains 1; Tomoregulin-1);

(39) GDNF-Ra1 (GDNF family receptor alpha 1; GFRA1; GDNFR; GDNFRA; RETL1; TRNR1; RET1L; GDNFR-alpha1; GFR-ALPHA-1);
(40) Ly6E (lymphocyte antigen 6 complex, locus 1E; Ly67, RIG-E, SCA-2, TSA-1);
(41) TMEM46 (shisa homolog 2 (Xenopus laevis); SHISA2);
(42) Ly6G6D (lymphocyte antigen 6 complex, locus G6D; Ly6-D, MEGT1);
(43) LGR5 (leucine-rich repeat-containing G protein-coupled receptor GPR49, GPR67);
(44) RET (ret proto-oncogene; MEN2A; HSCR1; MEN2B; MTC1; PTC; CDHF12; Hs.168114; RET51; RET-ELE1);
(45) LY6K (lymphocyte antigen 6 complex, locus K.; LY6K; HSJ001348; FLJ35226);
(46) GPR19 (G protein-coupled receptor 19; Mm.4787);
(47) GPR54 (KISS1 receptor; KISS1R; GPR54; HOT7T175; AXOR12);
(48) ASPHD1 (aspartate beta-hydroxylase domain containing 1; LOC253982);
(49) Tyrosinase (TYR; OCAIA; OCA1A; tyrosinase; SHEP3);
(50) TMEM118 (ring finger protein, transmembrane 2; RNFT2; FLJ14627);
(51) GPR172A (G protein-coupled receptor 172A; GPCR41; FLJ11856; D15Ertd747e);
(52) CD33; and
(53) CLL-1.

In an exemplary embodiment, Ab is selected from anti-HER2 4D5, anti-CD22, anti-CD33, anti-Ly6E, anti-Napi3b, anti-HER2 7C2, and anti-CLL-1.

In an exemplary embodiment, Ab is a cysteine-engineered antibody.

In an exemplary embodiment, the cysteine-engineered antibody is a mutant selected from HC A118C, LC K149C, HC A140C, LC V205C, LC S121C, and HC L177C.

In an exemplary embodiment, L is a protease-cleavable, non-peptide linker having the formula:

-Str-PM-Y— where Str is a stretcher unit covalently attached to the antibody; PM is a peptidomimetic unit, and Y is a spacer unit covalently attached to the silvestrol drug moiety.

In an exemplary embodiment, Str has the formula:

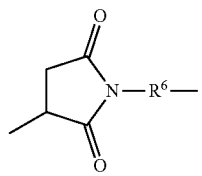

wherein $R^6$ is selected from the group consisting of $C_1$-$C_{12}$ alkylene, $C_1$-$C_{12}$ alkylene-C(═O), $C_1$-$C_{12}$ alkylene-NH, $(CH_2CH_2O)_r$, $(CH_2CH_2O)_r$—C(═O), $(CH_2CH_2O)_r$—$CH_2$, and $C_1$-$C_{12}$ alkylene-NHC(═O)$CH_2$CH(thiophen-3-yl), where r is an integer ranging from 1 to 10.

In an exemplary embodiment, $R^6$ is $(CH_2)_5$.

In an exemplary embodiment, PM has the formula:

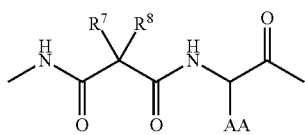

where $R^7$ and $R^8$ together form a $C_3$-$C_7$ cycloalkyl ring, and

AA is an amino acid side chain selected from H, —CH$_3$, —CH$_2$(C$_6$H$_5$), —CH$_2$CH$_2$CH$_2$CH$_2$NH$_2$, —CH$_2$CH$_2$CH$_2$NHC(NH)NH$_2$, —CHCH(CH$_3$)CH$_3$, and —CH$_2$CH$_2$CH$_2$NHC(O)NH$_2$.

In an exemplary embodiment, Y comprises para-aminobenzyl or para-aminobenzyloxycarbonyl.

In an exemplary embodiment, the antibody-drug conjugate compound has the formula:

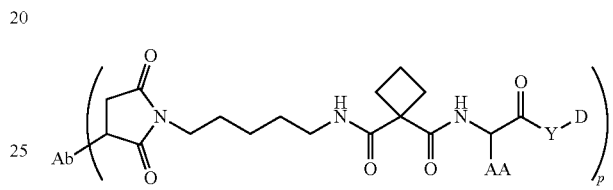

wherein D is the silvestrol drug moiety.

In an exemplary embodiment, the antibody-drug conjugate compound has the formula:

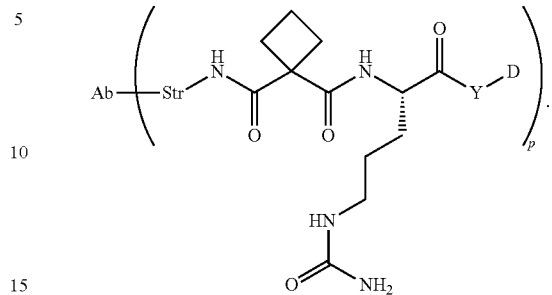

In an exemplary embodiment, the antibody-drug conjugate compound has the formula:

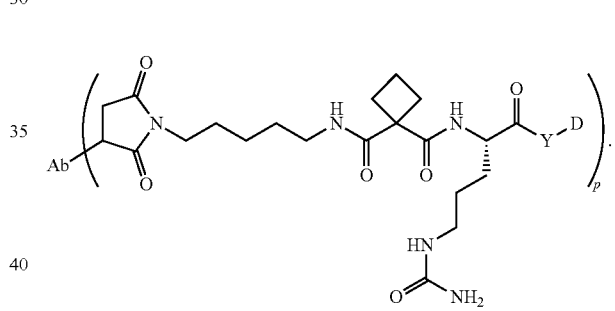

In an exemplary embodiment, the antibody-drug conjugate compound has the formula:

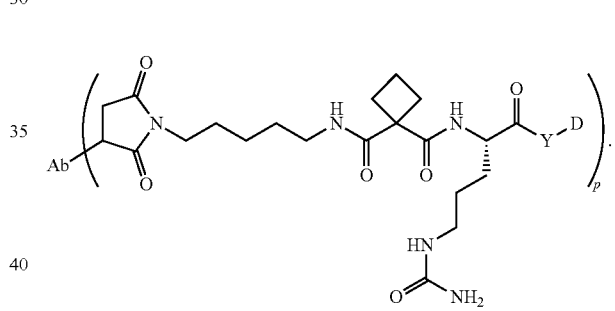

In an exemplary embodiment, the antibody-drug conjugate compound is selected from the formulas:

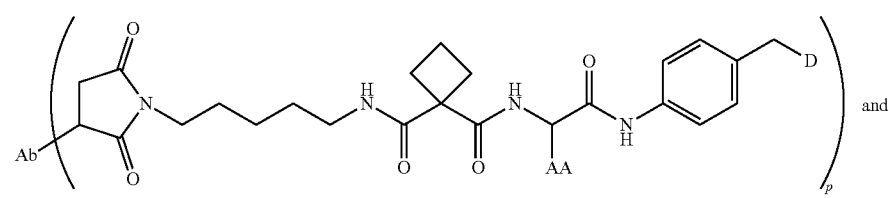 and

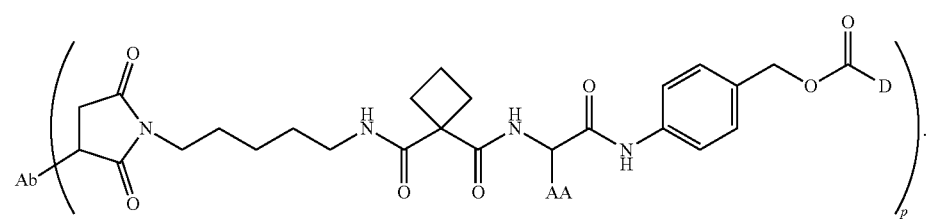

In an exemplary embodiment, L is a peptide linker having the formula:

-Str-Pep-Y— where Str is a stretcher unit covalently attached to the antibody; Pep is a peptide of two to twelve amino acid residues, and Y is a spacer unit covalently attached to the silvestrol drug moiety.

In an exemplary embodiment, Str has the formula:

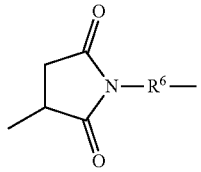

wherein $R^6$ is selected from the group consisting of $C_1$-$C_{12}$ alkylene, $C_1$-$C_{12}$ alkylene-C(=O), $C_1$-$C_{12}$ alkylene-NH, $(CH_2CH_2O)_r$, $(CH_2CH_2O)_r$—C(=O), $(CH_2CH_2O)_r$—$CH_2$, and $C_1$-$C_{12}$ alkylene-NHC(=O)$CH_2$CH(thiophen-3-yl), where r is an integer ranging from 1 to 10.

In an exemplary embodiment, $R^6$ is $(CH_2)_5$.

In an exemplary embodiment, Pep comprises two to twelve amino acid residues independently selected from glycine, alanine, phenylalanine, lysine, arginine, valine, and citrulline.

In an exemplary embodiment, Pep is selected from valine-citrulline, alanine-phenylalanine, and phenylalanine-lysine.

In an exemplary embodiment, Y comprises para-aminobenzyl or para-aminobenzyloxycarbonyl.

In an exemplary embodiment, the antibody-drug conjugate compound has the formula:

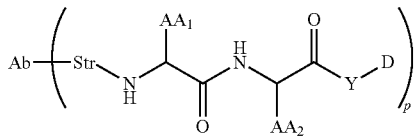

where $AA_1$ and $AA_2$ are independently selected from an amino acid side chain.

In an exemplary embodiment, the amino acid side chain is independently selected from H, —$CH_3$, —$CH_2(C_6H_5)$, —$CH_2CH_2CH_2CH_2NH_2$, —$CH_2CH_2CH_2NHC(NH)NH_2$, —$CHCH(CH_3)CH_3$, and —$CH_2CH_2CH_2NHC(O)NH_2$.

In an exemplary embodiment, the antibody-drug conjugate compound has the formula:

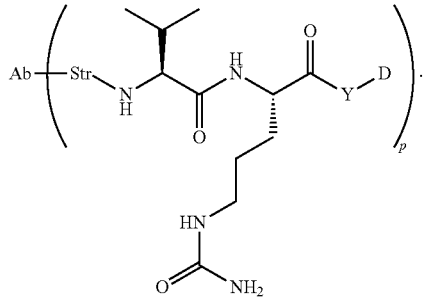

In an exemplary embodiment, the antibody-drug conjugate compound has the formula:

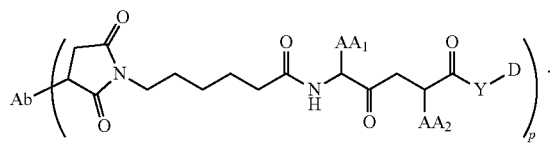

In an exemplary embodiment, the antibody-drug conjugate compound has the formula:

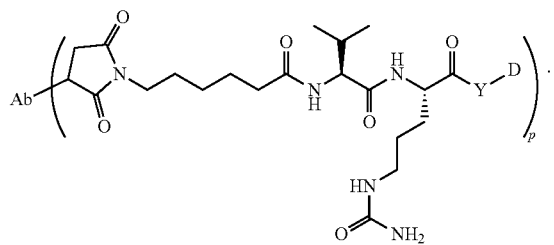

In an exemplary embodiment, the antibody-drug conjugate compound has the formula:

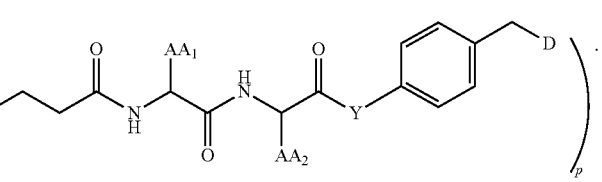

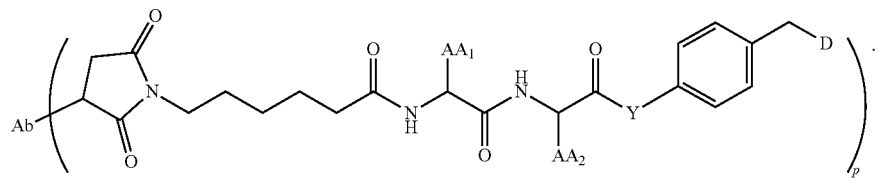

In an exemplary embodiment, the antibody-drug conjugate compound has the formula:

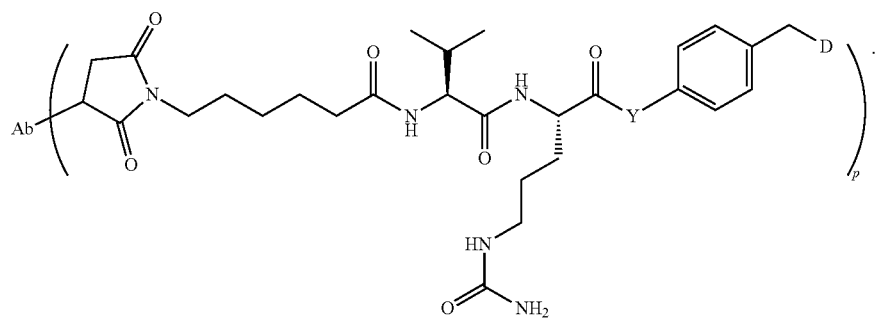

In an exemplary embodiment, the antibody-drug conjugate compound has the formula:

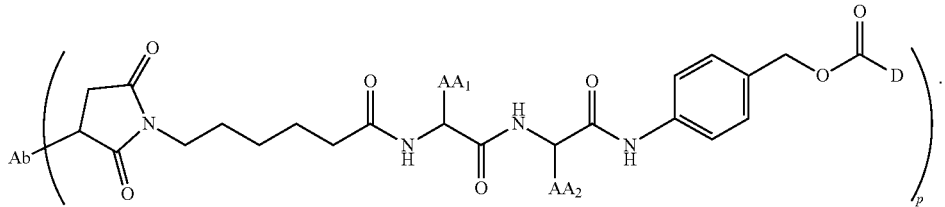

In an exemplary embodiment, the antibody-drug conjugate compound has the formula:

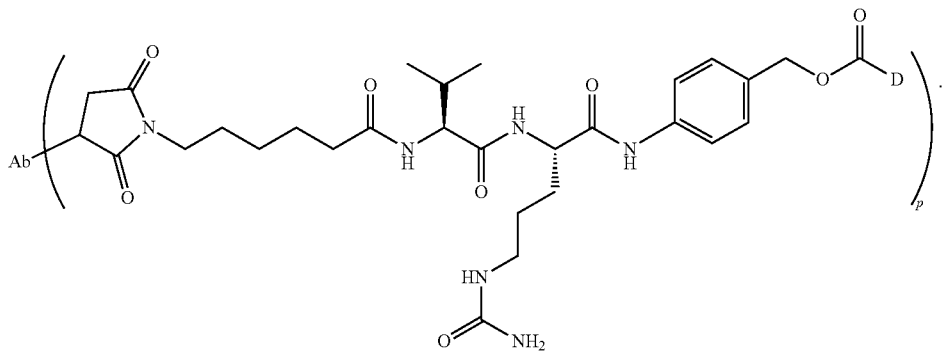

In an exemplary embodiment, L comprises a disulfide group.

In an exemplary embodiment, p is 1, 2, 3, or 4.

In an exemplary embodiment, the antibody-drug conjugate compound comprises a mixture of the antibody-drug conjugate compounds, wherein the average drug loading per antibody in the mixture of antibody-drug conjugate compounds is about 2 to about 5.

The antibody-drug conjugate compounds of the invention include those with anticancer activity. The antibody-drug conjugates of the invention selectively deliver an effective dose of a drug to tumor tissue, whereby greater selectivity (i.e., a lower efficacious dose) may be achieved while increasing the therapeutic index ("therapeutic window").

Drug loading is represented by p, the number of silvestrol drug moieties per antibody in a molecule of Formula I. Drug loading may range from 1 to about 8 drug moieties (D) per antibody. Antibody-drug conjugates of Formula I include mixtures or collections of antibodies conjugated with a range of drug moieties, from 1 to about 8. In some embodiments, the number of drug moieties that can be conjugated to an antibody is limited by the number of free cysteine residues. In some embodiments, free cysteine residues are introduced into the antibody amino acid sequence by the methods described herein. In such aspects, p may be 1, 2, 3, 4, 5, 6, 7, or 8, and ranges thereof, such as from 1 to 8 or from 2 to 5. In any such aspect, p and n are equal (i.e., p=n=1, 2, 3, 4, 5, 6, 7, or 8, or some range there between). Exemplary antibody-drug conjugates of Formula I include, but are not limited to, antibodies that have 1, 2, 3, or 4 engineered cysteine amino acids (Lyon, R. et al. (2012) *Methods in Enzym.* 502:123-138). In some embodiments, one or more cysteine residues are already present in an antibody, without the use of engineering, in which case the existing free cysteine residues may be used to conjugate the antibody to a drug. In some embodiments, an antibody is exposed to reducing conditions prior to conjugation of the antibody in order to generate one or more free cysteine residues. The average number of drug moieties per antibody (DAR) in preparations of antibody-drug conjugates from conjugation reactions may be characterized by conventional means such as mass spectroscopy, ELISA assay, and HPLC. The quantitative distribution of antibody-drug conjugates in terms of p may also be determined. In some instances, separation, purification, and characterization of homogeneous antibody-drug conjugates where p is a certain value from antibody-drug conjugates with other drug loadings may be achieved by means such as reverse phase HPLC or electrophoresis.

For some antibody-drug conjugates, p may be limited by the number of attachment sites on the antibody. For example, where the attachment is a cysteine thiol, as in certain exemplary embodiments described herein, an antibody may have only one or a limited number of cysteine thiol groups, or may have only one or a limited number of sufficiently reactive thiol groups, to which the drug may be attached. In certain embodiments, higher drug loading, e.g. p>5, may cause aggregation, insolubility, toxicity, or loss of cellular permeability of certain antibody-drug conjugates. In certain embodiments, the average drug loading for an antibody-drug conjugate ranges from 1 to about 8; from about 2 to about 6; or from about 3 to about 5. Indeed, it has been shown that for certain antibody-drug conjugates, the optimal ratio of drug moieties per antibody may be less than 8, and may be between about 2 to about 5 (see, e.g., U.S. Pat. No. 7,498,298).

In certain embodiments, fewer than the theoretical maximum of silvestrol drug moieties are conjugated to an antibody during a conjugation reaction. An antibody may contain, for example, cysteine residues that do not react with the drug, as discussed herein. Generally, antibodies do not contain many free and reactive cysteine thiol groups which may be linked to a drug moiety; indeed most native cysteine thiol residues in antibodies exist as disulfide bridges. In certain embodiments, an antibody may be reduced with a reducing agent such as dithiothreitol (DTT) or tricarbonylethylphosphine (TCEP), under partial or total reducing conditions, to generate reactive cysteine thiol groups. In certain embodiments, an antibody is subjected to denaturing conditions to reveal reactive nucleophilic groups such as lysine or cysteine.

The loading (drug/antibody ratio) of an antibody-drug conjugate may be controlled in different ways, and for example, by: (i) limiting the molar excess of the silvestrol-linker intermediate compound relative to antibody, (ii) limiting the conjugation reaction time or temperature, and (iii) partial or limiting reductive conditions for cysteine thiol modification.

It is to be understood that where more than one nucleophilic group reacts with a drug, then the resulting product is a mixture of antibody-drug conjugate compounds with a distribution of one or more drug moieties attached to an antibody. The average number of drugs per antibody may be calculated from the mixture by a dual ELISA antibody assay, which is specific for antibody and specific for the drug. Individual antibody-drug conjugate molecules may be identified in the mixture by mass spectroscopy and separated by HPLC, e.g. hydrophobic interaction chromatography (see, e.g., McDonagh et al. (2006) Prot. Engr. Design & Selection 19(7):299-307; Hamblett et al. (2004) Clin. Cancer Res. 10:7063-7070; Hamblett, K. J., et al. "Effect of drug loading on the pharmacology, pharmacokinetics, and toxicity of an anti-CD30 antibody-drug conjugate," Abstract No. 624, American Association for Cancer Research, 2004 Annual Meeting, March 27-31, 2004, Proceedings of the AACR, Volume 45, March 2004; Alley, S. C., et al. "Controlling the location of drug attachment in antibody-drug conjugates," Abstract No. 627, American Association for Cancer Research, 2004 Annual Meeting, Mar. 27-31, 2004, Proceedings of the AACR, Volume 45, March 2004). In certain embodiments, a homogeneous antibody-drug conjugate with a single loading value may be isolated from the conjugation mixture by electrophoresis or chromatography.

In some aspects, the antibody may be a cysteine engineered antibody as described elsewhere herein and/or may be treated with a reducing agent for reactivity in the conjugation reaction. The Ab is dissolved in a physiological buffer system known in the art that will not adversely impact the stability or antigen-binding specificity of the antibody. In some aspects, phosphate buffered saline is used. The silvestrol-linker intermediate compound is dissolved in a solvent system comprising at least one polar aprotic solvent as described elsewhere herein. In some such aspects, silvestrol-linker intermediate is dissolved to a concentration of about 5 mM, 10 mM, about 20 mM, about 30 mM, about 40 mM or about 50 mM, and ranges thereof such as from about 50 mM to about 50 mM or from about 10 mM to about 30 mM in pH 8 Tris buffer (e.g., 50 mM Tris). In some aspects, silvestrol-linker intermediate is dissolved in DMSO or acetonitrile, or in DMSO. In the conjugation reaction, an equivalent excess of silvestrol-linker intermediate solution is diluted and combined with chilled antibody solution (e.g. from about 1° C. to about 10° C.). The silvestrol-linker intermediate solution may suitably be diluted with at least one polar aprotic solvent and at least one polar protic solvent, examples of which include water, methanol, ethanol, n-propanol, and acetic acid. In some particular aspects the silvestrol-linker intermediate is dissolved in DMSO and diluted with acetonitrile and water prior to admixture with the antibody solution. The equivalents of silvestrol to antibody may suitably be about 1.5:1, about 3:1, about 5:1, about 10:1 about 15:1 or about 20:1, and ranges thereof, such as from about 1.5:1 to about 20:1 from about 1.5:1 to about 15:1, from about 1.5:1 to about 10:1,from about 3:1 to about 15:1, from about 3:1 to about 10:1, from about 5:1 to about 15:1 or from about 5:1 to about 10:1. The reaction may suitably be monitored for completion by methods known in the art, such as LC-MS (as described elsewhere herein), and the reaction is typically complete in from about 1 hour to about 24 hours. After the reaction is complete, a reagent is added to the reaction mixture to quench the reaction and cap unreacted antibody thiol groups. An example of a suitable reagent is ethylmaleimide.

Following conjugation according to Example 5, the antibody-silvestrol conjugates may be purified and separated from unconjugated reactants and/or conjugate aggregates by purification methods known in the art such as, for example and not limited to, size exclusion chromatography, hydrophobic interaction chromatography, ion exchange chromatography, chromatofocusing, ultrafiltration, centrifugal ultrafiltration, and combinations thereof. For instance, purification may be preceded by diluting the antibody-silvestrol conjugate, such in 20 mM sodium succinate, pH 5. The diluted solution is applied to a cation exchange column followed by washing with, e.g., at least 10 column volumes of 20 mM sodium succinate, pH 5. The conjugate may be suitably eluted with PBS.

TABLE 6

Antibody-drug conjugates (ADC)

| ADC No. | ADC formula | linker-drug LD No. (Table 5) | DAR* |
|---|---|---|---|
| ADC-101 | Thio anti-CD22 10F4v3 LC V205C sq-cit-silvestrol | LD-51 | 1.6 |
| ADC-102 | Thio anti-Napi2B 10H1.11.4B LC V205C sq-cit-silvestrol | LD-51 | 1.5 |
| ADC-103 | Thio Hu Anti-Her2 7C2 LC K149C silvestrol amine | LD-52 | 2.0 |
| ADC-104 | Thio Hu Anti-CD22 10F4v3 LC K149C silvestrol amine | LD-52 | 2.0 |
| ADC-105 | Thio Hu Anti-CD22 10F4v3 HC:A140C amino silvestrol analog | LD-53 | 1.95 |
| ADC-106 | Thio Hu Anti-Her2 7C2 HC:A140C amino silvestrol analog | LD-53 | 1.97 |
| ADC-107 | Thio Hu Anti-Ly6E 9B12.v12 LC:K149C MC-sqcit-PAB amino silvestrol | LD-58 | 2.01 |
| ADC-108 | Thio Hu Anti-CD22 10F4v3 LC:K149C MC-sqcit-PAB amino silvestrol | LD-58 | 2.01 |
| ADC-109 | Thio Hu Anti-Ly6E 9B12.v12 LC:K149C MC-sqcit-PAB silvestrol amine | LD-59 | 2.01 |
| ADC-110 | Thio Hu Anti-CD22 10F4v3 LC:K149C MC-sqcit-PAB silvestrol amine | LD-59 | 2.01 |

DAR = drug/antibody ratio average
A118C (EU numbering) = A121C (Sequential numbering) = A114C (Kabat numbering)
Wild-type ("WT"), cysteine engineered mutant antibody ("thio"), light chain ("LC"), heavy chain ("HC"), 6-maleimidocaproyl ("MC"), maleimidopropanoyl ("MP"), valine-citrulline ("val-cit" or "vc"), alanine-phenylalanine ("ala-phe"), p-aminobenzyl ("PAB"), and p-aminobenzyloxycarbonyl ("PABC")

In Vitro Cell Proliferation Assays

Generally, the cytotoxic or cytostatic activity of an antibody-drug conjugate (ADC) is measured by: exposing mammalian cells having receptor proteins, e.g. HER2, to the antibody of the ADC in a cell culture medium; culturing the cells for a period from about 6 hours to about 5 days; and measuring cell viability. Cell-based in vitro assays were used to measure viability (proliferation), cytotoxicity, and induction of apoptosis (caspase activation) of the ADC of the invention.

The in vitro potency of antibody-drug conjugates (ADC) was measured by a cell proliferation assay (Example 6). The ADC of the invention showed surprising and unexpected potency in inhibition of tumor cell proliferation. Potency of the ADC was correlated with target antigen expression of the cells. The tested conjugates are capable of binding to the specific antigen expressed on the surface of cells and causing the death of those cells in vitro.

The CellTiter-Glo® Luminescent Cell Viability Assay is a commercially available (Promega Corp., Madison, Wis.), homogeneous assay method based on the recombinant expression of Coleoptera luciferase (U.S. Pat. Nos. 5,583,024; 5,674,713; 5,700,670). This cell proliferation assay determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Glo® Assay was conducted in 96 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing. The cells may be treated continuously with ADC, or they may be treated and separated from ADC. Generally, cells treated briefly, i.e. 3 hours, showed the same potency effects as continuously treated cells.

Inhibition of cell proliferation in vitro may be assayed using the CellTiter-Glo™ Luminescent Cell Viability Assay, an embodiment of which is detailed as Example 6. Such assay determines the number of viable cells in culture based on quantitation of ATP present, which is an indication of metabolically active cells (Crouch et al. (1993) *J. Immunol. Meth.* 160:81-88; U.S. Pat. No. 6,602,677). The assay may be conducted in 96- or 384-well format, making it amenable to automated high-throughput screening (HTS). See Cree et al. (1995) *AntiCancer Drugs* 6:398-404. The assay procedure involves adding a single reagent (CellTiter-Glo® Reagent) directly to cultured cells. This results in cell lysis and generation of a luminescent signal produced by a luciferase reaction. The luminescent signal is proportional to the amount of ATP present, which is directly proportional to the number of viable cells present in culture. Data can be recorded by luminometer or CCD camera imaging device. The luminescence output is expressed as relative light units (RLU).

The homogeneous "add-mix-measure" format results in cell lysis and generation of a luminescent signal proportional to the amount of ATP present. The amount of ATP is directly proportional to the number of cells present in culture. The CellTiterGlo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons.

Cell-based in vitro assays are used to measure viability (proliferation), cytotoxicity, and induction of apoptosis (caspase activation) of the ADC of the invention. Generally, the cytotoxic or cytostatic activity of an antibody-drug conjugate (ADC) is measured by: exposing mammalian cells expressing antigen such as Her2 or MUC16 polypeptide to ADC in a cell culture medium; culturing the cells for a period from about 6 hours to about 5 days; and measuring cell viability. Mammalian cells useful for cell proliferation assays for anti-MUC16 ADC may include: (1) a MUC16 polypeptide-expressing cell line OVCAR-3; (2) a PC3-derived cell line engineered to stably express a portion of the MUC16 polypeptide on its cell surface (PC3/MUC16); (3) the parental PC3 cell line that does not express the MUC16 polypeptide; and (4) a PC3 cell line that does not express MUC16 polypeptide but carries the vector used to drive exogenous MUC16 expression (PC3/neo).

FIGS. 1A and 1B show the efficacy of antibody-drug conjugates in a plot of in vitro cell viability at 5 days versus concentrations (m/ml) of ADC in SK-BR-3 (FIG. 1A) and KPL-4 (FIG. 1B) cells. Cells were plated in 96-well plates (SK-BR-3, 5000 cells/well; KPL-4, 1500 cells/well), and allowed to adhere overnight, conducted according to Example 6. Medium was then removed and replaced by fresh culture medium containing different concentrations of conjugate. Cell viability was measured 5 days after drug administration using Cell Titer-Glo. In both cell lines, SK-BR-3 (FIG. 1A) and KPL-4 (FIG. 1B), ADC-103, Thio anti-Her2 7C2 LC-K149C-MC-vc-PAB-Silvestrol-amine, was more potent than ADC-106, Thio Hu Anti-Her2 7C2 HC:A140C amino silvestrol analog. Off-target control, ADC-105, Thio Hu Anti-CD22 10F4v3 HC:A140C amino silvestrol analog, was not active.

Free drug silvestrol amine (below) is inactive due to its impermeability, whereas free drug amino silvestrol analog is active (Table 7). 7C2 amino silvestrol analog ADC-106 is less potent than 7C2 silvestrol amine ADC-103. Biphasic dose response curve is observed with 7C2 amino silvestrol analog ADC-106. Free drug amino silvestrol analog has pM or low nM IC5os, whereas silvestrol amine free drug shows no activity due to its impermeability. Therefore it is difficult to determine if the potency difference between the two conjugates is caused by the difference of free drug potency. 7C2 amino silvestrol analog ADC-106 exhibits less potency in SK-BR-3 cells than KPL-4 cells, even though the free drug amino silvestrol analog has similar $IC_{50}$ values in SK-BR-3 (1.6 nM) and KPL-4 cells (1.2 nM)

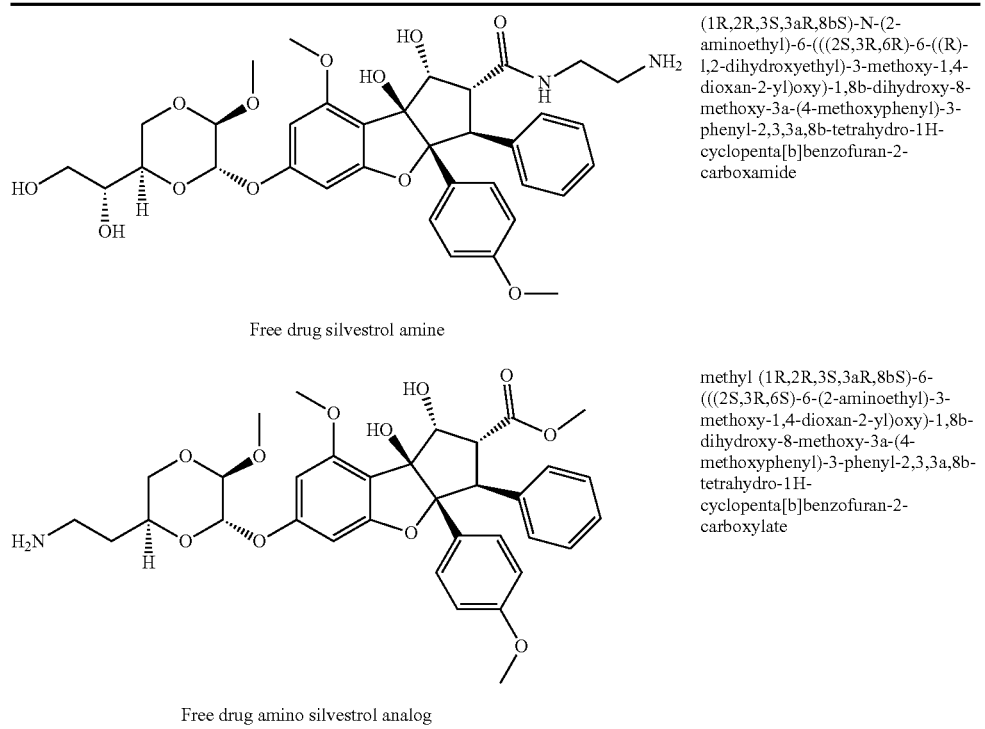

Free drug silvestrol amine (1R,2R,3S,3aR,8bS)-N-(2-aminoethyl)-6-(((2S,3R,6R)-6-((R)-1,2-dihydroxyethyl)-3-methoxy-1,4-dioxan-2-yl)oxy)-1,8b-dihydroxy-8-methoxy-3a-(4-methoxyphenyl)-3-phenyl-2,3,3a,8b-tetrahydro-1H-cyclopenta[b]benzofuran-2-carboxamide Free drug amino silvestrol analog methyl (1R,2R,3S,3aR,8bS)-6-(((2S,3R,6S)-6-(2-aminoethyl)-3-methoxy-1,4-dioxan-2-yl)oxy)-1,8b-dihydroxy-8-methoxy-3a-(4-methoxyphenyl)-3-phenyl-2,3,3a,8b-tetrahydro-1H-cyclopenta[b]benzofuran-2-carboxylate

TABLE 7

In vitro efficacy of free drug silvestrol compounds

| Cell line | IC50 (nM) Free drug silvestrol amine, | IC50 (nM) free drug amino silvestrol analog |
|---|---|---|
| MES-SA | >100 | 1.1 |
| MES-SA/Dx5 | >200 | >100 |
| BJAB | >200 | 0.81 |
| KPL-4 | >200 | 1.2 |
| HCC1569 X2 | >200 | 1.3 |
| T-47D | >200 | 1.0 |
| HCC1937 | >200 | 0.66 |
| NCI-H1781 | >200 | 1.0 |
| SW 900 | >200 | 2.9 |

In Vivo Efficacy

The in vivo efficacy of antibody-drug conjugates (ADC) of the invention can be measured by tumor xenograft studies in mice (Examples 7-10). The ADC of the invention showed surprising and unexpected, target-dependent and dose-dependent potency in inhibition of tumor growth. Efficacy of the ADC was correlated with target antigen expression of the tumor cells.

The efficacy of antibody-drug conjugates were measured in vivo by implanting allografts or xenografts of cancer cells in rodents and treating the tumors with ADC. Variable results are to be expected depending on the cell line, the specificity of antibody binding of the ADC to receptors present on the cancer cells, dosing regimen, and other factors. The in vivo efficacy of the ADC was measured using a transgenic explant mouse model expressing moderate to high levels of a tumor-associated antigen, including Her2-expressing KPL4, and CD22-expressing BJAB. Subjects were treated once with ADC and monitored over 3-6 weeks to measure the time to tumor doubling, log cell kill, and tumor shrinkage. Follow up dose-response and multi-dose experiments were conducted.

For example, the in vivo efficacy of an anti-HER2 ADC of the invention can be measured by a high expressing HER2 transgenic explant mouse model (Phillips et al (2008) Cancer Res. 68:9280-90). An allograft is propagated from the Fo5 mmtv transgenic mouse which does not respond to, or responds poorly to, HERCEPTIN® (Genentech, Inc.) therapy. Subjects are treated once or more with ADC at certain dose levels (mg/kg) and placebo buffer control (Vehicle) and monitored over two weeks or more to measure the time to tumor doubling, log cell kill, and tumor shrinkage, conducted according to Example 7.

FIG. 2 shows the efficacy of antibody-drug conjugates in a plot of the in vivo fitted tumor volume change over time in CD22-expressing Bjab-luc human xenograft model in CB-17 Fox Chase SCID mice, conducted according to Example 9. after dosing once IV with:

1) Vehicle (HisAc 20 mM, Sucr 240 mM, TW-20 0.02%, pH 5.5), 100 uL, IV once

2) Thio anti-CD22 LC-K149C-MC-vc-PAB-Silvestrol-amine, ADC-104, 1 mg/kg IV once, 3) Thio anti-CD22 LC-K149C-MC-vc-PAB-Silvestrol-amine, ADC-104, 3 mg/kg IV once, 4) Thio anti-CD22 LC-K149C-MC-vc-PAB-Silvestrol-amine, ADC-104, 6 mg/kg IV once, 5) Thio anti-CD22 LC-K149C-MC-vc-PAB-Silvestrol-amine, ADC-104, 10 mg/kg IV once, 6) Thio anti-Her2 7C2 LC-K149C-MC-vc-PAB-Silvestrol-amine, ADC-103, 3 mg/kg IV once, Activity is seen with all dose levels tested of CD22 Silvestrol-amine ADC-104 compared to the vehicle group. ADC-104 dosed at 1 and 3 mg/kg shows moderate activity and 6 and 10 mg/kg are around stasis. There is some growth delay with the Her2 control Silvestrol-amine ADC-103 dosed at 3 mg/kg. As a safety signal, no body weight loss seen. Evidence of tumor inhibition was observed, but was not definitive since tumor volumes were highly variable.

FIG. 3 shows the efficacy of antibody-drug conjugates in a plot of the in vivo fitted tumor volume change over time in HER2-expressing KPL4 human mammary xenograft model in scid beige mice, conducted according to Example 10.

1) Vehicle (HisAc 20 mM, Sucr 240 mM, TW-20 0.02%, pH 5.5), 100 uL, IV once
2) Silvestrol, 0.09 mg/kg, IV once
3) Silvestrol, 1 mg/kg, IP qdX5 for 2 weeks
4) Thio anti-Her2 7C2 LC-K149C-MC-vc-PAB-Silvestrol-amine, ADC-103, 1 mg/kg IV once
5) Thio anti-Her2 7C2 LC-K149C-MC-vc-PAB-Silvestrol-amine, ADC-103, 3 mg/kg IV once
6) Thio anti-Her2 7C2 LC-K149C-MC-vc-PAB-Silvestrol-amine, ADC-103, 6 mg/kg IV once
7) Thio anti-Her2 7C2 LC-K149C-MC-vc-PAB-Silvestrol-amine, ADC-103, 10 mg/kg IV once
8) Thio anti-CD22 LC-K149C-MC-vc-PAB-Silvestrol-amine, ADC-104, 3 mg/kg IV once Activity is seen with all dose levels tested of anti-HER2 7C2 Silvestrol-amine ADC-103 compared to the vehicle and off-target control ADC-104. ADC-103 dosed at 1 and 3 mg/kg shows moderate activity and 6 and 10 mg/kg are around stasis. There is no growth delay with the CD22 control Silvestrol-amine ADC-104 dosed at 3 mg/kg. As a safety signal, no body weight loss seen.

FIG. 4 shows the efficacy of antibody-drug conjugates in a plot of the in vivo fitted tumor volume change over time in CD-22 expressing, Bjab-luc human xenograft model in CB-17 Fox Chase SCID mice.

1) Vehicle (Histidine Buffer #8), 100 IV once
2) Thio CD22 LC-K149C-MC-vc-PAB-Silvestrol-amine, ADC-104, 10 mg/kg IV once
3) Thio Her2(7C2) LC-K149C-MC-vc-PAB-Silvestrol-amine, ADC-103, 10 mg/kg IV once
4) Thio CD22 HC-A140C-MC-vc-PAB-amino-Silvestrol, ADC-105, 1 mg/kg IV once
5) Thio CD22 HC-A140C-MC-vc-PAB-amino-Silvestrol, ADC-105, 3 mg/kg IV once
6) Thio CD22 HC-A140C-MC-vc-PAB-amino-Silvestrol, ADC-105, 6 mg/kg IV once
7) Thio CD22 HC-A140C-MC-vc-PAB-amino-Silvestrol, ADC-105, 10 mg/kg IV once
8 Thio Her2(7C2) HC-A140C-MC-vc-PAB-amino-Silvestrol, ADC-106, 3 mg/kg IV once
9) Thio Her2(7C2) HC-A140C-MC-vc-PAB-amino-Silvestrol, ADC-106, 10 mg/kg IV once Two dose levels of Her2 (7C2) HC A140C MC-vc-PAB-amino Silvestrol, ADC-106, as well as Her2 (7C2) LC K149C MC-vc-PAB-Silvestrol amine, ADC-103 are present as controls. Plasma for stability analysis was collected from Group 7 (10 mg/kg dose Thio CD22 HC-A140C-MC-vc-PAB-amino-Silvestrol, ADC-105) at Day 1, 3, and 7. CD22 LC K149C-MC-vc-PAB-Silvestrol amine, ADC-104): dosed at 10 mg/kg results in tumor stasis (102% TGI). Compared to result in FIG. 2, where it appeared animals either responded well to treatment or not at all, these results appear to confirm the tumor static response (5/5 animals with tumor stasis, but trending towards regression). Control Her2 (7C2) LC K149C-MC-vc-PAB-Silvestrol amine, ADC-103): dosed at 10 mg/kg results in 32% TGI. CD22 HC-A140C-MC-vc-PAB-amino-Silvestrol (CNJ 3592, G03063194): dosed from 1-10 mg/kg results in moderate TGI at 1 mg/kg (81%) and regression at all higher doses. Also, amino-Silvestrol appears more potent than Silvestrol-amine if we compare the two 10 mg/kg doses (Group 2 vs Group 7), but the caveat is they are on two different attachment sites. Control Her2 (7C2) HC A140C-MC-vcPAB-amino-Silvestrol (CNJ 3593, G03063194): 3 and 10 mg/kg doses result in similar modest response (30-40% TGI). No body weight loss observed in all dose groups.

Figure 5:
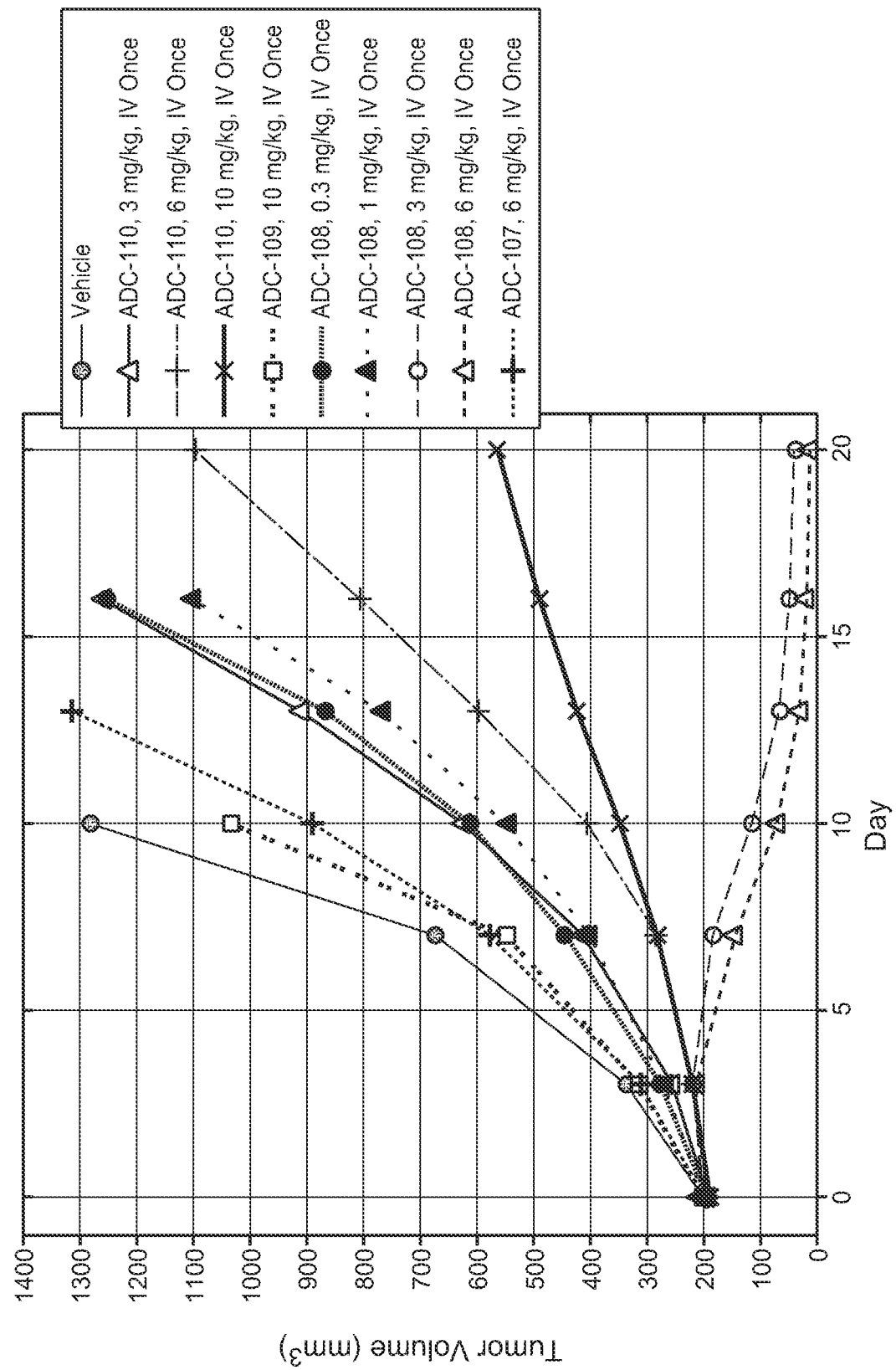
FIG. 5 shows the efficacy of antibody-drug conjugates in a plot of the in vivo fitted tumor volume change over time in Bjab-luc human xenograft model in CB-17 Fox Chase SCID mice.

FIG. 5 shows the efficacy of antibody-drug conjugates in a plot of the in vivo fitted tumor volume change over time in CD-22 expressing, Bjab-luc human xenograft model in CB-17 Fox Chase SCID mice.

1) Vehicle (Histidine Buffer #8), 100 uL, IV once
2) Thio Hu anti-CD22 10F4v3 LC K149C-MC-sq-cit-PAB-Silvestrol-amine, ADC-110, 3 mg/kg IV once
3) Thio Hu anti-CD22 10F4v3 LC K149C-MC-sq-cit-PAB-Silvestrol-amine, ADC-110, 6 mg/kg IV once
4) Thio Hu anti-CD22 10F4v3 LC K149C-MC-sq-cit-PAB-Silvestrol-amine, ADC-110, 10 mg/kg IV once
5) Thio Hu anti-LY6E 9B12v12 LC K149C-MC-sq-cit-PAB-Silvestrol-amine, ADC-109, 10 mg/kg IV once
6) Thio Hu anti-CD22 10F4v3 LC K149C-MC-sq-cit-PAB-amino-Silvestrol, ADC-108, 0.3 mg/kg IV once
7) Thio Hu anti-CD22 10F4v3 LC K149C-MC-sq-cit-PAB-amino-Silvestrol, ADC-108, 1 mg/kg IV once
8) Thio Hu anti-CD22 10F4v3 LC K149C-MC-sq-cit-PAB-amino-Silvestrol, ADC-108, 3 mg/kg IV once
9) Thio Hu anti-CD22 10F4v3 LC K149C-MC-sq-cit-PAB-amino-Silvestrol, ADC-108, 6 mg/kg IV once
10) Thio Hu anti-LY6E 9B12v12 LC K149C-MC-sq-cit-PAB-amino-Silvestrol, ADC-107, 6 mg/kg IV once The silvestrol amine ADC-110 gave moderate response at 10 mg/kg (Group 4) resulting in 81% tumor growth inhibition at day 20. The amino silvestrol ADC-108 gave complete tumor regression at 3 mg/kg (Group 8). In both cases, the efficacy was dose-dependent with lower doses giving less response. The efficacy was also target-specific as there was separation between the targeted CD22 ADCs, ADC-108 and ADC-110, and both non-target (LY6E) control ADCs, ADC-109 (Group 5) and ADC-107 (Group 10).

Pharmaceutical Formulations

Pharmaceutical formulations of therapeutic antibody-drug conjugates of the invention are typically prepared for parenteral administration, i.e. bolus, intravenous, intratumor injection in a unit dosage injectable form with the desired degree of purity and with one or more optional pharmaceutically acceptable carriers, excipient, and/or vehicles (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/ or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases, such as chondroitinases.

Exemplary lyophilized antibody or immunoconjugate formulations are described in U.S. Pat. No. 6,267,958. Aqueous antibody or immunoconjugate formulations include those described in U.S. Pat. No. 6,171,586 and WO 2006/044908, the latter formulations including a histidine-acetate buffer.

The formulation herein may also contain more than one active ingredient as necessary for the particular indication being treated, preferably those with complementary activities that do not adversely affect each other.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody or immunoconjugate, which matrices are in the form of shaped articles, e.g. films, or microcapsules.

The formulations to be used for in vivo administration are generally sterile. Sterility may be readily accomplished, e.g., by filtration through sterile filtration membranes.

Methods of Treatment

It is contemplated that the antibody-drug conjugates of the present invention may be used to treat various diseases or disorders, e.g. characterized by the overexpression of a tumor antigen. Exemplary conditions or hyperproliferative disorders include benign or malignant solid tumors and hematological disorders such as leukemia and lymphoid malignancies. Others include neuronal, glial, astrocytal, hypothalamic, glandular, macrophagal, epithelial, stromal, blastocoelic, inflammatory, angiogenic and immunologic, including autoimmune, disorders.

In one aspect, an antibody-drug conjugate provided herein is used in a method of inhibiting proliferation of a cancer cell, the method comprising exposing the cell to the antibody-drug conjugate under conditions permissive for binding of the antibody or antibody-drug conjugates to a tumor-associated antigen on the surface of the cell, thereby inhibiting the proliferation of the cell. In certain embodiments, the method is an in vitro or an in vivo method. In further embodiments, the cell is a lymphocyte, lymphoblast, monocyte, or myelomonocyte cell.

In another aspect, an antibody-drug conjugate for use as a medicament is provided. In further aspects, an antibody-drug conjugate for use in a method of treatment is provided. In certain embodiments, an antibody-drug conjugate for use in treating cancer is provided. In certain embodiments, the invention provides an antibody-drug conjugate for use in a method of treating an individual comprising administering to the individual an effective amount of the antibody-drug conjugate. In one such embodiment, the method further comprises administering to the individual an effective amount of at least one additional therapeutic agent, e.g., as described herein.

In a further aspect, the invention provides for the use of an antibody-drug conjugate in the manufacture or preparation of a medicament. In one embodiment, the medicament is for treatment of cancer, the method comprising administering to an individual having cancer an effective amount of the medicament. In one such embodiment, the method further comprises administering to the individual an effective amount of at least one additional therapeutic agent, e.g., as described herein.

In a further aspect, the invention provides a method for treating cancer. In one embodiment, the method comprises administering to an individual having such cancer, characterized by detection of a tumor-associated expressing antigen, an effective amount of an antibody-drug conjugate of the invention. In one such embodiment, the method further comprises administering to the individual an effective amount of at least one additional therapeutic agent, as described herein.

Antibody-drug conjugates of the invention can be used either alone or in combination with other agents in a therapy. For instance, an antibody-drug conjugate of the invention may be co-administered with at least one additional therapeutic agent, such as a chemotherapeutic agent.

Such combination therapies noted herein encompass combined administration (where two or more therapeutic agents are included in the same or separate formulations), and separate administration, in which case, administration of the antibody-drug conjugate of the invention can occur prior to, simultaneously, and/or following, administration of the additional therapeutic agent and/or adjuvant. Antibody-drug conjugates of the invention can also be used in combination with radiation therapy.

Antibody-drug conjugates of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various timepoints, bolus administration, and pulse infusion are contemplated herein.

Antibody-drug conjugates of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody-drug conjugate need not be, but is optionally formulated with one or more agents currently used to prevent or treat the disorder in question. The effective amount of such other agents depends on the amount of antibody-drug conjugate present in the formulation, the type of disorder or treatment, and other factors discussed herein. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody-drug conjugate of the invention (when used alone or in combination with one or more other additional therapeutic agents) will depend on the type of disease to be treated, the type of antibody or immunoconjugate, the severity and course of the disease, whether the antibody-drug conjugate is administered for preventive or therapeutic purposes, previous therapy, the patient's clinical history and response to antibody-drug conjugate, and the discretion of the attending physician. The antibody-drug conjugate is suitably administered to the patient at one time or over a series of treatments. Depending on the type and severity of the disease, about 1 μg/kg to 15 mg/kg (e.g. 0.1 mg/kg-10 mg/kg) of antibody-drug conjugate can be an initial candidate dosage for administration to the patient, whether, for example, by one or more separate administrations, or by continuous infusion. One typical daily dosage might range from about 1 μg/kg to 100 mg/kg or more, depending on the factors mentioned herein. For repeated administrations over several days or longer, depending on the condition, the treatment would generally be sustained until a desired suppression of disease symptoms occurs. One exemplary dosage of the antibody-drug conjugate would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. However, other dosage regimens may be useful. The progress of this therapy is easily monitored by conventional techniques and assays.

Intracellular release of silvestrol from the antibody-silvestrol conjugate in a target cell is believed to result from cleavage of the linker unit to release an active silvestrol moiety, such as reductive cleavage of a disulfide linker bond by glutathione or protease cleavage of a peptide or peptidomimetic unit. Glutathione-mediated release provides for advantages as compared to certain linkers known in the prior art, such as acid-labile hydrazine linkers. More particularly, blood concentration of glutathione is known to be very low, such as in the micromolar range, whereas intracellular glutathione concentration is typically up to three orders of magnitude greater, such as in the millimolar range. It is further believed that glutathione concentration in cancer cells is even greater due to increased activity of reductive enzymes. Therefore, it is believed that the silvestrol-antibody conjugates of the present disclosure provide for improved stability in the bloodstream and for improved intracellular release rates.

Articles of Manufacture

In another aspect of the invention, an article of manufacture containing materials useful for the treatment, prevention and/or diagnosis of the disorders described herein is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the disorder and may have a sterile access port (for example the container may be an intravenous solution bag or a vial having a stopper pierceable by a hypodermic injection needle). At least one active agent in the composition is an antibody-drug conjugate of the invention. The label or package insert indicates that the composition is used for treating the condition of choice. Moreover, the article of manufacture may comprise (a) a first container with a composition contained therein, wherein the composition comprises an antibody-drug conjugate of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution or dextrose solution. It may further include other materials desirable from a commercial and user standpoint, including other buffers, diluents, filters, needles, and syringes.

EXAMPLES

The following are examples of methods and compositions of the invention. It is understood that various other embodiments may be practiced, given the general description provided herein.

Example 1a

Silvestrol-Linker Intermediate LD-51 (Table 5). Synthesis of (1R,2R,3 S,3 aR, 8b S)-methyl 6-(((2 S,3R,6R)-6-((4R)-2-(4-((S)-2-(1-((5-(2,5-dioxo-2,5-dihydro-1H-pyrrol-1-yl)pentyl)carbamoyl)cyclobutanecarboxamido)-5-ureidopentanamido)phenyl)-1, 3-dioxolan-4-yl)-3-methoxy-1,4-dioxan-2-yl)oxy)-1, 8b-dihydroxy-8-methoxy-3a-(4-methoxyphenyl)-3-phenyl-2,3,3a,8b-tetrahydro-1H-cyclopenta[b] benzofuran-2-carboxylate LD-51

Step 1: Preparation of
1-(5-aminopentyl)-1H-pyrrole-2,5-dione
hydrochloride 10a

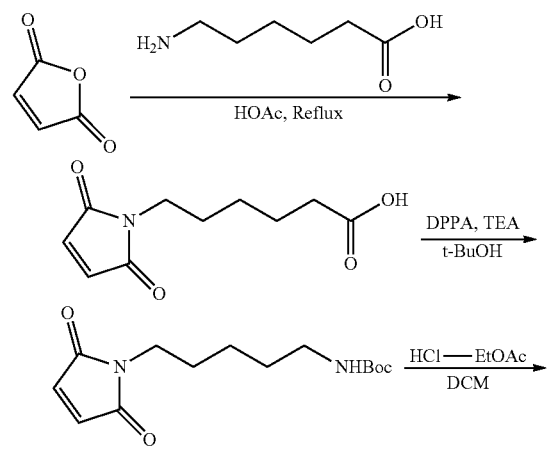

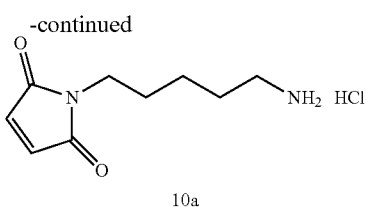

10a

Maleic anhydride, furan-2,5-dione (150 g, 1.53 mol) was added to a stirred solution of 6-aminohexanoic acid (201 g, 1.53 mol) in HOAc (1000 mL). After the mixture was stirred at r.t. for 2 h, it was heated at reflux for 8 h. The organic solvents were removed under reduced pressure and the residue was extracted with EtOAc (500 mL×3), washed with H₂O. The combined organic layers was dried over Na₂SO₄ and concentrated to give the crude product. It was washed with petroleum ether to give 6-(2,5-dioxo-2,5-dihydro-1H-pyrrol-1-yl)hexanoic acid as white solid (250 g, 77.4%). DPPA (130 g, 473 mmol) and TEA (47.9 g, 473 mmol) was added to a solution of 6-(2,5-dioxo-2,5-dihydro-1H-pyrrol-1-yl)hexanoic acid (100 g, 473 mmol) in t-BuOH (200 mL). The mixture was heated at reflux for 8 h under N₂. The mixture was concentrated, and the residue was purified by column chromatography on silica gel (PE:EtOAc=3:1) to give tert-butyl 5-(2,5-dioxo-2,5-dihydro-1H-pyrrol-1-yl) pentylcarbamate (13 g, 10%). To a solution of tert-butyl 5-(2,5-dioxo-2,5-dihydro-1H-pyrrol-1-yl)pentylcarbamate (28 g, 992 mmol) in anhydrous EtOAc (30 mL) was added HCl/EtOAc (50 mL) dropwise. After the mixture was stirred at r.t. for 5 h, it was filtered and the solid was dried to give 1-(5-aminopentyl)-1H-pyrrole-2,5-dione hydrochloride 10a (16 g, 73.7%). ¹H NMR (400 MHz, DMSO-d₆): δ 8.02 (s, 2H), 6.99 (s, 2H), 3.37-3.34 (m, 2H), 2.71-2.64 (m, 2H), 1.56-1.43 (m, 4H), 1.23-1.20 (m, 2H).

Step 2: Preparation of (S)-1-(1-(4-(hydroxymethyl) phenylamino)-1-oxo-5-ureidopentan-2-ylcarbamoyl) cyclobutanecarboxylic acid 10b

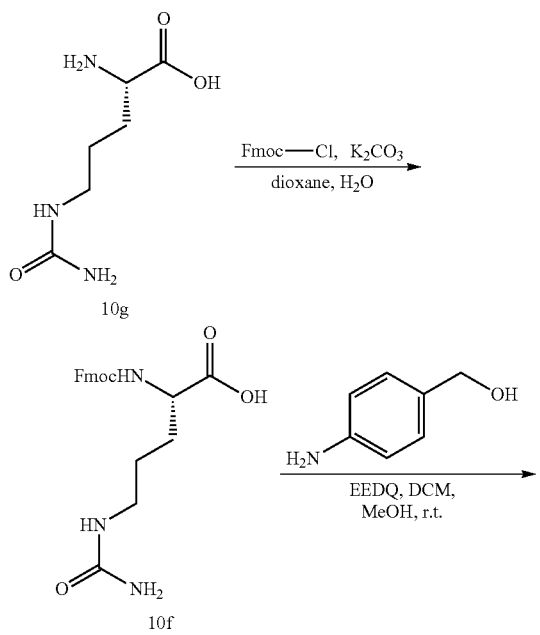

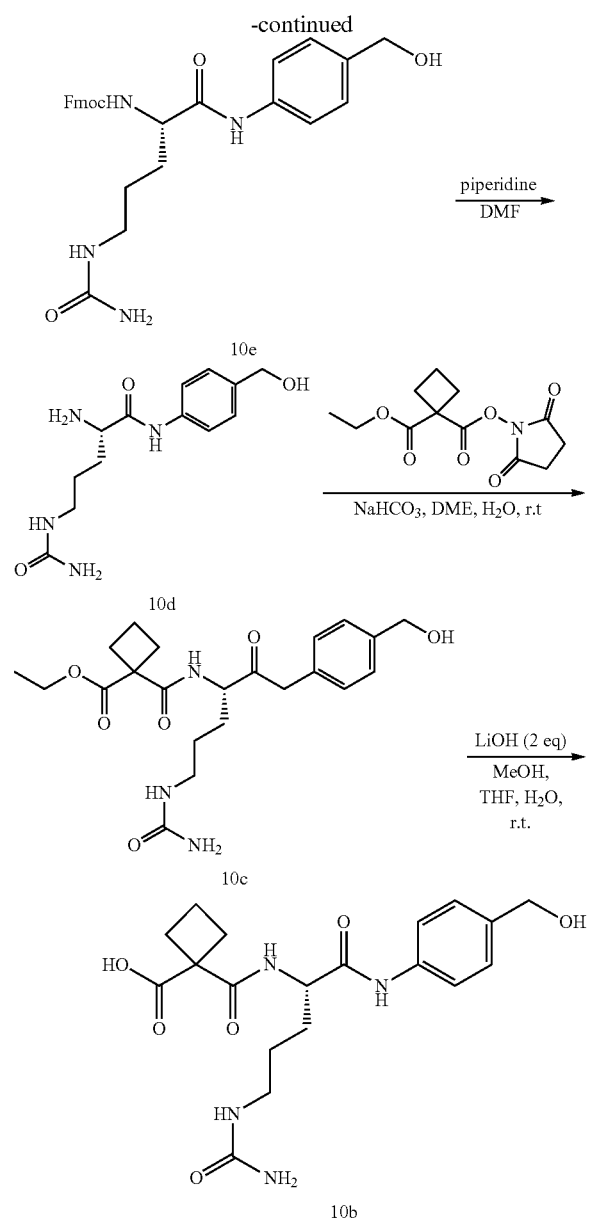

To a mixture of (S)-2-amino-5-ureidopentanoic acid 10g (17.50 g, 0.10 mol) in a mixture of dioxane and H₂O (50 mL/75 mL) was added K₂CO₃ (34.55 g, 0.25 mol). Fmoc-Cl (30.96 g, 0.12 mol) was added slowly at 0° C. The reaction mixture was warmed to r.t. over 2 h. Organic solvent was removed under reduced pressure, and the water slurry was adjusted to pH=3 with 6 M HCl solution, and extracted with EtOAc (100 mL×3). The organic layer was dried over Na₂SO₄, filtered, and concentrated under reduced pressure to give (S)-2-((((9H-fluoren-9-yl)methoxy)carbonyl) amino)-5-ureidopentanoic acid 10f (38.0 g, 95.6%). 10f is commercially available.

To a solution of 10f (4 g, 10 mmol) in a mixture of DCM and MeOH (100 mL/50 mL) were added (4-aminophenyl) methanol (1.6 g, 13 mmol, 1.3 eq) and 2-Ethoxy-1-ethoxy-carbonyl-1,2-dihydroquinoline, EEDQ, Sigma-Aldrich CAS Reg. No. 16357-59-8 (3.2 g, 13 mmol, 1.3 eq). After the mixture was stirred at r.t. for 16 h under N₂, it was concentrated to give a brown solid. MTBE (200 mL) was added and it was stirred at 15° C. for 2 h. The solid was collected by filtration, washed with MTBE (50 mL×2) to give (S)-(9H-fluoren-9-yl)methyl (1-((4-(hydroxymethyl)phenyl)amino)-1-oxo-5-ureidopentan-2-yl)carbamate 10e as an orange solid (4.2 g, 84%). LCMS (ESI): m/z 503.0 [M+1].

To a stirred solution of 10e (4.2 g, 8.3 mmol) in dry DMF (20 ml) was added piperidine (1.65 mL, 17 mmol, 2 eq) dropwise at r.t. The mixture was stirred at r.t. for 30 min, and solid precipitate formed. Dry DCM (50 mL) was added, and the mixture became transparent immediately. The mixture was stirred at r.t. for another 30 min, and LCMS showed 10e was consumed. It was concentrated to dryness under reduced pressure (make sure no piperidine remained), and the residue was partitioned between EtOAc and H₂O (50 mL/20 mL). Aqueous phase was washed with EtOAc (50 mL×2) and concentrated to give (S)-2-amino-N-(4-(hydroxymethyl)phenyl)-5-ureidopentanamide 10d as an oily residual (2.2 g, 94%) (contained small amount of DMF).

Commercially available 1,1-cyclobutanedicarboxylic acid, 1,1-diethyl ester (CAS Reg. No. 3779-29-1) was converted by limited saponification with aqueous base to the half acid/ester 1,1-cyclobutanedicarboxylic acid, 1-ethyl ester (CAS Reg No. 54450-84-9) and activation with a coupling reagent such as TBTU (O-(Benzotriazol-1-yl)-N,N,N',N'-tetramethyluronium tetrafluoroborate, also called: N,N,N',N'-Tetramethyl-O-(benzotriazol-1-yl)uronium tetrafluoroborate, CAS No. 125700-67-6, Sigma-Aldrich B-2903), and N-hydroxysuccinimide to the NHS ester, 1-(2,5-dioxopyrrolidin-1-yl) 1-ethyl cyclobutane-1,1-dicarboxylate.

To a solution of 1-(2,5-dioxopyrrolidin-1-yl) 1-ethyl cyclobutane-1,1-dicarboxylate (8 g, 29.7 mmol) in DME (50 mL) was added a solution of 10d (6.0 g, 21.4 mmol) and NaHCO₃ (7.48 g, 89.0 mmol) in water (30 mL). After the mixture was stirred at r.t. for 16 h, it was concentrated to dryness under reduced pressure and the residue was purified by column chromatography (DCM:MeOH=10:1) to give (S)-ethyl 1-((1-(4-(hydroxymethyl)phenyl)-2-oxo-6-ureido-hexan-3-yl)carbamoyl)cyclobutanecarboxylate 10c as white solid (6.4 g, 68.7%). LCMS (ESI): m/z 435.0 [M+1]

To a stirred solution of 10c (6.4 g, 14.7 mmol) in a mixture of THF and MeOH (20 mL/10 mL) was added a solution of LiOH.H₂O (1.2 g, 28.6 mmol) in H₂O (20 mL) at r.t. After the reaction mixture was stirred at r.t. for 16 h, solvent was removed under reduced pressure, the residue obtained was purified by prep-HPLC to give (S)-1-(1-(4-(hydroxymethyl)phenylamino)-1-oxo-5-ureidopentan-2-ylcarbamoyl)cyclobutanecarboxylic acid 10b (3.5 g, yield: 58.5%). LCMS (ESI): m/z 406.9 [M+1]. ¹H NMR (400 MHz, Methanol-d₄) δ 8.86 (d, J=8.4 Hz, 2H), 8.51 (d, J=8.4 Hz, 2H), 5.88-5.85 (m, 1H), 5.78 (s, 2H), 4.54-4.49 (m, 3H), 4.38-4.32 (m, 1H), 3.86-3.75 (m, 1H), 3.84-3.80 (m, 2H), 3.28-3.21 (m, 1H), 3.30-3.24(m, 1H), 3.00-2.80(m, 1H), 2.37-2.28(m,2H).

Step 3: Preparation of S)-N-(5-(2,5-dioxo-2,5-dihydro-1H-pyrrol-1-yl)pentyl)-N-(1-(4-(hydroxymethyl)phenylamino)-1-oxo-5-ureidopentan-2-yl)cyclobutane-1,1-dicarboxamide 10

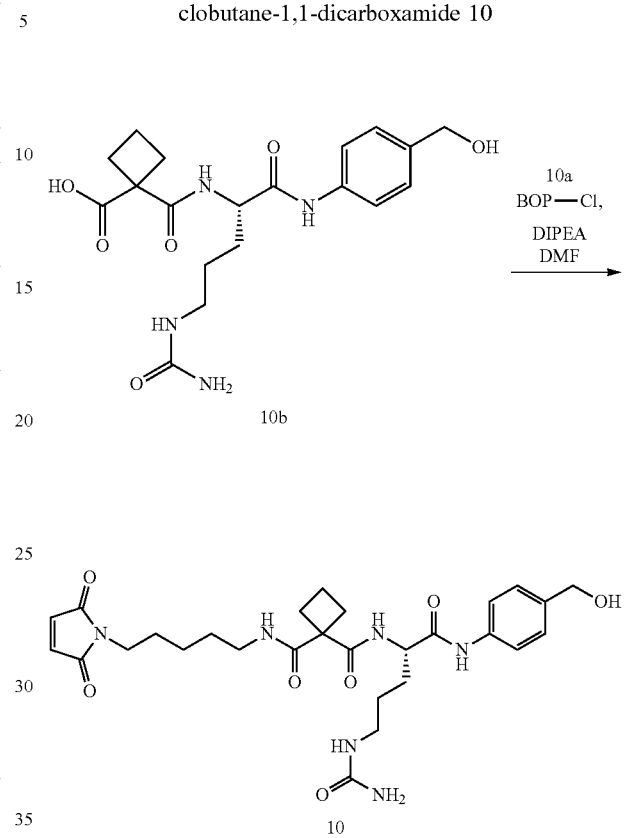

Diisopropylethylamine, DIPEA (1.59 g, 12.3 mmol) and bis(2-oxo-3-oxazolidinyl)phosphinic chloride, BOP-Cl (CAS Reg. No. 68641-49-6, Sigma-Aldrich, 692 mg, 2.71 mmol) was added to a solution of (S)-1-(1-(4-(hydroxymethyl)phenylamino)-1-oxo-5-ureidopentan-2-ylcarbamoyl) cyclobutanecarboxylic acid 10b (1 g, 2.46 mmol) in DMF (10 mL) at 0° C., followed by 1-(5-aminopentyl)-1H-pyrrole-2,5-dione hydrochloride 10a (592 mg, 2.71 mmol). The mixture was stirred at 0° C. for 0.5 h. The reaction mixture was quenched with citric acid solution (10 mL), extracted with DCM/MeOH (10:1). The organic layer was dried and concentrated, and the residue was purified by column chromatography on silica gel (DCM:MeOH=10:1) to give to give S)-N-(5-(2,5-dioxo-2,5-dihydro-1H-pyrrol-1-yl)pentyl)-N-(1-(4-(hydroxymethyl)phenylamino)-1-oxo-5-ureidopentan-2-yl)cyclobutane-1,1-dicarboxamide 10 (1.0 g, 71%), also referred to as MC-CBDK-cit-PAB-OH. LCMS (ESI): M+H⁺=571.28. ¹H NMR (400 MHz, DMSO-d₆): δ 10.00 (s, 1H), 7.82-7.77 (m, 2H), 7.53 (d, J=8.4 Hz, 2H), 7.19 (d, J=8.4 Hz, 2H), 6.96 (s, 2H), 5.95 (t, J=6.4 Hz, 1H), 5.39 (s, 2H), 5.08 (t, J=5.6 Hz, 1H), 4.40-4.35 (m, 3H), 4.09 (d, J=4.8 Hz, 1H), 3.01 (d, J=3.2 Hz, 2H), 3.05-2.72 (m, 4H), 2.68-2.58 (m, 3H), 2.40-2.36 (m, 4H), 1.72-1.70 (m, 3H), 1.44-1.42 (m, 1H), 1.40-1.23 (m, 6H), 1.21-1.16 (m, 4H).

Step 4: Preparation of (S)-N-(1-(4-(chloromethyl) phenylamino)-1-oxo-5-ureidopentan-2-yl)-N-(5-(2, 5-dioxo-2,5-dihydro-1H-pyrrol-1-yl)pentyl)cyclobutane-1,1-dicarboxamide 11

11

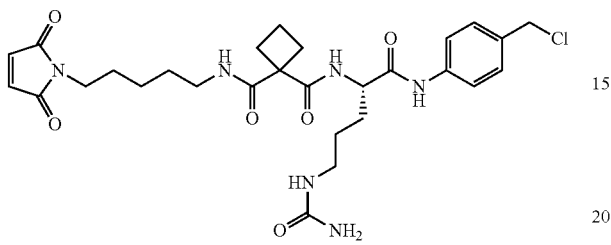

A solution of (S)-N-(5-(2,5-dioxo-2,5-dihydro-1H-pyrrol-1-yl)pentyl)-N-(1-(4-(hydroxymethyl)phenylamino)-1-oxo-5-ureidopentan-2-yl)cyclobutane-1,1-dicarboxamide 10 (2.0 g, 3.5 mmol) in N,N-dimethylformamide, DMF or N-methylpyrrolidone, NMP (50 mL) was treated with thionyl chloride, SOCl$_2$ (1.25 g, 10.5 mmol) in portions dropwise at 0° C. The reaction remained yellow. The reaction was monitored by LC/MS indicating >90% conversion. After the reaction mixture was stirred at 20° C. for 30 min or several hours, it was diluted with water (50 mL) and extracted with EtOAc (50 mL×3). The organic layer was dried, concentrated and purified by flash column (DCM:MeOH=20:1) to to form 11, also referred to as MC-CBDK-cit-PAB-Cl as a gray solid. LCMS: (5-95, AB, 1.5 min), 0.696 min, m/z=589.0 [M+1]$^+$.

Step 5: Preparation of (S)-4-(2-(1-(5-(2,5-dioxo-2,5-dihydro-1H-pyrrol-1-yl)pentylcarbamoyl)cyclobutanecarboxamido)-5-ureidopentanamido)benzyl 4-nitrophenyl carbonate 12

To a solution of (S)-N-(5-(2,5-dioxo-2,5-dihydro-1H-pyrrol-1-yl)pentyl)-N-(1-(4-(hydroxymethyl)phenylamino)-1-oxo-5-ureidopentan-2-yl)cyclobutane-1,1-dicarboxamide 10 in anhydrous DMF was added diisopropylethylamine (DIEA), followed by PNP carbonate (bis(4-nitrophenyl) carbonate). The reaction solution was stirred at room temperature (r.t.) for 4 hours and the mixture was purified by prep-HPLC to afford 12. LCMS (ESI): M+H$^+$=736.29.

Step 6: Preparation of LD-51

13

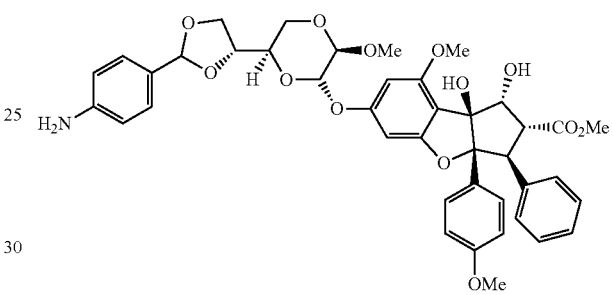

A solution of (S)-4-(2-(1-(5-(2,5-dioxo-2,5-dihydro-1H-pyrrol-1-yl)pentylcarbamoyl)cyclobutanecarboxamido)-5-ureidopentanamido)benzyl 4-nitrophenyl carbonate 12 and (1R,2R,3S,3aR,8bS)-methyl 6-(((2S,3R,6R)-6-((4R)-2-(4-aminophenyl)-1,3-dioxolan-4-yl)-3-methoxy-1,4-dioxan-2-yl)oxy)-1,8b-dihydroxy-8-methoxy-3a-(4-methoxyphenyl)-3-phenyl-2,3,3a,8b-tetrahydro-1H-cyclopenta[b]benzofuran-2-carboxylate 13 were reacted to give LD-51.

Alternatively, Silvestrol-Linker Intermediate LD-51 (Table 5) was prepared by the following Steps 7-12:

12

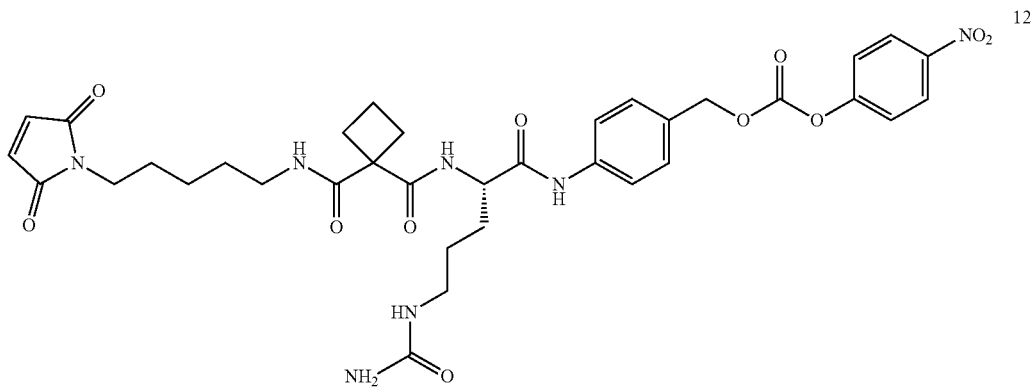 [SMILES: NC(=O)NCCC[C@H](NC(=O)C1(C(=O)NCCCCCN2C(=O)C=CC2=O)CCC1)C(=O)Nc1ccc(COC(=O)Oc2ccc([N+](=O)[O-])cc2)cc1]

Step 7: Preparation of 2,5-dioxopyrrolidin-1-yl 1-((5-(2,5-dioxo-2,5-dihydro-1H-pyrrol-1-yl)pentyl)carbamoyl)cyclobutanecarboxylate 15

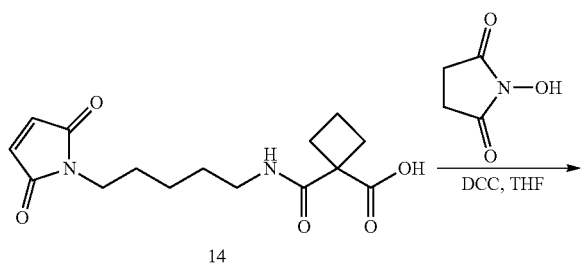

NHS (39 mg, 0.34 mmol), followed by dicyclohexylcarbodiimide, DCC (70 mg, 0.34 mmol) at 20° C. The mixture was stirred at 20° C. for 16 hours under nitrogen gas, $N_2$. The mixture was filtered and the filtrate was concentrated to give 2,5-dioxopyrrolidin-1-yl 1-((5-(2,5-dioxo-2,5-dihydro-1H-pyrrol-1-yl)pentyl)carbamoyl)cyclobutanecarboxylate 15 as colorless oil (131 mg, 100%).

Step 8: Preparation of (1R,2R,3S,3aR,8bS)-methyl 6-(((2S,3R,6R)-6-((4R)-2-(4-((((9H-fluoren-9-yl)methoxy)carbonyl)amino)phenyl)-1,3-dioxolan-4-yl)-3-methoxy-1,4-dioxan-2-yl)oxy)-1,8b-dihydroxy-8-methoxy-3a-(4-methoxyphenyl)-3-phenyl-2,3,3a,8b-tetrahydro-1H-cyclopenta[b]benzofuran-2-carboxylate 17

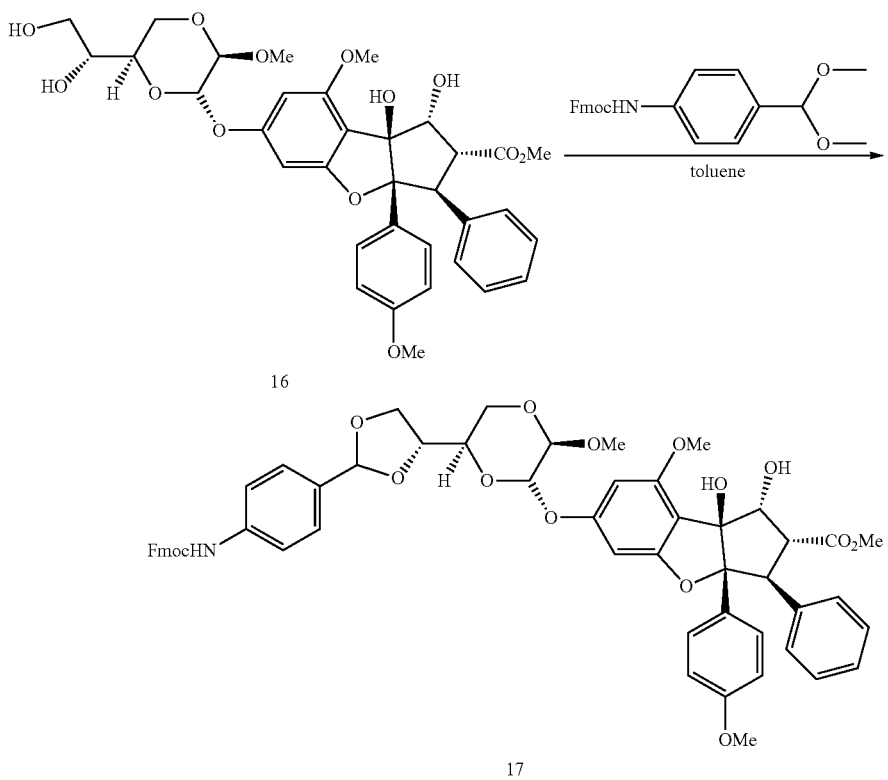

-continued

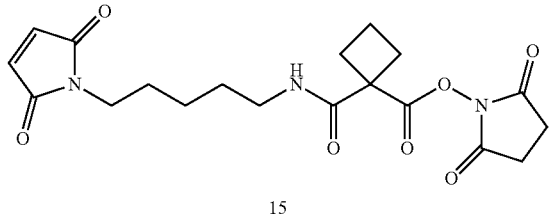

To a stirred solution of 1-((5-(2,5-dioxo-2,5-dihydro-1H-pyrrol-1-yl)pentyl)carbamoyl)cyclobutanecarboxylic acid 14 (100 mg, 0.324 mmol) in THF (10 mL) was added 1-hydroxypyrrolidine-2,5-dione, N-hydroxysuccinimide, Silvestrol, (1R,2R,3S,3aR,8bS)-methyl 6-(((2S,3R,6R)-6-((R)-1,2-dihydroxyethyl)-3-methoxy-1,4-dioxan-2-yl)oxy)-1,8b-dihydroxy-8-methoxy-3a-(4-methoxyphenyl)-3-phenyl-2,3,3a,8b-tetrahydro-1H-cyclopenta[b]benzofuran-2-carboxylate 16 (50 mg, 0.076 mmol), and (9H-fluoren-9-yl)methyl (4-(dimethoxymethyl)phenyl)carbamate (149 mg, 0.382 mmol) were dissolved in anhydrous toluene (5.0 mL). The resulting mixture was heated at 100-120° C. for 2 h. After it was cooled to r.t., the mixture was concentrated and purified by prep-TLC (DCM/MeOH=30/1) to give 17 as a white solid (43 mg, 57%). LCMS (5-95, AB, 1.5 min): $R_T$=0.928 min, m/z=1002.2 [M+Na]$^+$.

Step 9: Preparation of (1R,2R,3S,3aR,8bS)-methyl 6-(((2S,3R,6R)-6-((4R)-2-(4-aminophenyl)-1,3-dioxolan-4-yl)-3-methoxy-1,4-dioxan-2-yl)oxy)-1,8b-dihydroxy-8-methoxy-3a-(4-methoxyphenyl)-3-phenyl-2,3,3a,8b-tetrahydro-1H-cyclopenta[b]benzofuran-2-carboxylate 13

To a solution of 17 (30 mg, 0.031 mmol) in anhydrous DMF (2.0 mL) was added piperidine (5.2 mg, 0.061 mmol) at 20° C. The mixture was stirred at 20° C. for 2 h. The mixture was concentrated to give crude 13 (24 mg, 100%), used for next step without further purification.

Step 10: Preparation of (1R,2R,3S,3aR,8bS)-methyl 6-(((2S,3R,6R)-6-((4R)-2-(4-((S)-2-(((9H-fluoren-9-yl)methoxy)carbonyl)amino)-5-ureidopentanamido)phenyl)-1,3-dioxolan-4-yl)-3-methoxy-1,4-dioxan-2-yl)oxy)-1,8b-dihydroxy-8-methoxy-3a-(4-methoxyphenyl)-3-phenyl-2,3,3a,8b-tetrahydro-1H-cyclopenta[b]benzofuran-2-carboxylate

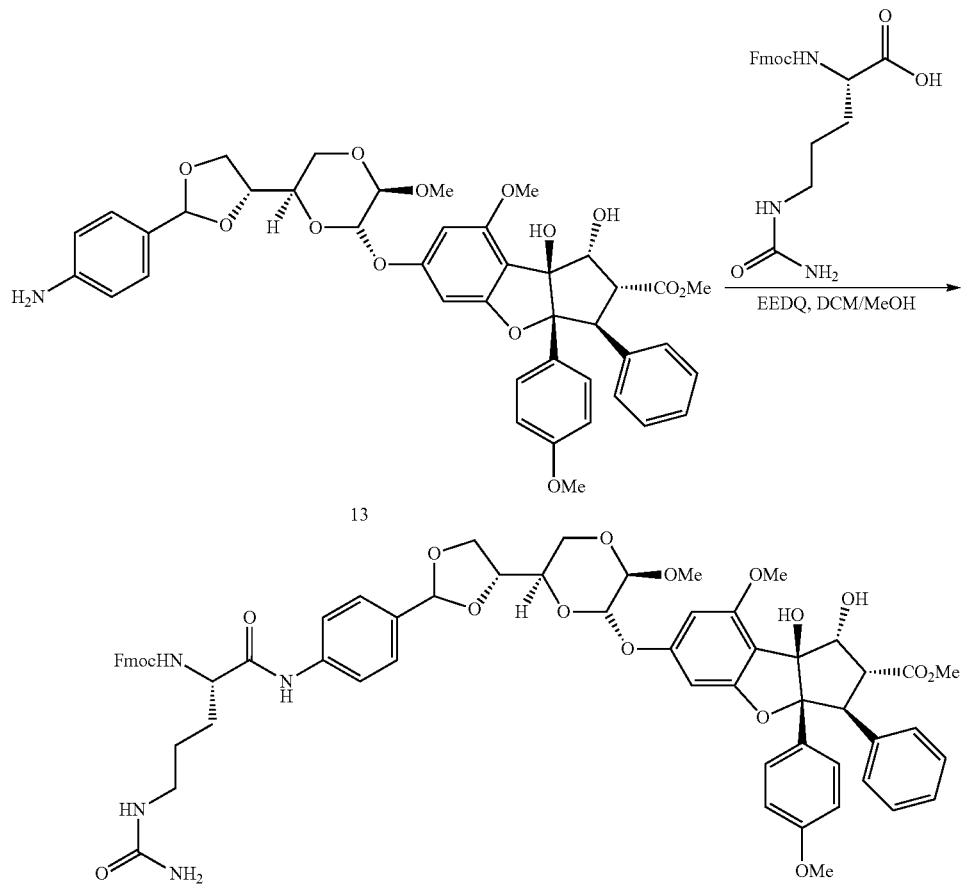

To a stirred solution of 13 (24 mg, 0.031 mmol) and (S)-2-((((9H-fluoren-9-yl)methoxy)carbonyl)amino)-5-ureidopentanoic acid (18.5 mg, 0.0465 mmol) in DCM/MeOH (3.0 mL/0.5 mL) was added 2-ethoxy-1-ethoxycarbonyl-1,2-dihydroquinoline, EEDQ (CAS Reg. No. 16357-59-8, Sigma-Aldrich, 16 mg, 0.062 mmol) at 20° C. The mixture was stirred at 20° C. for 16 h under $N_2$. The mixture was concentrated and purified by prep-TLC (DCM/MeOH=30/1) to give 18 (30 mg, 86%).

Step 11: Preparation of (1R,2R,3 S,3aR,8b S)-methyl 6-(((2S,3R,6R)-6-((4R)-2-(4-((S)-2-amino-5-ureidopentanamido)phenyl)-1,3-dioxolan-4-yl)-3-methoxy-1,4-dioxan-2-yl)oxy)-1,8b-dihydroxy-8-methoxy-3 a-(4-methoxyphenyl)-3-phenyl-2,3,3 a, 8b-tetrahydro-1H-cyclopenta[b]benzofuran-2-carboxylate 19

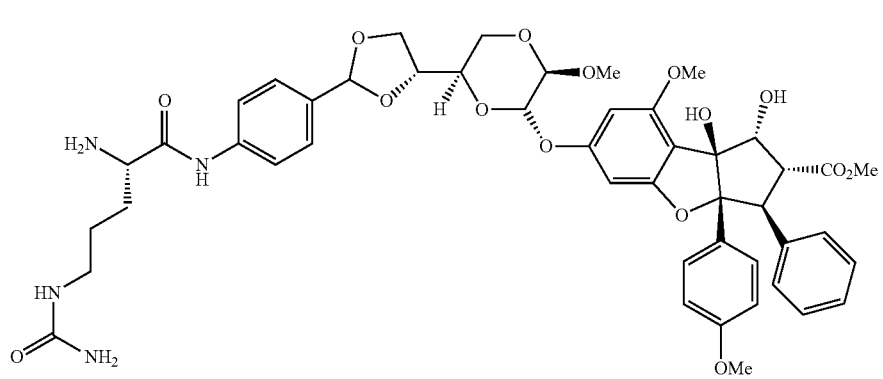

19

To a solution of 18 (30 mg, 0.0264 mmol) in anhydrous DMF (2.0 mL) was added piperidine (4.5 mmol, 0.0528 mmol) at 20° C. The mixture was stirred at 20° C. for 2 h. The mixture was concentrated to give crude 19, used for next step without further purification (24 mg, 100%).

Step 12: Preparation of Silvestrol-Linker Intermediate LD-51

Intermediates 19 (24 mg, 0.0264 mmol) and 15 (22 mg, 0.0528 mmol) were dissolved in anhydrous DMF (2.0 mL). The mixture was allowed to stir at 20° C. for 2 h. The mixture was concentrated and purified by prep-TLC (DCM/MeOH=10/1) to give LD-51 (13 mg, 41%). LCMS (5-95, AB, 1.5 min): $R_T$=0.889 min, m/z=1227.5[M+Na]$^+$; $^1$H NMR (400 MHz, DMSO-d$_6$) δ 9.86 (s, 1H), 7.62 (d, J=8.4 Hz, 2H), 7.61-7.50 (m, 2H), 7.44 (d, J=8.8 Hz, 2H), 7.05-7.00 (m, 5H), 6.92-6.70 (m, 4H), 6.59 (d, J=9.2 Hz, 2H), 6.41-6.35 (m, 2H), 5.84 (s, 1H), 5.69 (s, 1H), 5.32 (s, 1H), 5.18 (s, 2H), 4.86 (s, 1H), 4.75 (d, J=4.8 Hz, 2H), 4.62 (s, 1H), 4.51-4.38 (m, 1H), 4.37-4.20 (m, 2H), 4.18-3.98 (m, 1H), 3.98-3.91 (m, 4H), 3.74 (s, 1H), 3.59 (m, 7H), 3.43-3.38 (m, 5H), 2.61 (s, 2H), 2.44 (d, J=10.0 Hz, 4H), 1.80-1.55 (m, 4H), 1.53-1.45 (m, 6H), 1.27-1.22 (m, 4H).

Example 1b

Silvestrol-Linker Intermediate LD-52 (Table 5). Synthesis of 4-((S)-2-((S)-2-(6-(2,5-dioxo-2,5-dihydro-1H-pyrrol-1-yl)hexanamido)-3-methylbutanamido)-5-ureidopentanamido)benzyl (2-(((1R,2R,3S,3aR,8bS)-6-(((2S,3R,6R)-6-((R)-1,2-dihydroxyethyl)-3-methoxy-1,4-dioxan-2-yl)oxy)-1,8b-dihydroxy-8-methoxy-3a-(4-methoxyphenyl)-3-phenyl-2,3,3a,8b-tetrahydro-1H-cyclopenta[b]benzofuran-2-carboxamido)ethyl)carbamate LD-52

Step 1: Preparation of (1R,2R,3S,3aR,8bS)-6-(((2S,3R,6R)-6-((R)-1,2-dihydroxyethyl)-3-methoxy-1,4-dioxan-2-yl)oxy)-1,8b-dihydroxy-8-methoxy-3a-(4-methoxyphenyl)-3-phenyl-2,3,3a,8b-tetrahydro-1H-cyclopenta[b]benzofuran-2-carboxylic acid 20

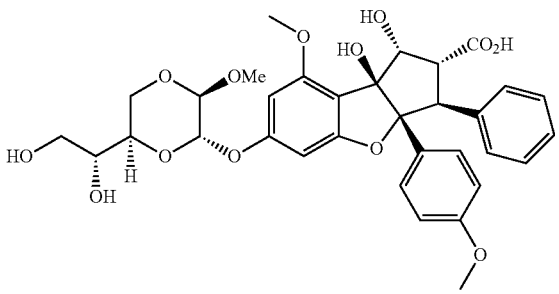

20

To the mixture of silvestrol 16 (40.0 mg, 0.060 mmol) in THF (1.0 mL) was added LiOH (11.71 mg, 0.490 mmol) in water (1.0 mL) dropwise. The reaction mixture was stirred at 15° C. for 24 h. The mixture was diluted with water (3.0 mL), adjusted to pH 3, and extracted with DCM (5.0 mL×3). The combined organic layer was dried and concentrated to give 20 (39 mg, 0.0597 mmol, 97.6% yield) as a white solid, which was used directly to the next step without further purification. LCMS (5-95AB/1.5 min): RT=0.798 min, [M+Na]⁺663.1

Step 2: Preparation of (9H-fluoren-9-yl)methyl (2-aminoethyl)carbamate

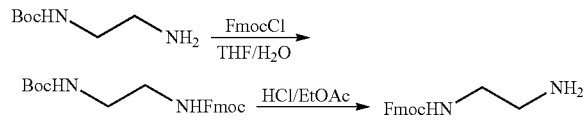

To a mixture of tert-butyl (2-aminoethyl)carbamate (200.0 mg, 1.25 mmol), sodium bicarbonate (157 mg, 1.87 mmol) in THF (5.0 mL) and water (5.0 mL) was added 9-Fluorenylmethoxycarbonyl chloride, 9-Fluorenylmethyl chloroformate, Fmoc-Cl (484 mg, 1.87 mmol) at 0° C. The mixture was stirred at 15° C. for 1 h. The mixture was extracted with EtOAc (15 mL×3). The combined organic layer was washed with brine (15 mL), dried and concentrated. The residue was purified by silica gel chromatography (0-40% EtOAc in PE) to give (9H-fluoren-9-yl)methyl tert-butyl ethane-1,2-diyldicarbamate (250 mg, 0.595 mmol, 47.7% yield) as a yellow oil. LCMS (5-95AB/1.5 min): RT=0.931 min, [M+Na]⁺405.1.

To the mixture of (9H-fluoren-9-yl)methyl tert-butyl ethane-1,2-diyldicarbamate (100.0 mg, 0.260 mmol) EtOAc (2.0 mL) was added HCl (1.0 mL, 4 mol/L in EtOAc). After the reaction mixture was stirred at 0° C. for 30 min, it was concentrated to give (9H-fluoren-9-yl)methyl (2-aminoethyl)carbamate (73 mg, 0.199 mmol, 76.1% yield) as a white solid, which was used directly to the next step without further purification.

Step 3: Preparation of (9H-fluoren-9-yl)methyl (2-((1R,2R,3S,3aR,8bS)-6-(((2S,3R,6R)-6-((R)-1,2-dihydroxyethyl)-3-methoxy-1,4-dioxan-2-yl)oxy)-1, 8b-dihydroxy-8-methoxy-3a-(4-methoxyphenyl)-3-phenyl-2,3,3a,8b-tetrahydro-1H-cyclopenta[b]benzofuran-2-carboxamido)ethyl)carbamate 21

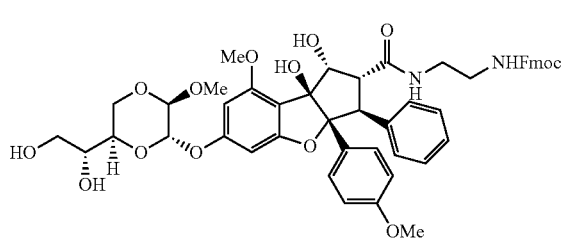

A mixture of compound 20 (31.42 mg, 0.160 mmol), 1-hydroxybenzotriazole (HOBt, 22.15 mg, 0.160 mmol) and (9H-fluoren-9-yl)methyl (2-aminoethyl)carbamate (46.25 mg, 0.160 mmol) in DCM (5.0 mL) was stirred at 0° C. for 5 min. An excess of dicyclohexylcarbodiimide, DCC and diisopropylethylamine, DIEA (70.57 mg, 0.550 mmol) was added to the mixture. The reaction mixture was stirred at 15° C. for 1 h. The mixture was diluted with DCM (20 mL), and washed with brine (10 mL×2). The organic layer was dried and the residue was purified by prep-TLC (5% MeOH in DCM, Rf=0.4) to give 21 (40 mg, 0.0438 mmol, 80.1% yield) as a white solid. LCMS (5-95AB/1.5 min): RT=0.898 min, [M+H]⁺905.3.

Step 4: Preparation of (1R,2R,3S,3aR,8bS)-N-(2-aminoethyl)-6-(((2S,3R,6R)-6-((R)-1,2-dihydroxyethyl)-3-methoxy-1,4-dioxan-2-yl)oxy)-1,8b-dihydroxy-8-methoxy-3a-(4-methoxyphenyl)-3-phenyl-2,3,3a,8b-tetrahydro-1H-cyclopenta[b]benzofuran-2-carboxamide 21a

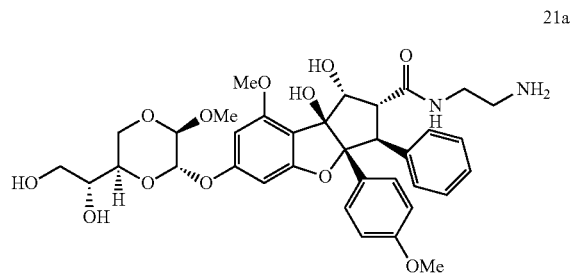 [SMILES: COc1ccc([C@@]23Oc4cc(O[C@@H]5O[C@@H]([C@H](O)CO)CO[C@H]5OC)cc(OC)c4[C@]2(O)[C@H](O)[C@H](C(=O)NCCN)[C@H]3c2ccccc2)cc1]

To a mixture of 21 (40.0 mg, 0.040 mmol) in DMF (1.0 mL) was added piperdine (15.05 mg, 0.180 mmol). The reaction mixture was stirred at 15° C. for 1 h. The mixture was purified by prep-HPLC (acetonitrile 20-50%/10 mM NH₄HCO₃-ACN) to afford 21a (5.6 mg, 0.0081 mmol, 18.4% yield) as a white solid. LCMS (5-95AB/1.5 min): RT=0.599 min, [M+H]+683.1.

Step 5: Preparation of Silvestrol-Linker Intermediate LD-52

To a solution of 4-((S)-2-((S)-2-(6-(2,5-dioxo-2,5-dihydro-1H-pyrrol-1-yl)hexanamido)-3-methylbutanamido)-5-ureidopentanamido)benzyl 4-nitrophenyl carbonate, MC-vc-PAB-PNP, prepared by methods described in WO 2012/113847; WO 2014/194247; U.S. Pat. Nos. 7,659,241; 7,498,298; US 2009/0111756; US 2009/0018086; U.S. Pat. No. 6,214,345; Dubowchik et al (2002) Bioconjugate Chem. 13(4):855-869, (13.91 mg, 0.020 mmol) and diisopropylethylamine, DIEA (8.12 mg, 0.060 mmol) in DMF (5.0 mL) was added 21a (0.020 mmol). The mixture was stirred at 25° C. for 12 h. The mixture was purified by prep-HPLC (acetonitrile 35-65/0.225% FA in water) to afford LD-52 as a white solid. LCMS m/z [M+Na]⁺ 1303.6.

Example 1c

Silvestrol-Linker Intermediate LD-53 (Table 5). Synthesis of (1R,2R,3S,3aR,8bS)-methyl 6-(((2S,3R,6S)-6-(2-((((4-((S)-2-((S)-2-(6-(2,5-dioxo-2,5-dihydro-1H-pyrrol-1-yl)hexanamido)-3-methylbutanamido)-5-ureidopentanamido)benzyl)oxy)carbonyl)amino)ethyl)-3-methoxy-1,4-dioxan-2-yl)oxy)-1,8b-dihydroxy-8-methoxy-3a-(4-methoxyphenyl)-3-phenyl-2,3,3a,8b-tetrahydro-1H-cyclopenta[b]benzofuran-2-carboxylate LD-53

Step 1: Preparation of (3R,6S)-6-(2-(benzyloxy)ethyl)-3-methoxy-1,4-dioxan-2-ol 23b

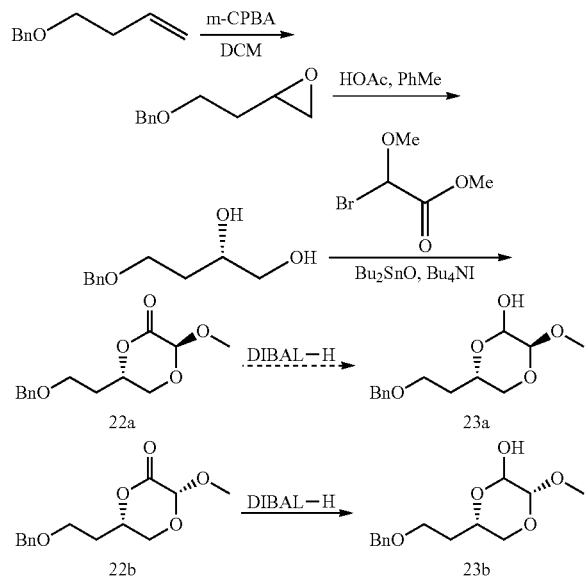

To a solution of ((but-3-en-1-yloxy)methyl)benzene (15.0 g, 92.46 mmol) in DCM (200 mL) was added meta-chloroperbenzoic acid, m-CPBA (37.54 g, 184.92 mmol) at 0° C. The reaction mixture was stirred at 20° C. for 12 h. The reaction mixture was quenched with aq. Na$_2$SO$_3$ (100 mL) and the aqueous layer was extracted with DCM (100 mL×3). The organic layer was washed with aq. NaHCO$_3$ (100 mL×3), dried and concentrated. The residue was purified by flash column chromatography (0-5% EtOAc in PE) to give 2-(2-(benzyloxy)ethyl)oxirane (10.5 g, 59.3%) as a colorless oil. LCMS (5-95AB/1.5 min): RT=0.646 min, [M+CH$_3$CN]$^+$ 219.8.

Alternatively, NaH (3.05 g, 60%, 76.27 mmol) was suspended in THF (100 mL) at 0° C. under N$_2$, and but-3-en-1-ol (5.0 g, 69.34 mmol) was added at 0° C. The reaction mixture was stirred at 0° C. for 30 min, and then benzyl bromide (BnBr, 9.95 mL, 83.21 mmol) was added at 0° C. The mixture was stirred at 20° C. for 12 h. The reaction was quenched with sat. aq. NH$_4$Cl (15 mL) at 0° C. and diluted with water (50 mL). The mixture was extracted with EtOAc (100 mL×2), and the combined organic layers were concentrated, and purified by flash chromatography (0-2% EtOAc in petroleum ether) to give ((but-3-en-1-yloxy)methyl)benzene (7.15 g, 63.6% yield) as a colorless oil. To a solution of ((but-3-en-1-yloxy)methyl)benzene (15.0 g, 92.46 mmol) in DCM (200 mL) was added meta-chloroperbenzoic acid (mCPBA, 37.54 g, 184.92 mmol) at 0° C. The reaction mixture was stirred at 20° C. for 12 h. The reaction mixture was quenched with cold aq. Na$_2$SO$_3$ (100 mL) and then the aqueous layer was extracted with DCM (100 mL×3). The organic layer was washed with aq. NaHCO$_3$ (100 mL×3), dried and concentrated (Caution: all peroxide need to be removed before concentration). It was purified by flash chromatography (0-5% EtOAc in petroleum ether) to give 2-(2-(benzyloxy)ethyl)oxirane (10.5 g, 59.3%) as a colorless oil. LCMS (5-95, AB, 1.5 min): R$_T$=0.646 min, [M+CH$_3$CN+H]$^+$ 219.8.

To a round bottom flask charged with HOAc (0.03 mL, 0.450 mmol) in toluene (10 mL) was added (R,R)-(−)-N,N'-bis(3,5-di-tert-butylsalicylidene)-1,2-cyclohexanediamino cobalt (II) (135.5 mg, 0.220 mmol) at 20° C. and the resulting solution was stirred at 20° C. for 0.5 h while the flask was open to air in order to absorb oxygen. The volatiles were removed under reduced pressure. Neat 2-(2-(benzyloxy)ethyl)oxirane (8.0 g, 44.89 mmol) was added, followed by the addition of distilled water (0.45 mL, 25.14 mmol) dropwise at 0° C. The resulting reaction mixture was allowed to warm to 20° C. slowly and stirred at 20° C. for 2 h. The reaction mixture was diluted with DCM (50 mL), and the mixture was washed with water (50 mL×3), dried over anhydrous sodium sulfate, and concentrated in vacuo. The residue was purified on silica gel column chromatography (0-5% MeOH in DCM) to afford (S)-4-(benzyloxy)butane-1,2-diol (3.80 g, 43.1%) as a gray oil, which was combined with other batch (total 6.5 g) and separated by SFC (OD50 mm*30 mm, 5 um; 15% Base-EtOH; flow: 60 mL/min) to provide (S)-4-(benzyloxy)butane-1,2-diol (5.30 g, 81.5%) as a brown oil with an EE of 96%. LCMS (5-95AB/1.5 min): RT=0.585 min, [M+Na]$^+$218.8.

To a solution of methyl 2-methoxyacetate (10.00 g, 96.06 mmol) in carbon tetrachloride (200 mL) was added azobisisobutyronitrile (AIBN, 78.87 mg, 0.480 mmol) and N-bromosuccinimide (NBS, 18.80 g, 105.67 mmol) with stirring. The reaction mixture was stirred at 85° C. for 2 h. The mixture was cooled to 20° C., filtered and dried over Na$_2$SO$_4$, and the filtrate was concentrated under reduced pressure to give methyl 2-bromo-2-methoxyacetate (15.00 g, 85.3%) as a yellow oil, which was used in the next step without further purification. $^1$H NMR (400 MHz, CDCl$_3$): δ 5.99 (s, 1H), 3.83 (s, 3H), 3.55 (s, 3H).

To a solution of (S)-4-(benzyloxy)butane-1,2-diol (1.00 g, 5.1 mmol) in MeOH (15 mL) was added dibutyltinoxide (1.52 g, 6.11 mmol). The reaction mixture was stirred at 65° C. for 12 h. After it was cooled to r.t., the solvent was removed in vacuo and the white solid was dried under high vacuum for 30 min. The resulting residue was then dissolved in toluene (15 mL). Tetrabutylammonium iodide (471 mg, 1.27 mmol) and methyl 2-bromo-2-methoxyacetate (2.05 g, 11.21 mmol) were then added and the resulted reaction mixture was stirred for an additional 2 h at 120° C. The mixture was concentrated and purified by silica gel column chromatography (EtOAc:PE 10%-20%) to give (3R,6S)-6-(2-(benzyloxy)ethyl)-3-methoxy-1,4-dioxan-2-one 22b (600 mg, 44.2%) and (3S,6S)-6-(2-(benzyloxy)ethyl)-3-methoxy-1,4-dioxan-2-one 22a (580 mg, 42.7%) as colorless oils.

22b: $^1$H NMR (400 MHz, CDCl$_3$): δ 7.36-7.28 (m, 5H), 4.90 (s, 1H), 4.83-4.82 (m, 1H), 4.50-4.49 (m, 2H), 3.93-3.90 (m, 1H), 3.76-3.75 (m, 1H), 3.63-3.60 (m, 2H), 3.49 (s, 3H), 1.89-1.87 (m, 2H).

22a: $^1$H NMR (400 MHz, CDCl$_3$): δ 7.37-7.29 (m, 5H), 4.94-4.91 (m, 2H), 4.51-4.50 (m, 2H), 4.14-4.10 (m, 1H), 3.69-3.61 (m, 3H), 3.50 (s, 3H), 2.05-1.90 (m, 2H).

To a solution of 22b (580.0 mg, 2.18 mmol) in toluene (15 mL) was added diisobutylaluminum hydride, DIBAL-H solution (CAS Reg. No. 1191-15-7, Sigma-Aldrich, 1.0 M, 619.53 mg, 4.36 mmol) in toluene at −78° C. under $N_2$. The mixture was stirred at −78° C. for 1 h. The reaction was quenched at −25° C. with 0.5 mL methanol and the mixture was stirred for 2 min. Rochelle salt solutions (15 mL 20% w/w) was added and stirred at r.t. for another 1 h. The residue was extracted with EtOAc (15 mL×2). The combined organic layers were washed with water (10 mL×2), brine (10 mL×2) and dried over sodium sulfate. The solvent was evaporated to give the crude compound 23b (580 mg, 99.2%) as a colorless oil, used directly without further purification.

Step 2: Preparation of (1R,2R,3S,3aR,8bS)-methyl 6-(((2S,3R,6S)-6-(2-(benzyloxy)ethyl)-3-methoxy-1,4-dioxan-2-yl)oxy)-1,8b-dihydroxy-8-methoxy-3a-(4-methoxyphenyl)-3-phenyl-2,3,3a,8b-tetrahydro-1H-cyclopenta[b]benzofuran-2-carboxylate

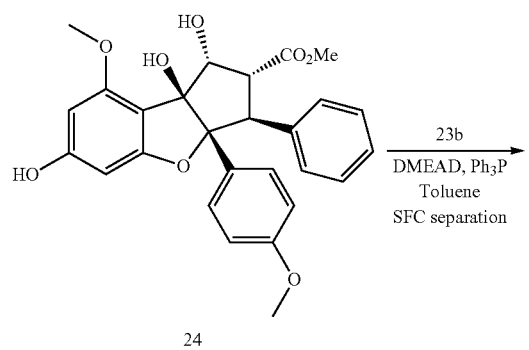

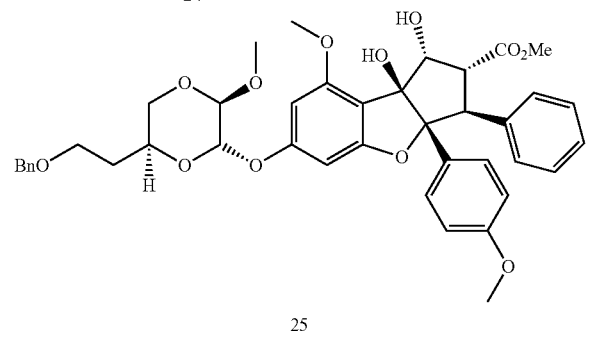

To a solution of (1R,2R,3S,3aR,8bS)-methyl 1,6,8b-trihydroxy-8-methoxy-3a-(4-methoxyphenyl)-3-phenyl-2,3,3a,8b-tetrahydro-1H-cyclopenta[b]benzofuran-2-carboxylate 24 (400.0 mg, 0.840 mmol) and 23b (576 mg, 2.15 mmol) in toluene (10 mL) was added triphenylphosphine, $PPh_3$ (570.09 mg, 2.17 mmol). The mixture was stirred at 20° C. for 30 min. To above solution was added a solution of DMEAD (509.06 mg, 2.17 mmol) in toluene (2.0 mL). The mixture was stirred at 20° C. for 12 h. The mixture was concentrated and purified by prep-HPLC (acetonitrile 60-80/0.225% FA in water) to afford two isomers, including 25 (peak 2 on HPLC, 242 mg, LCMS (5-95AB/1.5 min) RT=0.836 min, [M+Na]+751.1, 38.9%) as a white solid, and an isomer (peak 1 on HPLC, 130 mg, LCMS (5-95AB/1.5 min): RT=0.809 min, [M+Na]+751.0, 20.7% yield) as a white solid.

25, Peak 2: LCMS (5-95, AB, 1.5 min): $R_T$=0.836 min, [M+Na]+ 751.1. $^1$H NMR (400 MHz, CDCl$_3$) δ 7.33-7.29 (m, 1H), 7.13-7.09 (m, 8H), 7.07-7.03 (m, 3H), 6.81-6.68 (m, 2H), 6.51-6.50 (m, 1H), 6.34 (s, 1H), 5.29 (s, 1H), 4.98-4.96 (m, 1H), 4.61 (s, 1H), 4.33-4.20 (m, 4H), 3.84-3.50 (m, 17H), 1.78-1.73 (m, 2H), 1.32 (s, 1H).

Isomer, peak 1: LCMS (5-95, AB, 1.5 min): $R_T$=0.809 min, [M+Na]+ 751.1. $^1$H NMR (400 MHz, CDCl$_3$) δ 7.32-7.30 (m, 4H), 7.05-7.00 (m, 5H), 6.81-6.80 (m, 2H), 6.61-6.59 (m, 2H), 6.45 (s, 1H), 6.30 (s, 1H), 5.27 (s, 1H), 5.02-5.01 (m, 1H), 4.66-4.62 (m, 2H), 4.48-4.45 (m, 1H), 4.28-4.25 (m, 2H), 3.83-3.55 (m, 19H), 1.82-1.77 (m, 3H).

Step 3: Preparation of (1R,2R,3S,3aR,8bS)-methyl 1,8b-dihydroxy-6-(((2S,3R,6S)-6-(2-hydroxyethyl)-3-methoxy-1,4-dioxan-2-yl)oxy)-8-methoxy-3a-(4-methoxyphenyl)-3-phenyl-2,3,3a,8b-tetrahydro-1H-cyclopenta[b]benzofuran-2-carboxylate

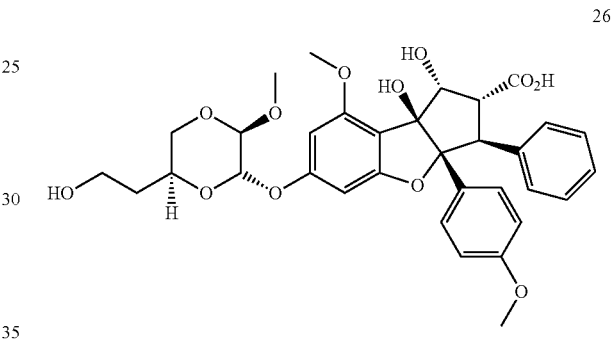

To a solution of 25 (242.0 mg, 0.330 mmol) in MeOH (2.0 mL) was added Pd/C (354 mg, 3.32 mmol). After the mixture was stirred at 30° C. under hydrogen gas, $H_2$ (1 atm) for 2 h, it was filtered and concentrated to give the 26 (209 mg, 0.321 mmol, 96.6% yield) as a white solid. LCMS (5-95AB/1.5 min): RT=0.717 min, [M+Na]+661.0.

Step 4: Preparation of (1R,2R,3S,3aR,8bS)-methyl 1,8b-dihydroxy-8-methoxy-6-(((2S,3R,6S)-3-methoxy-6-(2-((methylsulfonyl)oxy)ethyl)-1,4-dioxan-2-yl)oxy)-3a-(4-methoxyphenyl)-3-phenyl-2,3,3a,8b-tetrahydro-1H-cyclopenta[b]benzofuran-2-carboxylate 27

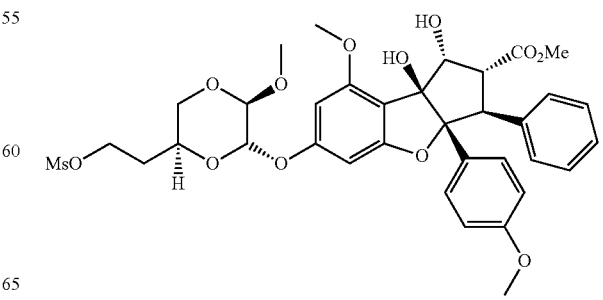

To a solution of 26 (200.0 mg, 0.310 mmol) in DCM (15 mL) was added triethylamine (0.22 mL, 1.57 mmol) and methanesulfonyl chloride (0.54 mL, 6.99 mmol). The mixture was stirred at 15° C. for 30 min. The mixture was diluted with DCM (25 mL) and washed with water (25 mL×3). The organic layer was concentrated to give the crude 27 (224 mg, 0.313 mmol, 99.8% yield) as a yellow oil. The crude was used directly without further purification.

Step 5: Preparation of (1R,2R,3S,3aR,8bS)-methyl 6-(((2S,3R,6S)-6-(2-azidoethyl)-3-methoxy-1,4-dioxan-2-yl)oxy)-1,8b-dihydroxy-8-methoxy-3a-(4-methoxyphenyl)-3-phenyl-2,3,3a,8b-tetrahydro-1H-cyclopenta[b]benzofuran-2-carboxylate

28

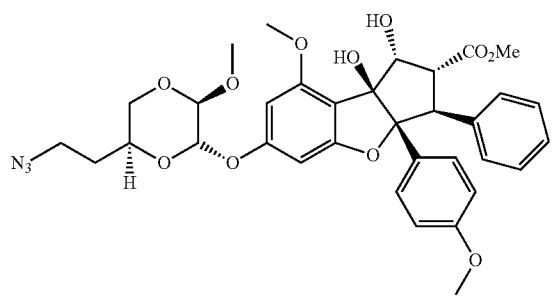

To a stirred solution of 27 (200.0 mg, 0.270 mmol) in DMF (10 mL) was added sodium azide (60.09 mg, 0.920 mmol) at 15° C. The mixture was stirred at 60° C. for 1 h. The mixture was added aqueous Na$_2$CO$_3$ (5 mL), and stirred for 5 min. The mixture was diluted with EtOAc (30 mL) and washed with water (30 mL×3) and brine (10 mL×3). The organic layer was dried over Na$_2$SO$_4$, concentrated and purified by prep-TLC (5% MeOH in DCM, Rf=0.5) to give 28 (40 mg, 0.0554 mmol, 20.3% yield) as a white solid. LCMS (5-95AB/1.5 min): RT=0.799 min, [M+Na]$^+$ 686.1.

Step 6: Preparation of (1R,2R,3S,3aR,8bS)-methyl 6-(((2S,3R,6S)-6-(2-aminoethyl)-3-methoxy-1,4-dioxan-2-yl)oxy)-1,8b-dihydroxy-8-methoxy-3a-(4-methoxyphenyl)-3-phenyl-2,3,3a,8b-tetrahydro-1H-cyclopenta[b]benzofuran-2-carboxylate

29

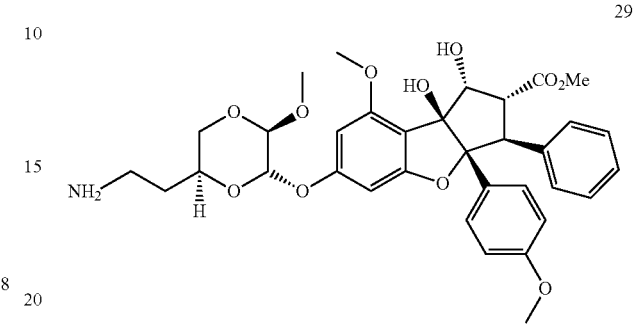

To a solution of 28 (40.0 mg, 0.060 mmol) in MeOH (5.0 mL) was added tert-butylamine (4.41 mg, 0.060 mmol) and Pd/C (64.19 mg). The mixture was stirred at 30° C. under H$_2$ (1 atm) for 1 h. The mixture was filtered, concentrated and purified by prep-HPLC (acetonitrile 10-40/0.225% FA in water) to give 29 (8.0 mg, 0.0125 mmol, 20.8% yield) as a white solid. LCMS (5-95AB/1.5 min): RT=0.661 min, [M+H]$^+$638.1. HPLC (10-80AB.met/8 min): RT=4.09 min.

Step 7: Preparation of Silvestrol-Linker Intermediate LD-53

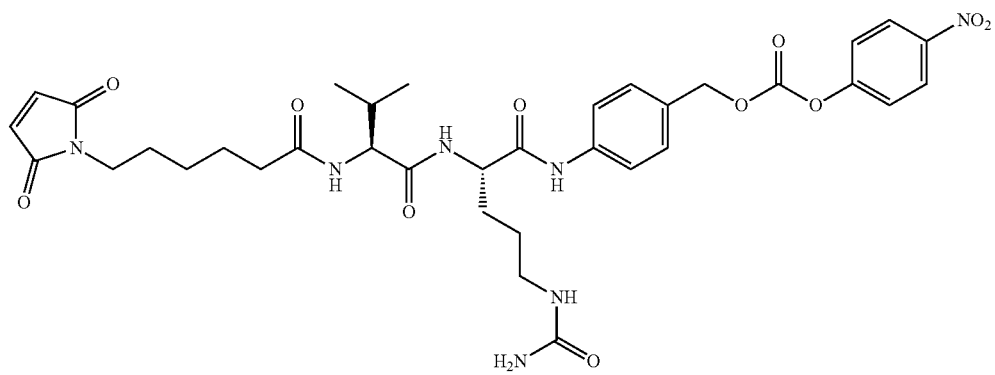 [SMILES: CC(C)[C@H](NC(=O)CCCCCN1C(=O)C=CC1=O)C(=O)N[C@@H](CCCNC(N)=O)C(=O)Nc1ccc(COC(=O)Oc2ccc([N+](=O)[O-])cc2)cc1]

To a solution of 4-((S)-2-((S)-2-(6-(2,5-dioxo-2,5-dihydro-1H-pyrrol-1-yl)hexanamido)-3-methylbutanamido)-5-ureidopentanamido)benzyl 4-nitrophenyl carbonate, MC-vc-PAB-PNP, prepared by methods described in WO 2012/113847; WO 2014/194247; U.S. Pat. Nos. 7,659,241; 7,498,298; US 2009/0111756; US 2009/0018086; U.S. Pat. No. 6,214,345; Dubowchik et al (2002) Bioconjugate Chem. 13(4):855-869, (13.91 mg, 0.020 mmol) and diisopropylethylamine, DIEA (8.12 mg, 0.060 mmol) in DMF (5.0 mL) was added 29 (10.0 mg, 0.020 mmol). The mixture was stirred at 25° C. for 12 h. The mixture was purified by prep-HPLC (acetonitrile 35-65/0.225% FA in water) to afford LD-53 (2.0 mg, 0.0015 mmol, 9.8% yield) as a white solid. LCMS (5-951.5 min): RT (220/254 nm)=0.759 min, [M+Na]⁺1258.2. HPLC (10-80AB/8 min): RT=4.89 min.

Example 1d

Silvestrol-Linker Intermediate LD-54 (Table 5). Synthesis of (1R,2R,3S,3aR,8bS)-methyl 1,8b-dihydroxy-8-methoxy-6-(((2S,3R,6S)-3-methoxy-6-(2-((5-nitropyridin-2-yl)disulfanyl)ethyl)-1,4-dioxan-2-yl)oxy)-3a-(4-methoxyphenyl)-3-phenyl-2,3,3a,8b-tetrahydro-1H-cyclopenta[b]benzofuran-2-carboxylate LD-54

Step 1: Preparation of (1R,2R,3S,3aR,8bS)-methyl 6#(25,3R,65)-6-(2-(acetylthio)ethyl)-3-methoxy-1,4-dioxan-2-yl)oxy)-1,8b-dihydroxy-8-methoxy-3a-(4-methoxyphenyl)-3-phenyl-2,3,3a,8b-tetrahydro-1H-cyclopenta[b]benzofuran-2-carboxylate 30

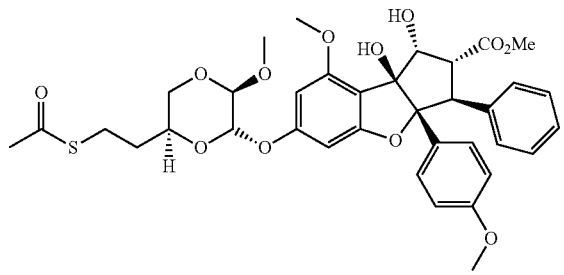

30

To a solution of (1R,2R,3S,3aR,8bS)-methyl 1,8b-dihydroxy-8-methoxy-6-(((2S,3R,6S)-3-methoxy-6-(2-((methylsulfonyl)oxy)ethyl)-1,4-dioxan-2-yl)oxy)-3a-(4-methoxyphenyl)-3-phenyl-2,3,3a,8b-tetrahydro-1H-cyclopenta[b]benzofuran-2-carboxylate 27 (34.0 mg, 0.050 mmol) in DMF (2.0 mL) was added ethanethioic S-acid, thiolacetic acid, KSAc (54.18 mg, 0.47 mmol). The mixture was stirred at 35° C. for 1 h. The mixture was concentrated and purified by prep-TLC (4% MeOH in DCM, Rf=0.5) to give 30 (15 mg, 0.0213 mmol, 44.9% yield) as a white solid. LCMS (5-95AB/1.5 min): RT=0.939 min, [M+Na]⁺ 719.1

Step 2: Preparation of (1R,2R,3S,3aR,8bS)-methyl 1,8b-dihydroxy-6-(((2S,3R,65)-6-(2-mercaptoethyl)-3-methoxy-1,4-dioxan-2-yl)oxy)-8-methoxy-3a-(4-methoxyphenyl)-3-phenyl-2,3,3a,8b-tetrahydro-1H-cyclopenta[b]benzofuran-2-carboxylate

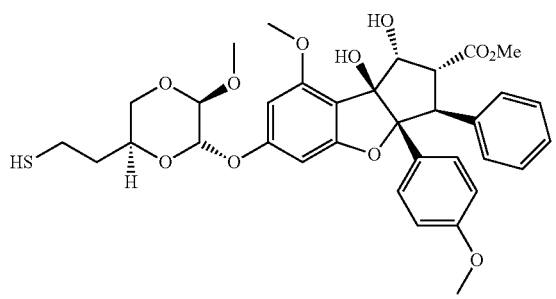

31

To a solution of 30 (12.0 mg, 0.02 mmol) in MeOH (2.0 mL) was added K₂CO₃ (7.14 mg, 0.050 mmol). The mixture was stirred at 35° C. for 1 h. The mixture was purified by prep-TLC (4% MeOH in DCM, Rf=0.5) and purified by prep-HPLC (FA) to give 31 (6.0 mg, 0.0091 mmol, 52.7% yield) as a white solid. LCMS (5-95AB/1.5 min): RT=0.805 min, [M+Na]⁺ 677.1. HPLC (10-80AB/8 min): RT=5.23 min.

Step 3: Preparation of Silvestrol-Linker Intermediate LD-54

A solution of 1,2-bis(5-nitropyridin-2-yl)disulfane and 31 in anhydrous DCM:CH₃OH/(1:1) was stirred at r.t. under N₂ for 24 h. After the mixture was concentrated under vacuum, and the residue was diluted with DCM. Manganese oxide (MnO₂) was added and the mixture was stirred at r.t. for another 0.5 h. The mixture was purified by LCMS to afford LD-55.

Example R1e

Silvestrol-Linker Intermediate LD-55 (Table 5). Synthesis of (1R,2R,3 S,3 aR, 8b S)-6-(((2 S,3R, 6R)-6-((R)-1,2-dihydroxyethyl)-3-methoxy-1,4-dioxan-2-yl)oxy)-1,8b-dihydroxy-8-methoxy-3a-(4-methoxyphenyl)-N-(2-((5-nitropyridin-2-yl)disulfanyl)ethyl)-3-phenyl-2,3,3a,8b-tetrahydro-1H-cyclopenta[b]benzofuran-2-carboxamide LD-55

Step 1: Preparation of (1R,2R,3S,3aR,8bS)-2,5-dioxopyrrolidin-1-yl 6-(((2S,3R,6R)-6-((R)-1,2-dihydroxyethyl)-3-methoxy-1,4-dioxan-2-yl)oxy)-1,8b-dihydroxy-8-methoxy-3a-(4-methoxyphenyl)-3-phenyl-2,3,3a,8b-tetrahydro-1H-cyclopenta[b]benzofuran-2-carboxylate 32

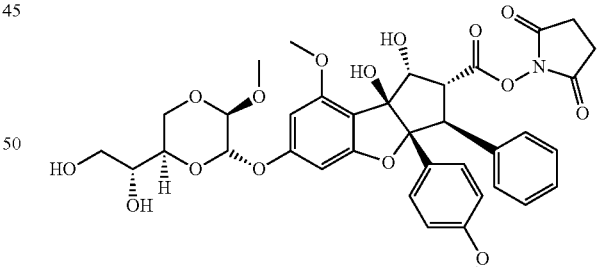

32

To a mixture of (1R,2R,3 S,3aR,8b S)-6-(((2S,3R,6R)-6-((R)-1,2-dihydroxyethyl)-3-methoxy-1,4-dioxan-2-yl)oxy)-1,8b-dihydroxy-8-methoxy-3 a-(4-methoxyphenyl)-3-phenyl-2,3,3 a, 8b-tetrahydro-1H-cyclopenta[b]benzofuran-2-carboxylic acid 20 (20.0 mg, 0.030 mmol) and 1-hydroxypyrrolidine-2,5-dione, N-hydroxysuccinimide, NHS, HOSu (3.59 mg, 0.0300 mmol) in THF (4.0 mL) was added dicyclohexylcarbodiimide, DCC (6.44 mg, 0.030 mmol). The reaction mixture was stirred at 15° C. for 16 h to produce 32, used directly in the next step.

Step 2: Preparation of (1R,2R,3S,3aR,8bS)-6-(((2S, 3R,6R)-6-((R)-1,2-dihydroxyethyl)-3-methoxy-1,4-dioxan-2-yl)oxy)-1,8b-dihydroxy-N-(2-mercaptoethyl)-8-methoxy-3a-(4-methoxyphenyl)-3-phenyl-2, 3,3a,8b-tetrahydro-1H-cyclopenta[b]benzofuran-2-carboxamide 33

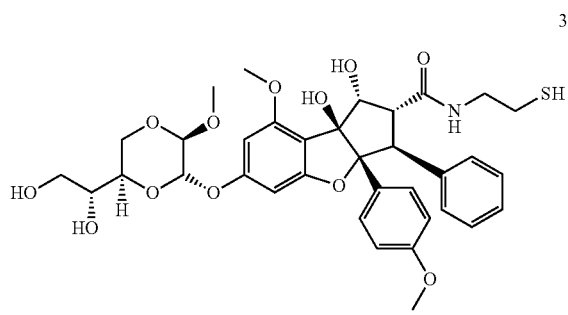

33

To a reaction mixture containing 32 was added 2-aminoethanethiol and TEA (8.23 mg, 0.080 mmol). The reaction mixture was stirred at 15° C. for 1 h. The mixture was concentrated, dissolved in DMF (2.0 mL), and purified by prep-HPLC (acetonitrile 30-60%/10 mM NH$_4$HCO$_3$-ACN) to afford 33 (1.74 mg, 0.0024 mmol, 9% yield) as a white solid. LCMS (5-95AB/1.5 min): RT=0.828 min, [M+H]$^+$ 700.2 and RT=0.898 min, [M+Na]$^+$ 1420.0 (with 17% of disulfide).

Step 3: Preparation of Silvestrol-Linker Intermediate LD-55

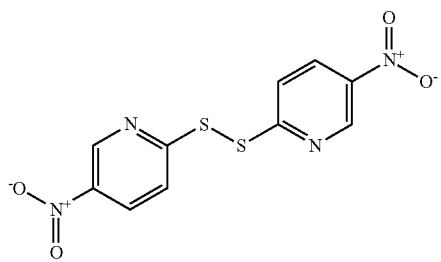

A solution of 1,2-bis(5-nitropyridin-2-yl)disulfane and 33 in anhydrous DCM:CH$_3$OH/(1:1) was stirred at r.t. under N$_2$ for 24 h. After the mixture was concentrated under vacuum, and the residue was diluted with DCM. Manganese oxide (MnO$_2$) was added and the mixture was stirred at r.t. for another 0.5 h. The mixture was purified by LCMS to afford LD-55.

Example 1f

Silvestrol-Linker Intermediate LD-58 (Table 5). Synthesis of methyl (1R,2R,3 S,3aR,8b S)-6-(((2S, 3R,6S)-6-(2-(((((4-((S)-2-(1-((5-(2,5-dioxo-2,5-dihydro-1H-pyrrol-1-yl)pentyl)carbamoyl)cyclobutane-1-carboxamido)-5-ureidopentanamido)benzyl) oxy)carbonyl)amino)ethyl)-3-methoxy-1,4-dioxan-2-yl)oxy)-1,8b-dihydroxy-8-methoxy-3a-(4-methoxyphenyl)-3-phenyl-2,3,3a,8b-tetrahydro-1H-cyclopenta[b]benzofuran-2-carboxylate LD-58

To a solution of (S)-4-(2-(1-(5-(2,5-dioxo-2,5-dihydro-1H-pyrrol-1-yl)pentylcarbamoyl)cyclobutanecarbox-amido)-5-ureidopentanamido)benzyl 4-nitrophenyl carbonate 12 (17.31 mg, 0.020 mmol) and DIEA (0.01 mL, 0.060 mmol) in DMF (3.0 mL) was added (1R,2R,3S,3aR,8bS)-methyl 6-(((2S,3R,6S)-6-(2-aminoethyl)-3-methoxy-1,4-dioxan-2-yl)oxy)-1,8b-dihydroxy-8-methoxy-3a-(4-methoxyphenyl)-3-phenyl-2,3,3a,8b-tetrahydro-1H-cyclopenta[b] benzofuran-2-carboxylate 29 (10.0 mg, 0.0200 mmol). The mixture was stirred at 25° C. for 12 h. The mixture was purified by prep-HPLC (acetonitrile 35-65/0.225% FA in water) to afford LD-58 (4.8 mg, 24.5%) as a white solid. LCMS (5-95, AB, 1.5 min): R$_T$=0.750 min, m/z=1256.6 [M+Na]$^+$.

Example 1g

Silvestrol-Linker Intermediate LD-59 (Table 5). Synthesis of 4-((S)-2-(1-((5-(2,5-dioxo-2,5-dihydro-1H-pyrrol-1-yl)pentyl)carbamoyl)cyclobutane-1-carboxamido)-5-ureidopentanamido)benzyl (2-((1R, 2R,3S,3aR,8b S)-6-(((2R,3R,6R)-6-((R)-1,2-dihydroxyethyl)-3-methoxy-1,4-dioxan-2-yl)oxy)-1, 8b-dihydroxy-8-methoxy-3a-(4-methoxyphenyl)-3-phenyl-2,3,3a,8b-tetrahydro-1H-cyclopenta[b] benzofuran-2-carboxamido)ethyl)carbamate LD-59

Step 1: Preparation of methyl (1R,2R,3S,3aR,8bS)-6-(((2S,3R,6R)-6-((R)-2-((tert-butyldimethylsilyl) oxy)-1-(((4-nitrophenoxy)carbonyl)oxy)ethyl)-3-methoxy-1,4-dioxan-2-yl)oxy)-1,8b-dihydroxy-8-methoxy-3a-(4-methoxyphenyl)-3-phenyl-2,3,3a,8b-tetrahydro-1H-cyclopenta[b]benzofuran-2-carboxylate 35

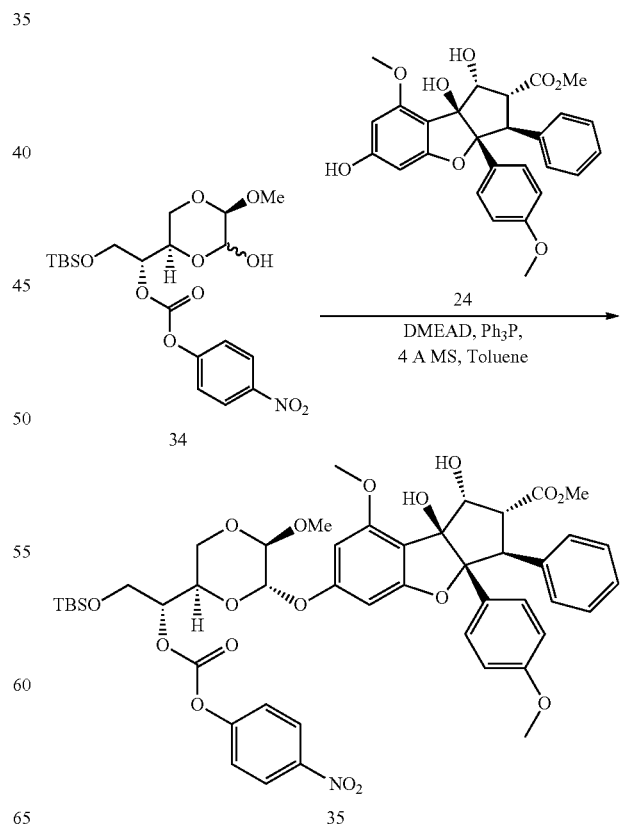

To a solution of 24 (300.0 mg, 0.6300 mmol) and (1R)-2-((tert-butyldimethylsilyl)oxy)-1-((2R,5R)-6-hydroxy-5-methoxy-1,4-dioxan-2-yl)ethyl (4-nitrophenyl) carbonate 34 (445.4 mg, 0.940 mmol) in toluene (15 mL) was added Ph₃P (427.6 mg, 1.63 mmol). The mixture was stirred at 20° C. for 10 min. To the above solution was added a solution of di-2-methoxyethyl azodicarboxylate, DMEAD (381.8 mg, 1.63 mmol) in toluene (5.0 mL) at 0° C. The mixture was stirred at 20° C. for 12 h. The mixture was filtered, concentrated and purified by prep-HPLC (85-90 (0.225% FA in water-ACN), 25 mL/min) to afford 35 (200 mg, 23.2%) as a white solid. ¹H NMR (400 MHz, CDCl₃) δ 8.24-8.21 (m, 4H), 7.14-7.11 (m, 2H), 7.07-7.05 (m, 3H), 6.87-6.86 (m, 2H), 6.71-6.69 (m, 2H), 6.53 (d, J=2.0 Hz, 1H), 6.31 (d, J=1.6 Hz, 1H), 5.35 (s, 1H), 5.25-5.23 (m, 1H), 5.04-5.02 (m, 1H), 4.65-4.63 (m, 2H), 4.36-4.32 (m, 1H), 4.09-3.89 (m, 5H), 3.81 (s, 3H), 3.74 (s, 3H), 3.71 (s, 3H), 3.58 (s, 1H), 3.51 (s, 3H), 0.83 (s, 9H), 0.02 (d, J=10.8 Hz, 6H). LCMS (5-95, AB, 1.5 min): $R_T$=1.012 min, [M+7]⁺ 940.3.

Step 2: Preparation of (1R,2R,3 S,3aR,8b S)-methyl 6-(((2S,3R,6R)-6-((R)-1,2-dihydroxyethyl)-3-methoxy-1,4-dioxan-2-yl)oxy)-1,8b-dihydroxy-8-methoxy-3 a-(4-methoxyphenyl)-3-phenyl-2,3,3 a,8b-tetrahydro-1H-cyclopenta[b]benzofuran-2-carboxylate

16

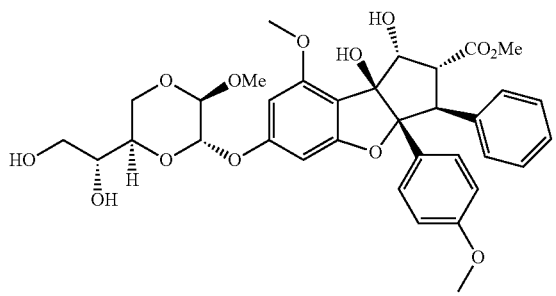

To a solution of 35 (150.0 mg, 0.1600 mmol) in THF (10 mL) was added tetrabutylammonium fluoride (TBAF, 125.97 mg, 0.480 mmol). The reaction mixture was stirred at 25° C. for 12 h. The reaction mixture was quenched with water (20 mL), and extracted with EtOAc (10 mL×2). The combined organic layers were washed with brine (20 mL), dried over Na₂SO₄, and concentrated in vacuo. The crude product was purified by flash chromatography (0-10% MeOH in DCM, Rf=0.4) to afford silvestrol 16 (95 mg, 90.4%) as a white solid. LCMS (5-95, AB, 1.5 min): $R_T$=0.724 min, [M+Na]⁺ 677.1.

Step 3: Preparation of (1R,2R,3S,3aR,8bS)-6-(((2S,3R,6R)-6-((R)-1,2-dihydroxyethyl)-3-methoxy-1,4-dioxan-2-yl)oxy)-1,8b-dihydroxy-8-methoxy-3a-(4-methoxyphenyl)-3-phenyl-2,3,3a,8b-tetrahydro-1H-cyclopenta[b]benzofuran-2-carboxylic acid 20

20

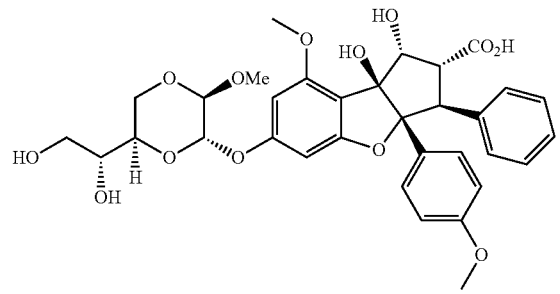

To a solution of 16 (50.0 mg, 0.0800 mmol) in THF (6.0 mL) and MeOH (2.0 mL) was added LiOH (9.15 mg, 0.380 mmol) in water (2.0 mL). The mixture was stirred at 20° C. for 12 h. The mixture was quenched with water (10 mL), extracted with EtOAc (10 mL×2). The aqueous layer was acidified with 1.0 M HCl to pH=4-5, and extracted with EtOAc (10 mL×2). The organic layer was dried over Na₂SO₄ and concentrated to afford 20 (41 mg, 68.7%) as a white solid. The crude was used directly without further purification. LCMS (5-95, AB, 1.5 min): $R_T$=0.669 min, [M+Na]⁺ 663.1.

Step 4: Preparation of (9H-fluoren-9-yl)methyl (2-((1R,2R,3S,3aR,8b S)-6-(((2 S,3R,6R)-6-((R)-1,2-dihydroxyethyl)-3-methoxy-1,4-dioxan-2-yl)oxy)-1,8b-dihydroxy-8-methoxy-3a-(4-methoxyphenyl)-3-phenyl-2,3,3a,8b-tetrahydro-1H-cyclopenta[b]benzofuran-2-carboxamido)ethyl)carbamate 21

21

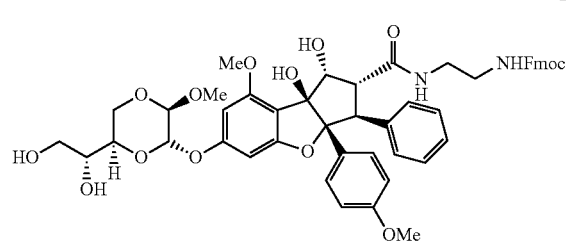

To a solution of 20 (40.0 mg, 0.060 mmol) in DCM (5.0 mL) was added (9H-fluoren-9-yl)methyl (2-aminoethyl)carbamate (26.44 mg, 0.090 mmol), HOBt (12.66 mg, 0.090 mmol), DCC (19.32 mg, 0.090 mmol) and DIEA (0.03 mL, 0.190 mmol). The mixture was stirred at 20° C. for 12 h. The mixture was concentrated and purified by prep-TLC (10% MeOH in DCM, Rf=0.3) to afford 21 (30 mg, 51.5%) as a white solid. LCMS (5-95, AB, 1.5 min): $R_T$=0.785 min, [M+H]⁺ 905.4.

Step 5: Preparation of (1R,2R,3S,3aR,8b S)-N-(2-aminoethyl)-6-(((2S,3R,6R)-6-((R)-1,2-dihydroxyethyl)-3-methoxy-1,4-dioxan-2-yl)oxy)-1,8b-dihydroxy-8-methoxy-3a-(4-methoxyphenyl)-3-phenyl-2,3,3a,8b-tetrahydro-1H-cyclopenta[b]benzofuran-2-carboxamide 21a

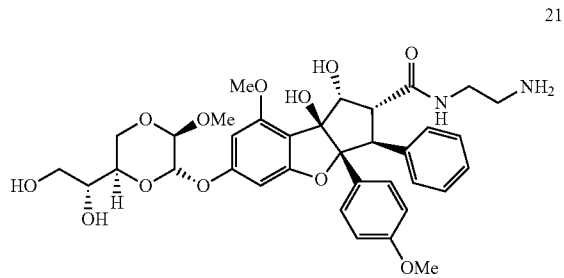

To a solution of 21 (15.0 mg, 0.0200 mmol) in DMF (2.0 mL) was added piperidine (0.02 mL, 0.050 mmol). The mixture was stirred at 25° C. for 1 h. LCMS showed the starting material was consumed and the desired product was found. The mixture was concentrated to afford compound 7 (11 mg, 97.2%) as a white solid, and was used directly without further purification. LCMS (5-95, AB, 1.5 min): $R_T$=0.607 min, $[M+H]^+$ 683.2.

Step 6: Preparation of LD-59

To a solution of (S)-4-(2-(1-(5-(2,5-dioxo-2,5-dihydro-1H-pyrrol-1-yl)pentylcarbamoyl)cyclobutanecarboxamido)-5-ureidopentanamido)benzyl 4-nitrophenyl carbonate 12 (17.78 mg, 0.0200 mmol) and DIEA (0.010 mL, 0.0600 mmol) in DMF (5.0 mL) was added 21a (11.0 mg, 0.020 mmol). The mixture was stirred at 25° C. for 12 h. LCMS showed the starting material was consumed and the desired product found. The mixture was purified by prep-HPLC (acetonitrile 35-50/0.225% FA in water, 25 mL/min) to afford LD-59 (10.1 mg, 48.5%) as a white solid. LCMS (5-95, AB, 1.5 min): $R_T$=0.688 min, $[M/2+H]^+$ 640.5.

Example 2

Preparation of Cysteine Engineered Antibodies

For large scale antibody production, antibodies were produced in CHO cells. Vectors coding for VL and VH were transfected into CHO cells and IgG was purified from cell culture media by protein A affinity chromatography.

As initially isolated, the engineered cysteine residues in antibodies exist as mixed disulfides with cellular thiols (e.g., glutathione) and are thus unavailable for conjugation. Partial reduction of these antibodies (e.g., with DTT), purification, and reoxidation with dehydroascorbic acid (DHAA) gives antibodies with free cysteine sulfhydryl groups available for conjugation, as previously described, e.g., in Junutula et al. (2008) Nat. Biotechnol. 26:925-932 and US 2011/0301334. Briefly, the antibodies were combined with the activated silvestrol drug moiety to allow conjugation to the free cysteine residues of the antibody. After several hours, the antibody-drug conjugates were purified.

Under certain conditions, the cysteine engineered antibodies were made reactive for conjugation with drugs by treatment with a reducing agent such as DTT (Cleland's reagent, dithiothreitol) or TCEP (tris(2-carboxyethyl)phosphine hydrochloride; Getz et al. (1999) Anal. Biochem. Vol 273:73-80; Soltec Ventures, Beverly, Mass.) in 50 mM Tris pH 7.5 with 2 mM EDTA for 3 hrs at 37° C. or overnight at room temperature. Full length, cysteine engineered monoclonal antibodies (THIOMAB™) expressed in CHO cells (Gomez et al. (2010) Biotechnology and Bioeng. 105(4): 748-760; Gomez et al. (2010) Biotechnol. Prog. 26:1438-1445) were reduced, for example with about a 50 fold excess of DTT overnight at room temperature to reduce disulfide bonds which may form between the newly introduced cysteine residues and the cysteine present in the culture media. The reduced THIOMAB™ was diluted and loaded onto a HiTrap S column in 10 mM sodium acetate, pH 5, and eluted with PBS containing 0.3M sodium chloride. Alternatively, the antibody was acidified by addition of $\frac{1}{20}^{th}$ volume of 10% acetic acid, diluted with 10 mM succinate pH 5, loaded onto the column and then washed with 10 column volumes of succinate buffer. The column was eluted with 50 mM Tris pH7.5, 2 mM EDTA.

Light chain amino acids are numbered according to Kabat (Kabat et al., Sequences of proteins of immunological interest, (1991) 5th Ed., US Dept of Health and Human Service, National Institutes of Health, Bethesda, Md.). Heavy chain amino acids are numbered according to the EU numbering system (Edelman et al. (1969) Proc. Natl. Acad. of Sci. 63(1):78-85), except where noted as the Kabat system. Single letter amino acid abbreviations are used.

Full length, cysteine engineered monoclonal antibodies (THIOMAB™) expressed in CHO cells bear cysteine adducts (cystines) or glutathionylated on the engineered cysteines due to cell culture conditions. To liberate the reactive thiol groups of the engineered cysteines, the THIOMAB™ was dissolved in 500 mM sodium borate and 500 mM sodium chloride at about pH 8.0 and reduced with about a 50-100 fold excess of 1 mM TCEP (tris(2-carboxyethyl) phosphine hydrochloride (Getz et al. (1999) Anal. Biochem. Vol 273:73-80; Soltec Ventures, Beverly, Mass.) for about 1-2 hrs at 37° C. Alternatively, DTT was used as reducing agent. The formation of inter-chain disulfide bonds was monitored either by non-reducing SDS-PAGE or by denaturing reverse phase HPLC PLRP column chromatography. The reduced THIOMAB™ was diluted and loaded onto a HiTrap SP FF column in 10 mM sodium acetate, pH 5, and eluted with PBS containing 0.3M sodium chloride, or 50 mM Tris-Cl, pH 7.5 containing 150 mM sodium chloride.

Disulfide bonds were reestablished between cysteine residues present in the parent Mab by carrying out reoxidation. The eluted reduced THIOMAB™ was treated with 15× or 2 mM dehydroascorbic acid (dhAA) at pH 7 for about 3 hours or for about 3 hrs in 50 mM Tris-Cl, pH 7.5, or with 200 nM to 2 mM aqueous copper sulfate ($CuSO_4$) at room temperature overnight. Other oxidants, i.e. oxidizing agents, and oxidizing conditions, which are known in the art may be used. Ambient air oxidation may also be effective. This mild, partial reoxidation step formed intrachain disulfides efficiently with high fidelity. The buffer was exchanged by elution over Sephadex G25 resin and eluted with PBS with 1 mM DTPA. The thiol/antibody value was checked by determining the reduced antibody concentration from the absorbance at 280 nm of the solution and the thiol concentration by reaction with DTNB (Aldrich, Milwaukee, Wis.) and determination of the absorbance at 412 nm.

Liquid chromatography/Mass Spectrometric Analysis was performed on a TSQ Quantum Triple quadrupole™ mass spectrometer with extended mass range (Thermo Electron, San Jose Calif.). Samples were chromatographed on a PRLP-S®, 1000 A, microbore column (50 mm×2.1 mm, Polymer Laboratories, Shropshire, UK) heated to 75° C. A linear gradient from 30-40% B (solvent A: 0.05% TFA in water, solvent B: 0.04% TFA in acetonitrile) was used and the eluent was directly ionized using the electrospray source. Data was collected by the Xcalibur® data system and deconvolution was performed using ProMass® (Novatia, LLC, N.J.). Prior to LC/MS analysis, antibodies or drug conjugates (50 micrograms) were treated with PNGase F (2 units/ml; PROzyme, San Leandro, Calif.) for 2 hours at 37° C. to remove N-linked carbohydrates.

Hydrophobic Interaction Chromatography (HIC) samples were injected onto a Butyl HIC NPR column (2.5 micron particle size, 4.6 mm×3.5 cm) (Tosoh Bioscience) and eluted with a linear gradient from 0 to 70% B at 0.8 ml/min (A: 1.5 M ammonium sulfate in 50 mM potassium phosphate, pH 7, B: 50 mM potassium phosphate pH 7, 20% isopropanol). An Agilent 1100 series HPLC system equipped with a multi wavelength detector and Chemstation software was used to resolve and quantitate antibody species with different ratios of drugs per antibody.

Example 3

Conjugation of Silvestrol-Linker Intermediate to Antibodies

After the reduction and reoxidation procedures of Example 1, the cysteine-engineered antibody (THIO-MAB™) is dissolved in PBS (phosphate buffered saline) buffer and chilled on ice. An excess, from about 1.5 molar to 20 equivalents of a silvestrol-linker intermediate, activated with a thiol-reactive group such as pyridyl disulfide, maleimide, or bromoacetamide, is dissolved in DMSO, diluted in acetonitrile and water, and added to the chilled, reduced, and reoxidized antibody in PBS. Typically the drug is added from a DMSO stock at a concentration of about 20 mM in 50 mM Tris, pH 8, to the antibody and monitored until the reaction is complete from about 1 to about 24 hours as determined by LC-MS analysis of the reaction mixture. When the reaction is complete, an excess of a capping reagent such as ethyl maleimide is added to quench the reaction and cap any unreacted antibody thiol groups. The conjugation mixture may be loaded and eluted through a HiTrap SP FF column to remove excess drug and other impurities. The reaction mixture is concentrated by centrifugal ultrafiltration and the cysteine engineered antibody-drug conjugate is purified and desalted by elution through G25 resin in PBS, filtered through 0.2 µm filters under sterile conditions, and frozen for storage.

For example, the crude antibody-drug conjugate is applied to a cation exchange column after dilution with 20 mM sodium succinate, pH 5. The column was washed with at least 10 column volumes of 20 mM sodium succinate, pH 5, and the antibody was eluted with PBS. The antibody-drug conjugates were formulated into 20 mM His/acetate, pH 5, with 240 mM sucrose using gel filtration columns. The antibody-drug conjugates were characterized by UV spectroscopy to determine protein concentration, analytical SEC (size-exclusion chromatography) for aggregation analysis and LC-MS before and after treatment with Lysine C endopeptidase.

Size exclusion chromatography is performed using a Shodex KW802.5 column in 0.2M potassium phosphate pH 6.2 with 0.25 mM potassium chloride and 15% IPA at a flow rate of 0.75 ml/min. Aggregation state of the conjugate was determined by integration of eluted peak area absorbance at 280 nm.

LC-MS analysis may be performed using an Agilent QTOF 6520 ESI instrument. As an example, the antibody-drug conjugate is treated with 1:500 w/w Endoproteinase Lys C (Promega) in Tris, pH 7.5, for 30 min at 37° C. The resulting cleavage fragments are loaded onto a 1000 Å (Angstrom), 8 µm (micron) PLRP-S (highly cross-linked polystyrene) column heated to 80° C. and eluted with a gradient of 30% B to 40% B in 5 minutes. Mobile phase A was $H_2O$ with 0.05% TFA and mobile phase B was acetonitrile with 0.04% TFA. The flow rate was 0.5 ml/min. Protein elution was monitored by UV absorbance detection at 280 nm prior to electrospray ionization and MS analysis. Chromatographic resolution of the unconjugated Fc fragment, residual unconjugated Fab and drugged Fab was usually achieved. The obtained m/z spectra were deconvoluted using Mass Hunter™ software (Agilent Technologies) to calculate the mass of the antibody fragments.

Example 4

In Vitro Cell Proliferation Assay

Efficacy of the antibody-drug conjugates Thio Hu Anti-CD22 10F4v3 LC K149C silvestrol and Thio Hu Anti-Ly6E 9B12.v12 LC K149C silvestrol was measured by a cell proliferation assay employing the following protocol (CELLTITER GLO™ Luminescent Cell Viability Assay, Promega Corp. Technical Bulletin TB288; Mendoza et al. (2002) Cancer Res. 62:5485-5488):

1. An aliquot of 40 µl of cell culture containing about 4000 cells (HER-expressing SK-BR-3 and KPL-4, CD22-positive BJAB, CD22-positive WSU-DLCL2 or Jurkat) in medium was deposited in each well of a 384-well, opaque-walled plate.
2. Control wells were prepared containing medium and without cells.
3. Antibody-drug conjugate (n=3) was added to the experimental wells and incubated for 3 to 5 days.
4. The plates were equilibrated to room temperature for approximately 30 minutes.
5. A volume of CELLTITER GLO™ Reagent equal to the volume of cell culture medium present in each well was added.
6. The contents were mixed for 15 minutes on an orbital shaker to induce cell lysis.
7. The plate was incubated at room temperature for 5 minutes to stabilize the luminescence signal.
8. Luminescence was recorded and reported in graphs as % activity where RLU (relative luminescence units) was normalized to controls (no antibody control minus no cell control).

Data was plotted and illustrated in FIGS. 1A and 1B as individual points for each replicate (n=3) for each antibody. The protocol is a modification of the CELLTITER GLO™ Luminescent Cell. Media: BJAB, WSU-DLCL2, and Jurkat may be grown in media including RPMI-1640, 20% HI-FBS, 2 mM L-Glutamine.

Example 5

Tumor Growth Inhibition, In Vivo Efficacy in High Expressing HER2 Transgenic Explant Mice Tumors are established and allowed to grow to 150-200 $mm^3$ in volume (as measured using calipers) before a single treatment on day 0. Tumor volume is measured using calipers according to the formula: V (mm$^3$)=0.5A×B$^2$, where A and B are the long and short diameters, respectively. Mice are euthanized before tumor volume reached 3000 mm$^3$ or when tumors showed signs of impending ulceration. Data collected from each experimental group (10 mice per group) is expressed as mean±SE.

The Fo5 mouse mammary tumor model is employed to evaluate the in vivo efficacy of antibody-drug conjugates of the invention after single dose intravenous injections, and as described previously (Phillips G D L, Li G M, Dugger D L, et al. Targeting HER2-Positive Breast Cancer with Trastuzumab-DM1, an Antibody-Cytotoxic Drug Conjugate. (2008) Cancer Res. 68:9280-90), incorporated by reference herein. Anti-Her2 antibody-drug conjugates may be tested with the Fo5 model, a transgenic mouse model in which the human HER2 gene is over-expressed in mammary epithelium under transcriptional regulation of the murine mammary tumor virus promoter (MMTV-HER2). The HER2 over-expression causes spontaneous development of a mammary tumor. The mammary tumor of one of these founder animals (founder #5 [Fo5]) is propagated in subsequent generations of FVB mice by serial transplantation of tumor fragments (~2×2 mm in size). All studies are conducted in accordance with the Guide for the Care and Use of Laboratory Animals. Each antibody-drug conjugate (single dose) is dosed in nine animals intravenously at the start of the study, and 14 days post-transplant. Initial tumor size is about 200 mm$^3$ volume.

Other mammary fat pad transplant efficacy models may be employed as described (Chen et al. (2007) Cancer Res 67:4924-4932), evaluating tumor volume after a single intravenous dose and using tumors excised from a mouse bearing an intraperitoneal tumor, then serially passaged into the mammary fat pads of recipient mice.

Other cell lines that could be tested in this way include AU565, HCC1954, HCC1008, HCC2157, HCC202, HCC1419, HCC2218 and HCC1569.

Example 6

Efficacy of Silvestrol Antibody-Drug Conjugates

Breast cancer cell line HCC1569 (CRL-2330) was obtained from American Type Culture Collection (ATCC, Manassas, Va.). The HCC1569 X2 cell line is a derivative of the parental HCC1569 cell line (ATCC, CRL-2330) optimized for growth in vivo. Parental HCC1569 cells were injected subcutaneously in the right flank of female SCID Beige mice, one tumor was harvested, minced and grown in vitro resulting in a HCC1569 XI cell line. The HCC1569 XI line was injected again subcutaneously in the right flank of female SCID Beige mice in an effort to improve the growth of the cell line. A tumor from this study was collected and again adapted for in vitro growth to generate the HCC1569 X2 cell line. This cell line and tumors derived from this line express Ly6E.

SCID Beige mice were inoculated with about 2 million cells in histidine buffer #8 vehicle. When tumor volumes reached approximately 80-200 mm$^3$ (day 0), the animals were randomized into groups of about 6 to 10 each, and administered a single intravenous (IV) injection of either vehicle control or an antibody-drug conjugate at the following doses: 0.3 mg/kg, 1 mg/kg/3 mg/kg, 6 mg/kg and 10 mg/kg. Tumor volumes were measured twice per week until study end at 21 days. Tumor volume was measured and calculated based on two dimensions, measured using calipers, and was expressed in mm$^3$ according to the formula: V=0.5a×b$^2$, wherein a and b are the long and the short diameters of the tumor, respectively. To analyze the repeated measurement of tumor volumes from the same animals over time, a mixed modeling approach was used (see, e.g., Pinheiro J, et al. nlme: linear and nonlinear mixed effects models. 2009; R package, version 3.1-96). This approach can address both repeated measurements and modest dropout rates due to non-treatment related removal of animals before the study end. Cubic regression splines were used to fit a non-linear profile to the time courses of log 2 tumor volume at each dose level. These non-linear profiles were then related to dose within the mixed mode. All animal protocols were approved by an Institutional Animal Care and Use Committee (IACUC).

Example 7

Efficacy of Thio anti-CD22 LC-K149C-MC-vc-PAB-Silvestrol-Amine in Bjab-luc Human Xenograft Model in CB-17 Fox Chase SCID Mice Inoculate 55 C.B-17 SCID mice with 20 million Bjab-luc cells subcutaneously in a volume of 0.2 mL per mouse in the flank. When tumors have reached a mean tumor volume of 150-250 mm3, they were grouped out into 6 groups of 5 mice each. Single treatments are administered on Day 0. Volume not to exceed 0.2 ml, needle size 28 or 29 gauge.

Example 8

Efficacy of Thio anti-Her2 7C2 LC-K149C-MC-vc-PAB-Silvestrol-Amine in KPL4 Human Mammary Xenograft Model in scid Beige Mice Inoculate n=60 mice with KPL-4 cells at 3 million cells/mouse suspended in HBSS/matrigel, in the thoracic 2/3 mammary fat pad at a volume of 0.2 ml. When tumors have reached a mean tumor volume of 150-250 mm3, they will be grouped out into 8 groups of 5 mice each. Single treatments will be administered on Day 0. Volume not to exceed 0.2 ml, needle size 28 or 29 gauge.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

This written description uses examples to disclose the invention, including the best mode, and also to enable any person skilled in the art to practice the invention, including making and using any devices or systems and performing any incorporated methods. The patentable scope of the invention is defined by the Claims, and may include other examples that occur to those skilled in the art. Such other examples are intended to be within the scope of the Claims if they have structural elements that do not differ from the literal language of the claims, or if they include equivalent structural elements with insubstantial differences from the literal languages of the claims.

What is claimed is:

1. An antibody drug conjugate compound comprising an antibody covalently attached through a linker to a silvestrol drug moiety, selected from Formulas Ia and Ib:

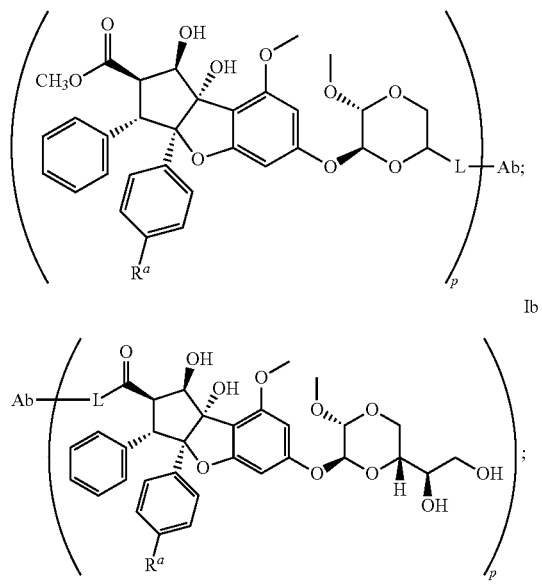

or a pharmaceutically acceptable salt thereof,
wherein
$R^a$ is a group selected from $CH_3O$, CN, $NO_2$, and Cl;
L is a linker selected from the group consisting of:
(i) a protease-cleavable, non-peptide linker having the formula;
where Str is a stretcher unit covalently attached to the antibody, Y is a spacer unit covalently attached to the silvestrol drug moiety, and PM is a peptidomimetic unit having the formula:

-Str-PM-Y—

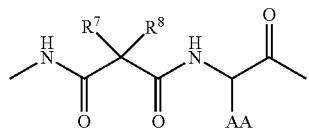

where $R^7$ and $R^8$ together form a $C_3$-$C_7$ cycloalkyl ring, and AA is an amino acid side chain selected from H, —$CH_3$, —$CH_2(C_6H_5)$, —$CH_2CH_2CH_2CH_2NH_2$, —$CH_2CH_2CH_2NHC(NH)NH_2$, —$CH_2CH(CH_3)_2$, and —$CH_2CH_2CH_2NHC(O)NH_2$; and
(ii) a peptide linker having the formula:

-Str-PM-Y— where Str is a stretcher unit covalently attached to the antibody; Pep is a peptide of two to twelve amino acid residues, and Y is a spacer unit covalently attached to the silvestrol drug moiety;

where for (i) and (ii) Str has the formula:

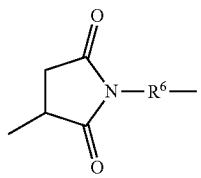

where $R^6$ is $(CH_2)_5$;
where for (i) and (ii) Y comprises para-aminobenzyl or para-aminobenzyloxycarbonyl;
p is an integer from 1 to 8; and
Ab is an antibody which binds to one or more tumor-associated antigens or cell-surface receptors.

2. The antibody-drug conjugate compound of claim 1 wherein the antibody which binds to one or more tumor-associated antigens or cell-surface receptors is selected from (1)-(53):
(1) BMPR1B (bone morphogenetic protein receptor-type 1B);
(2) E16 (LAT1, SLC7AS);
(3) STEAP1 (six transmembrane epithelial antigen of prostate);
(4) MUC16 (0772P, CA125);
(5) MPF (MPF, MSLN, SMR, megakaryocyte potentiating factor, mesothelin);
(6) Napi2b (NAPI-3B, SLC34A2, solute carrier family 34 (sodium phosphate), member 2, type II sodium-dependent phosphate transporter 3b);
(7) Sema 5b (FLJ10372, KIAA1445, Mm,42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B);
(8) PSCAhlg (2700050C12Rik, C530008016Rik, RIKEN cDNA 2700050C12, RIKEN cDNA 2700050C12 gene);
(9) ETBR (Endothelin type B receptor);
(10) MSG783 (RNF124, hypothetical protein FLJ20315);
(11) STEAP2 (HGNC_8639, IPCA-1, PCANAP1, STAMP1, STEAP2, sTMP, prostate cancer associated gene 1, prostate cancer associated protein 1, six transmembrane epithelial antigen of prostate 2, six transmembrane prostate protein);
(12) TrpM4 (BR22450, FLJ20041, TRPM4, TRPM4B, transient receptor potential cation channel, subfamily M, member 4);
(13) CRIPTO (CR, CR1, CRGF, CRIPTO, TDGF1, teratocarcinoma-derived growth factor);
(14) CD21 (CR2 (Complement receptor 2) or C3DR (C3d/Epstein Barr virus receptor) or Hs73792);
(15) CD79b, CD79B, CD79β, IGb (immunoglobulin-associated beta), B29);
(16) FcRH2 (IFGP4, IRTA4, SPAP1A (SH2 domain containing phosphatase anchor protein 1a), SPAN1B, SPAN1C);
(17) HER2;
(18) NCA;
(19) MDP;
(20) IL20Rα;
(21) Brevican;
(22) EphB2R;
(23) ASLG659;
(24) PSCA;
(25) GEDA;

(26) BAFF-R (B cell-activating factor receptor, BLyS receptor 3, BR3);
(27) CD22 (B-cell receptor CD22-B isoform);
(28) CD79a (CD79A, CD79α, immunoglobulin-associated alpha);
(29) CXCR5 (Burkitt's lymphoma receptor 1);
(30) HLA-DOB (Beta subunit of MHC class II molecule (Ia antigen));
(31) P2X5 (Purinergic receptor P2X ligand-gated ion channel 5);
(32) CD72 (B-cell differentiation antigen CD72, Lyb-2);
(33) LY64 (Lymphocyte antigen 64 (RP105), type I membrane protein of the leucine rich repeat (LRR) family);
(34) FcRH1 (Fc receptor-like protein 1);
(35) FcRH5 (1RTA2, Immunoglobulin superfamily receptor translocation associated 2);
(36) TENB2 (putative transmembrane proteoglycan);
(37) PMEL17 (silver homolog; SILV; DI2S53E; PMEL17; SI; SIL);
(38) TMEFF1 (transmembrane protein with EGF-like and two follistatin-like domains 1; Tomoregulin-1);
(39) GDNF-Ra1 (GDNF family receptor alpha 1; GFRA1; GDNFR; GDNFRA; RETL1; TRNR1; RET1L; GDNFR-alpha1; GFR-ALPHA-1);
(40) Ly 6E (lymphocyte antigen 6 complex, locus E; Ly67, RIG-E, SCA-2, TSA-1);
(41) TMEM46 (shisa homolog2 (Xenopus laevis); SHISA2);
(42) Ly6G6D (lymphocyte antigen 6 complex, locus G6D; Ly6-D, MEGTI);
(43) LGR5 (leucine-rich repeat-containing G protein-coupled receptor 5; GPR49, GPR67)
(44) RET (ret proto-oncogene; MEN2A; HSCR1; MEN2B; MTC1; PTC; CDHF12; Hs168114; RET5I; RET-ELE1);
(45) LY6K (lymphocyte antigen 6 complex, locus K; LY6K; HSJ001348; FLJ35226);
(46) GPR19 (G protein-coupled receptor 19; Mm 4787);
(47) GPR54 (KISS1 receptor; KISS1R; GPR54; HOT7T175; AXOR12);
(48) ASPHD1 (aspartate beta-hydroxylase domain containing 1; LOC253982);
(49) Tyrosinase (TYR; OCAIA; OCA1A; tyrosinase; SHEP3);
(50) TMEM118 (ring finger protein, transmembrane 2; RNFT2; :FLJ14627);
(51) GPR172A (G protein-coupled receptor 172A; GPCR41; FLJ11856; D15Ertd747e);
(52) CD33; and
(53) CLL-1.

3. The antibody-drug conjugate compound according to claim 2 wherein Ab is selected from anti-HER2 4D5, anti-CD22, anti-CD33, anti- Ly6E, anti-Napi3b, anti-HER2 7C2, and anti-CLL-1.

4. The antibody-drug conjugate compound according to claim 1, wherein Ab is a cysteine-engineered antibody.

5. The antibody-drug conjugate compound according to claim 4, wherein the cysteine-engineered antibody is a mutant selected from HC A118C, LC K149C, HC A140C, LC V205C, LC S121C, and HC L177C.

6. The antibody drug conjugate compound of claim 1 having the formula:

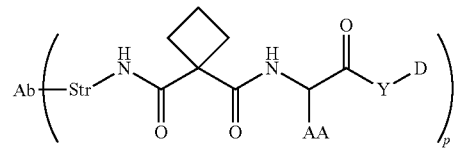

wherein D is the silvestrol drug moiety.

7. The antibody-drug conjugate compound of claim 6, having the formula:

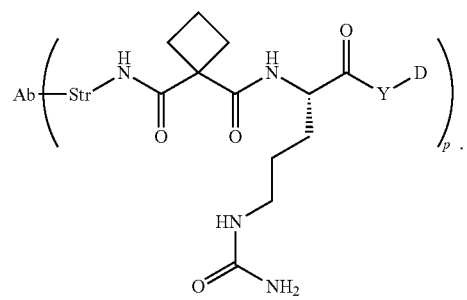

8. The antibody-drug conjugate compound of claim 6 having the formula:

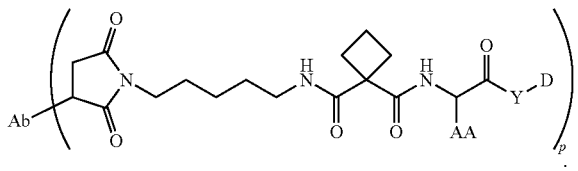

9. The antibody-drug conjugate compound of claim 8, having the formula:

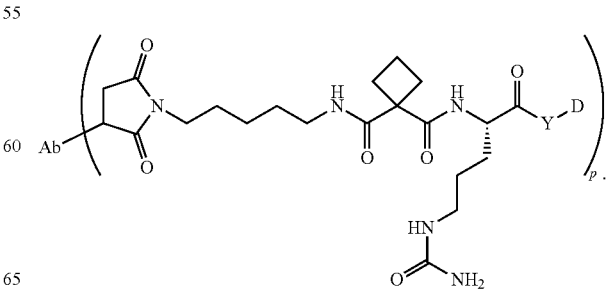

10. The antibody-drug conjugate compound of claim 9 selected from the formulas:

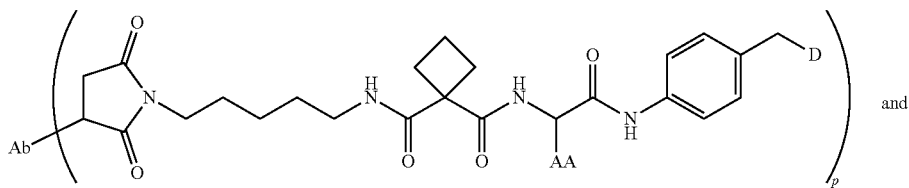

and

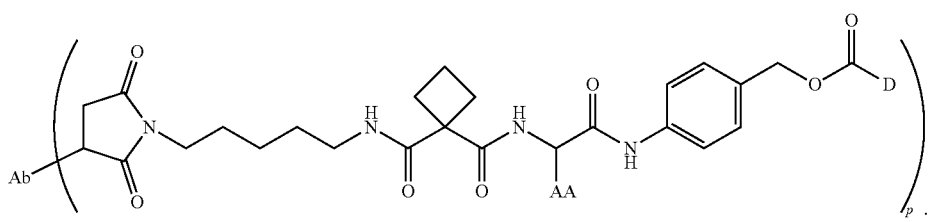

11. The antibody-drug conjugate compound of claim 1, wherein Pep comprises two to twelve amino acid residues independently selected from glycine, alanine, phenylalanine, lysine, arginine, value, and citrulline.

12. The antibody-drug conjugate compound of claim 11, wherein Pep is selected from valine-citrulline, alanine-phenylalanine, and phenylalanine-lysine.

13. The antibody-drug conjugate compound of claim 11 having the formula:

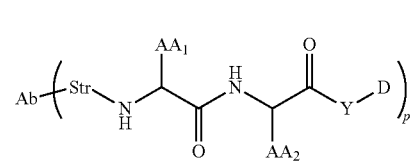

where $AA_1$ and $AA_2$ are each an amino acid side chain, independently selected from H, —$CH_3$, —$CH(CH_3)_2$, —$CH_2(C_6H_5)$, —$CH_2CH_2CH_2CH_2NH_2$, —$CH_2CH_2$ $CH_2NHC(NH)(NH)_2$, —$CH_2CH(CH_3)_2$, and —$CH_2$ $CH_2CH_2NHC(O)NH_2$.

14. The antibody-drug conjugate compound of claim 13 having the formula:

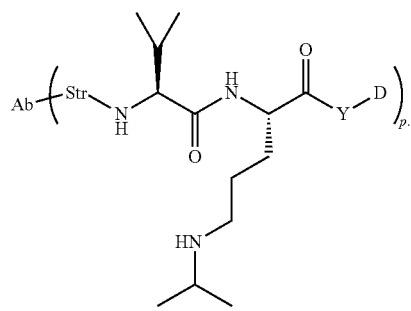

15. The antibody-drug conjugate compound of claim 13 having the formula:

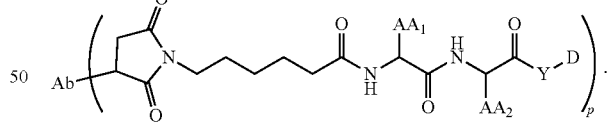

16. The antibody-drug conjugate compound of claim 15 having the formula:

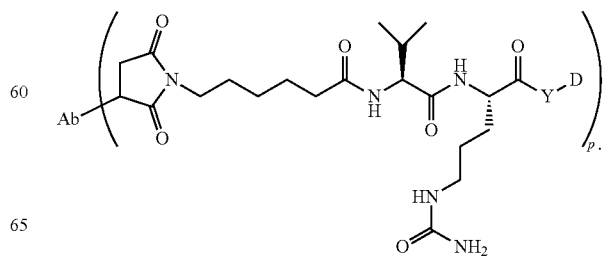

17. The antibody-drug conjugate of claim 13 having the formula:
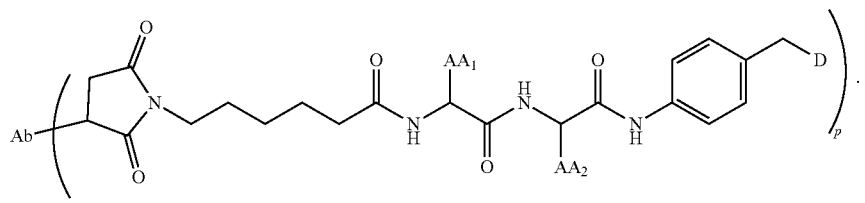
18. The antibody-drug conjugate of claim 17 having the formula:
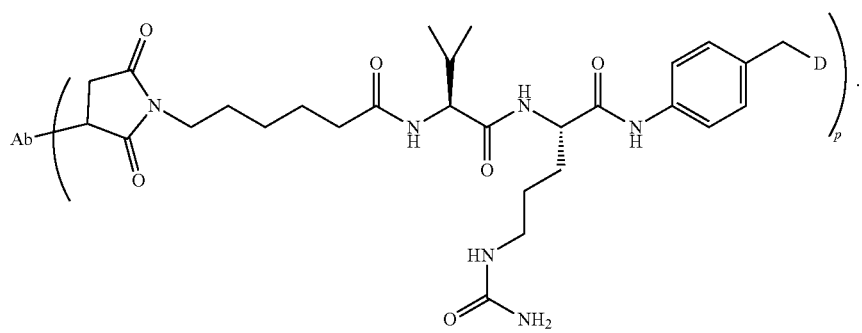
19. The antibody drug conjugate of claim 13 having the formula:
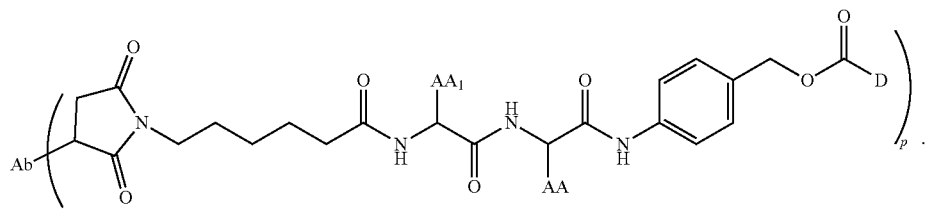
20. The antibody-drug conjugate of claim 19 having the formula:
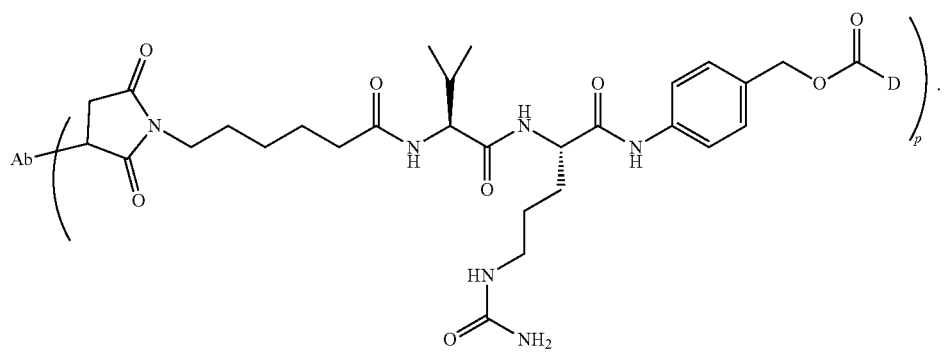

21. The antibody-drug conjugate compound according to claim 1, wherein p is 1, 2, 3, or 4.

22. The antibody-drug conjugate compound according to claim 1, comprising a mixture of the antibody-drug conjugate compounds, wherein the average drug loading per antibody in the mixture of antibody-drug conjugate compounds is about 2 to about 5.

23. A pharmaceutical composition comprising the antibody-drug conjugate compound according to claim 1 and a pharmaceutically acceptable diluent, carrier or excipient.

24. An article of manufacture comprising a pharmaceutical composition of claim 23, a container, and a package insert or label indicating that the pharmaceutical composition can be used to treat cancer.

* * * * *

UNITED STATES PATENT AND TRADEMARK OFFICE
CERTIFICATE OF CORRECTION

PATENT NO. : 11,648,315 B2
APPLICATION NO. : 16/827083
DATED : May 16, 2023
INVENTOR(S) : Thomas Pillow, Andrew G. Polson and Bing Zheng It is certified that error appears in the above-identified patent and that said Letters Patent is hereby corrected as shown below:

In the Claims

Column 99, Line 41, Claim 1, please delete "where Sir is" and insert --where Str is--;

Column 99, Line 63, Claim 1, please delete "-Str-PM-Y-" and insert -- -Str-Pep-Y- --;

Column 100, Line 29, Claim 2, please delete "NAPI-3B, SLC34A2," and insert --NAPI-3B, NPTIIb, SLC34A2,--;

Column 100, Line 32, Claim 2, please delete "Mm,42015," and insert --Mm.42015,--;

Column 100, Line 43, Claim 2, please delete "STEAP2, sTMP," and insert --STEAP2, STMP,--;

Column 100, Lines 57-58, Claim 2, please delete "SPAN1B, SPAN1C;" and insert --SPAP1B, SPAP1C;--;

Column 101, Line 32, Claim 2, please delete "(40) Ly 6E" and insert --(40) Ly6E--;

Column 101, Line 47, Claim 2, please delete "Mm 4787" and insert --Mm.4787--;

Column 103, Lines 64-65, Claim 13, please delete "-CH$_2$CH$_2$CH$_2$NHC(NH)(NH)$_2$" and insert -- -CH$_2$CH$_2$CH$_2$NHC(NH)NH$_2$--;

Signed and Sealed this
Eighteenth Day of June, 2024

Katherine Kelly Vidal
*Director of the United States Patent and Trademark Office*

CERTIFICATE OF CORRECTION (continued)
U.S. Pat. No. 11,648,315 B2

Column 104, Lines 30-42, Claim 14, please delete " 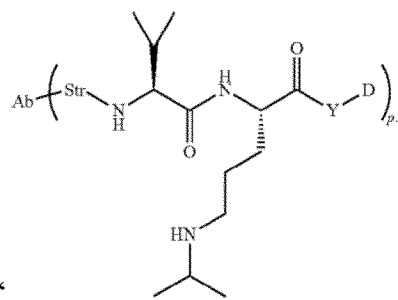 " and insert

-- 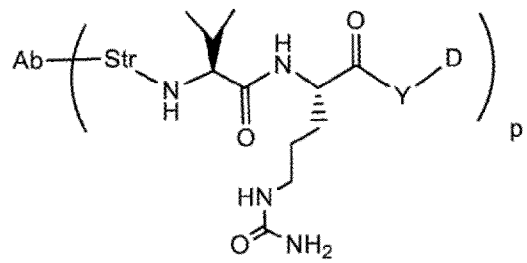 --; and

Column 105, Claim 19, please delete

" 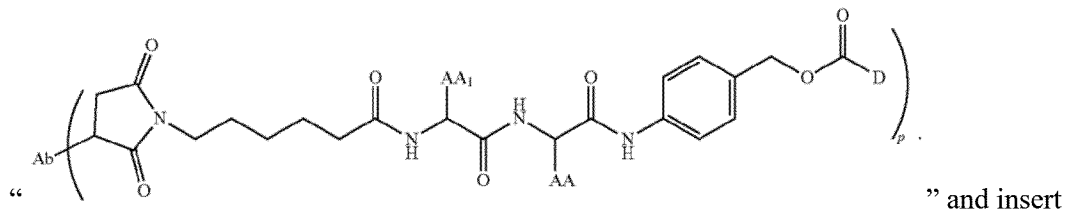 " and insert

-- 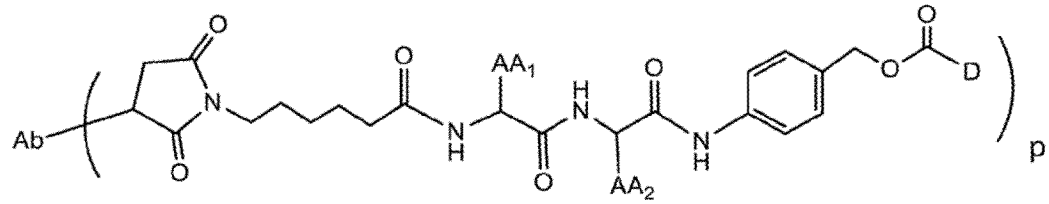 -- therefor.